US012617761B2

(12) United States Patent
Phillips

(10) Patent No.: US 12,617,761 B2
(45) Date of Patent: May 5, 2026

(54) PROCESS FOR PRODUCING HEXAHYDRO 1,3,5-TRINITRO-1,3,5-TRIAZINE AND OCTAHYDRO-1,3,5,7-TETRANITRO-1,3, 5,7-TETRAZOCINE

(71) Applicant: James E. Phillips, Kingsport, TN (US)

(72) Inventor: James E. Phillips, Kingsport, TN (US)

( * ) Notice: Subject to any disclaimer, the term of this patent is extended or adjusted under 35 U.S.C. 154(b) by 549 days.

(21) Appl. No.: 18/348,763

(22) Filed: Jul. 7, 2023

(65) Prior Publication Data

US 2024/0132454 A1 Apr. 25, 2024
US 2024/0228445 A9 Jul. 11, 2024

Related U.S. Application Data

(63) Continuation of application No. PCT/US2022/012078, filed on Jan. 12, 2022.

(60) Provisional application No. 63/136,931, filed on Jan. 13, 2021.

(51) Int. Cl.
*C07D 257/00* (2006.01)
*C07D 251/06* (2006.01)
*C07D 257/02* (2006.01)
*C07D 257/06* (2006.01)

(52) U.S. Cl.
CPC ......... *C07D 257/02* (2013.01); *C07D 251/06* (2013.01)

(58) Field of Classification Search
CPC ... C07D 257/02; C07D 257/00; C07D 257/06
See application file for complete search history.

(56) References Cited

U.S. PATENT DOCUMENTS

| | | |
|---|---|---|
| 3,987,034 A | 10/1976 | Thyagarajan |
| 4,086,228 A | 4/1978 | Solomon et al. |
| 4,163,845 A | 8/1979 | Brumley et al. |
| 5,250,687 A | 10/1993 | Lukasavage et al. |

FOREIGN PATENT DOCUMENTS

| | | |
|---|---|---|
| DE | 1939541 A1 | 2/1970 |
| FR | 2053804 A5 | 4/1971 |

OTHER PUBLICATIONS

Bachmann W E, Sheehan John C: "A New Method of Preparing the High Explosive RDX", J. Am. Chem. Soc., vol. 71, May 1, 1949 (May 1, 1949), pp. 1842-1845, XP055955809.
International Search Report for International Application No. PCT/US2022/012078, mailed Mar. 29, 2022.

*Primary Examiner* — Bruck Kifle
(74) *Attorney, Agent, or Firm* — Wiggin and Dana LLP

(57) ABSTRACT

Formation of methanoic acid, during the production of Hexahydro-1,3,5-trinitro-1,3,5-triazine and Octahydro-1,3,5,7-tetranitro-1,3,5,7-tetrazocine via the legacy Bachmann nitrolysis process, is avoided when the workup is performed under neutralized, anhydrous conditions. The recovered anhydrous spent acid is used directly in successive nitrolysis batches with minimal processing. The yield and quality of the hexahydro-1,3,5-trinitro-1,3,5-triazine and octahydro-1, 3,5,7-tetranitro-1,3,5,7-tetrazocine thus produced is equal to the yield and quality of the legacy process hexahydro-1,3, 5-trinitro-1,3,5-triazine and octahydro-1,3,5,7-tetranitro-1, 3,5,7-tetrazocine employing aqueous workup conditions.

29 Claims, 15 Drawing Sheets

Conventional RDX Process

RDX Process - Anhydrous Quench

RDX Process - Anhydrous Quench - Direct Recycle

*When directly recycling acetic acid, the ammonium nitrate therein is calculated and adjustments made to the heel to ensure a standard heel concentration.

RDX - No Quench - Azeotropic Distillation

RDX Process - Formic Acid Free Aqueous Quench

Conventional HMX Process

HMX Process - Anhydrous Quench

HMX Process - No Quench - Azeotropic Distillation

HMX Process – Formic Acid Free Aqueous Quench

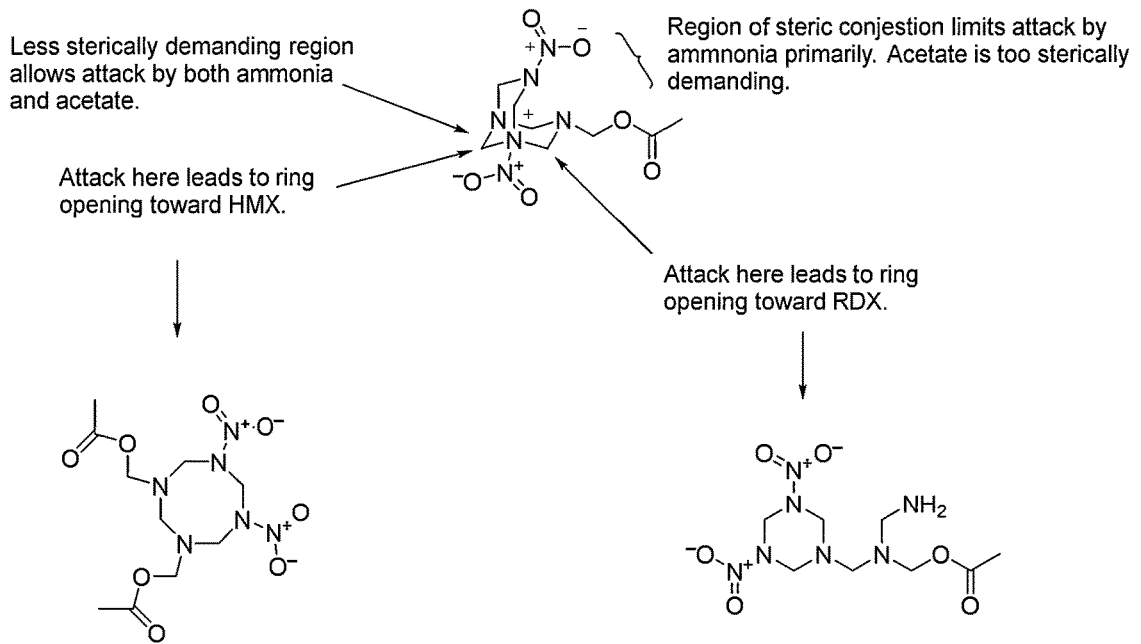

This mechanism is enabled by the presence of acetic anhydride to consume the water and drive the reaction.

H-2
1-acetoxymethyl-5-nitrobicyclo[3.3.1]-1,3,5,7-tetrazanonane.

Less sterically demanding region allows attack by both ammonia and acetate.

Region of steric conjestion limits attack by ammnonia primarily. Acetate is too sterically demanding.

Attack here leads to ring opening toward HMX.

Attack here leads to ring opening toward RDX.

1.) HMX process starts with no ammonia in the heel and delivers 38.6%of the ammonia concurrently with the hexamine stream. This would push the mechanism toward the HMX ring opening pathway.

1.) RDX process starts with ammonia in the heel and delivers 100% of the ammonia concurrently with the hexamine stream. This would favor the RDX ring opening pathway.

Figure 12C:
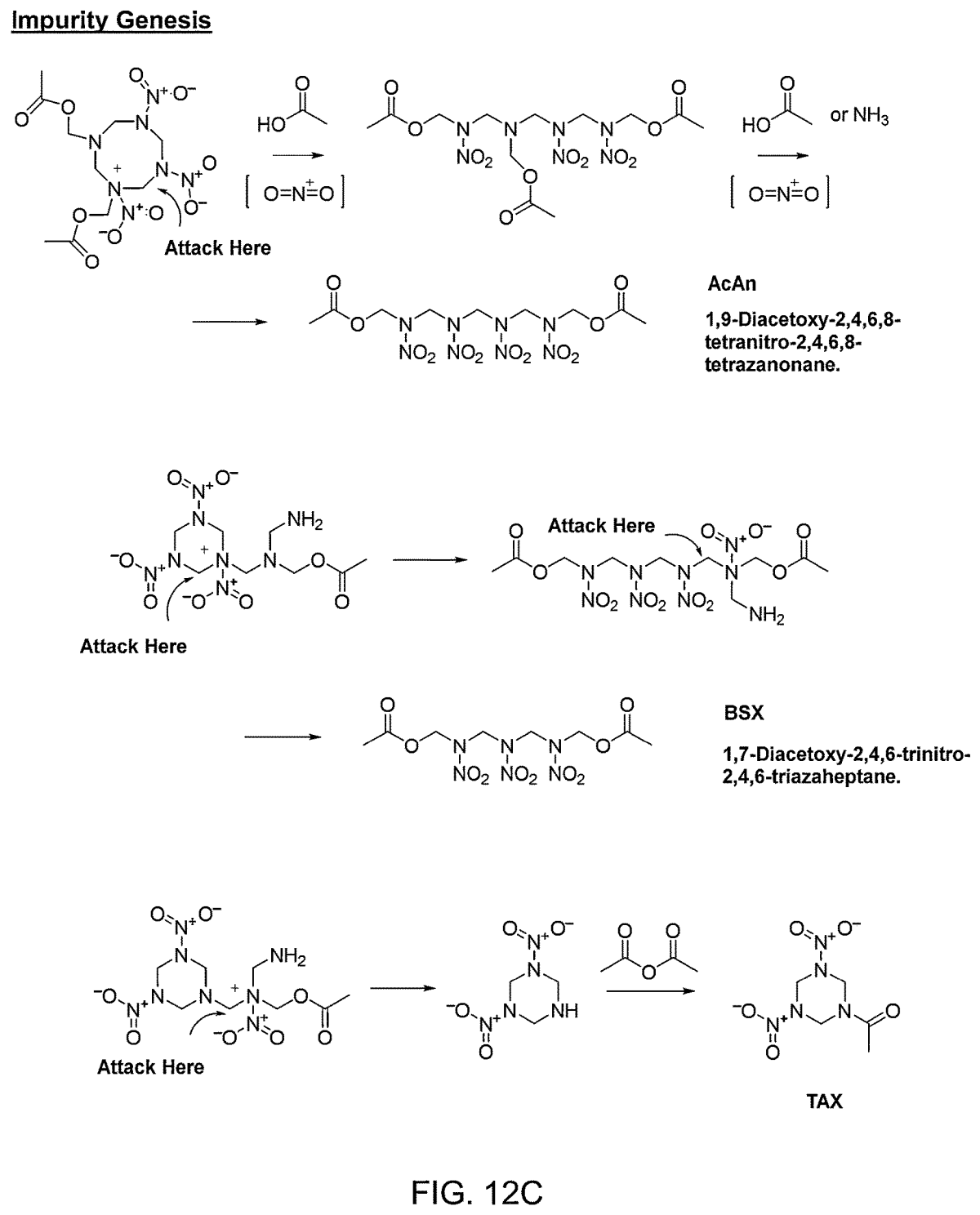

Impurity Genesis

AcAn 1,9-Diacetoxy-2,4,6,8-tetranitro-2,4,6,8-tetrazanonane.

BSX 1,7-Diacetoxy-2,4,6-trinitro-2,4,6-triazaheptane.

TAX

PROCESS FOR PRODUCING HEXAHYDRO 1,3,5-TRINITRO-1,3,5-TRIAZINE AND OCTAHYDRO-1,3,5,7-TETRANITRO-1,3,5,7-TETRAZOCINE

CROSS-REFERENCE TO RELATED APPLICATIONS

This application is a continuation of International Patent Application No. PCT/US2022/012078, filed Jan. 12, 2022, which claims priority under 35 U.S.C. § 119(e) to U.S. Provisional Patent Application No. 63/136,931, filed Jan. 13, 2021, each of which are hereby incorporated by reference in their entirety herein.

FIELD OF THE INVENTION

The present invention provides improved nitrolysis processes for making the explosive compounds hexahydro-1, 3,5-trinitro-1,3,5-triazine ("RDX") and octahydro-1,3,5,7-tetranitro-1,3,5,7-tetrazocine ("HMX"). These processes have the advantage of being substantially-free of methanoic acid (a.k.a formic acid), which is a highly-corrosive byproduct of conventional large-scale manufacturing processes. The present processes are achieved by a controlled quench of and without application of heat to the resultant product mixture to eliminate excess water while reducing residual levels of remaining acetic anhydride, and also by neutralizing excess nitric acid remaining in the resultant product mixture. In further aspects residual acetic anhydride is recovered for recycling back into the process.

BACKGROUND

Hexahydro-1,3,5-trinitro-1,3,5-triazine and Octahydro-1, 3,5,7-tetranitro-1,3,5,7-tetrazocine are high energy explosives produced on industrial scale by the Bachmann process, which is sometimes referred to as the legacy process. The Bachmann process involves the nitrolysis of 1,3,5,7-tetraazatricyclo[3.3.1.1$^{3,7}$]decane via a solution of nitric acid and ammonium nitrate in acetic acid in the presence of a dehydrating agent, acetic anhydride. The process is summarized in FIG. 1—Conventional Hexahydro-1,3,5-trinitro-1, 3,5-triazine Flow Diagram and FIG. 2—Conventional Octahydro-1,3,5,7-tetranitro-1,3,5,7-tetrazocine Flow Diagram.

The reactor heel for the hexahydro-1,3,5-trinitro-1,3,5-triazine process contains acetic acid, ammonium nitrate, nitric acid and acetic anhydride. The reactor heel for octahydro-1,3,5,7-tetranitro-1,3,5,7-tetrazocine excludes ammonium nitrate and nitric acid. The reagents for the reaction are added concurrently via three feed streams; 1.) a solution of 1,3,5,7-tetraazatricyclo[3.3.1.1$^{3,7}$]decane in acetic acid, 2.) a solution of ammonium nitrate in nitric acid, and 3.) acetic anhydride. Upon complete addition of the feed streams, the resultant slurry is aged at a prescribed temperature for 45 minutes (hexahydro-1,3,5-trinitro-1,3,5-triazine: 65° C.; octahydro-1,3,5,7-tetranitro-1,3,5,7-tetrazocine: 44° C.) followed by quenching of the excess acetic anhydride with water to approximately 35 wt % water (20 wt % for octahydro-1,3,5,7-tetranitro-1,3,5,7-tetrazocine). The aqueous/acetic acid slurry is heated to 98-100° C. for a prescribed time (hexahydro-1,3,5-trinitro-1,3,5-triazine: 30 min.; octahydro-1,3,5,7-tetranitro-1,3,5,7-tetrazocine: 120 min.), followed by cooling and filtering. The crude product solids are dried and recrystallized. The aqueous spent acid is sent to evaporators to remove the nonvolatile components, such as the hexahydro-1,3,5-trinitro-1,3,5-triazine, octahydro-1,3,5, 7-tetranitro-1,3,5,7-tetrazocine, ammonium nitrate, remaining linear nitramines, various acetamides/formamides, various diamides/mixed formamides, and other products and biproducts. The resulting spent acid stream is then distilled to separate the water and methanoic acid from the spent acid stream to produce glacial acetic acid to complete the process cycle. A portion of the distilled glacial acetic acid is directed to ketene furnaces to regenerate the dehydrating agent acetic anhydride. The process requires the entire volume of glacial acetic acid be derived from the spent acetic acid recovered from the nitrolysis reactions.

The inclusion of methanoic acid as a minor component in a water acetic acid mixture transforms a simple, economically viable distillation step into a more complicated, resource intensive process. If a distillation facility is not specifically designed to accommodate a feed stream of acetic acid and water with approximately 0.25-0.50 wt % methanoic acid, process difficulties are likely to arise. When such process problems have been encountered to date with an inadequate distillation design, the solutions to the problem have resulted in dramatically increased energy usage, reduced glacial acetic acid output and rapid corrosion of the distillation columns requiring increased maintenance and downtimes.

Although patents and the scientific literature disclose processes for the preparation of hexahydro-1,3,5-trinitro-1, 3,5-triazine and octahydro-1,3,5,7-tetranitro-1,3,5,7-tetrazocine, these disclosed processes have limitations and disadvantages.

According to U.S. Pat. No. 4,163,845, "Recycle of Spent Acid in Nitrolysis of 1,3,5,7-Tetraazatricyclo[3.3.1.1$^{3,7}$]decane to hexahydro-1,3,5-trinitro-1,3,5-triazine" by Brumley et al., West German Pat, No. 1939541 ("Octahydro-1,3,5,7-tetranitro-1,3,5,7-tetrazocine from 1,3,5,7-Tetraazatricyclo [3.3.1.1$^{3,7}$]decane by a Simplified—Nitration Process" by PRB NV) and French Pat. No. 2053804 ("Octahydro-1,3,5, 7-tetranitro-1,3,5,7-tetrazocine Production Without Dilution of Reaction Mixture—Reaction Mixture" by France Etat) both relate to the production of Octahydro-1,3,5,7-tetranitro-1,3,5,7-tetrazocine and disclose heating of the reaction mass, after nitrolysis without dissolution with water, to destroy by-products and recycling of the resulting spent acid. However, the French patent distills the spent acid to recover its content of acetic acid, which has been separated from Octahydro-1,3,5,7-tetranitro-1,3,5,7-tetrazocine and Hexahydro-1,3,5-trinitro-1,3,5-triazine, while the German patent recycles the spent acid which apparently still contains excess nitric acid and acetic anhydride. Even though the Octahydro-1,3,5,7-tetranitro-1,3,5,7-tetrazocine nitrolysis and Hexahydro-1,3,5-trinitro-1,3,5-thiazine nitrolysis employ the same reagents, these processes are very different, since the proportions of the reagents, reaction temperatures, reaction mechanisms and precursors and by-product nitramines are significantly different.

U.S. Pat. No. 4,163,845, relating to the production of hexahydro-1,3,5-trinitro-1,3,5-triazine, discloses treating the reaction slurry following the nitrolysis age step with sufficient water to quench the excess acetic anhydride and produce a slurry with 1-2 wt % water content. However, there is no disclosure of an acetic acid recycling step run with 0% water, and according to the disclosure only the solubility of the RDX is determined in acetic acid with 0% water. The resulting slurry is heated to 90-100° C. until the linear nitramines are destroyed. The heating of the 1-2 wt % water slurry to 90-100° C. with nitric acid and linear nitramines present, produces the undesired methanoic acid side product present in the spent acid. The cooled filtrate is either used directly, dehydrated to 0% water via acetic anhydride titration, or the excess nitric acid is neutralized before proceeding with various experiments. Experiments investigating the recycling of the 1.0 wt % aqueous spent acid to the 1,3,5,7-tetraazatricyclo[3.3.1.1$^{3,7}$]decane dissolution step show minimal impact on hexahydro-1,3,5-trinitro-1,3,5-triazine yield. Experiments investigating recycling 1.0 and 2.0 wt % aqueous spent acid which is dehydrated with the appropriate quantity of acetic anhydride prior to the 1,3,5,7-tetraazatricyclo[3.3.1.1$^{3,7}$]decane dissolution step, show a 23% decrease in hexahydro-1,3,5-trinitro-1,3,5-triazine yield. The reference discloses that initially the experiments were run with non-neutralized spent acid recycled to the hexamine solution. However, recycling would not be done on an industrial scale, because it would initiate a highly exothermic process in a vessel that is not engineered for excess heat removal. The potential for a runaway reaction would be significant. Experiments directed toward neutralizing the excess nitric acid with sodium acetate in the spent acid prior to the dissolution of 1,3,5,7-tetraazatricyclo[3.3.1.1$^{3,7}$]decane show a 17% decrease in hexahydro-1,3,5-trinitro-1,3,5-triazine yield. Experiments directed toward neutralizing the excess nitric acid in the spent acid used in both the 1,3,5,7-tetraazatricyclo[3.3.1.1$^{3,7}$]decane dissolution step and formation of the nitrolysis heel, show a 36% decrease in hexahydro-1,3,5-trinitro-1,3,5-triazine yield. The presence of sodium nitrate (nitric acid ion exchange with sodium acetate) in subsequent recycled heels and the hexamine feed streams has a deleterious impact on RDX yield and product distribution. The impact of recycling spent acid on the formation of methanoic acid is not disclosed.

Furthermore, it appears the experiments were run with non-neutralized spent acid recycled to the hexamine solution. This would not be done on industrial scale, neutralization is done with sodium acetate, which has the effect of forwarding sodium nitrate to the subsequent nitration batches. A mixture of sodium nitrate and ammonium nitrate, as opposed to a standard reaction mixture with only ammonium nitrate, is a fundamentally different reaction medium, thus the decreased yields. This effect is magnified when you recycle the sodium acetate neutralized spent acid to both the hexamine dissolution and the nitration heel. From 17% to 36% reduction in yield. Also, the impact of recycling spent acid on the removal of linear nitramines sufficient to meet Military Specifications is not disclosed.

U.S. Pat. No. 4,086,228 "Process for Preparing Octahydro-1,3,5,7-tetranitro-1,3,5,7-tetrazocine" by Solomon, et al related to an improved octahydro-1,3,5,7-tetranitro-1,3,5,7-tetrazocine process and discloses adding 1,3,5,7-tetraazatricyclo[3.3.1.1$^{3,7}$]decane to the heel prior to commencing the nitrolysis step in the conventional process. The amount of 1,3,5,7-tetraazatricyclo[3.3.1.1$^{3,7}$]decane added to the heel prior to commencing the addition of the 3 Feed Streams is equal to 20-25% of that which is eventually added via the 1,3,5,7-tetraazatricyclo[3.3.1.1$^{3,7}$]decane/acetic acid Feed Stream. The total 1,3,5,7-tetraazatricyclo[3.3.1.1$^{3,7}$]decane addition equating to 120-125%. This process adjustment succeeds in increasing the overall octahydro-1,3,5,7-tetranitro-1,3,5,7-tetrazocine yield by 24%. This process adjustment also increases the hexahydro-1,3,5-trinitro-1,3,5-triazine yield in the reaction to approximately 12% relative to octahydro-1,3,5,7-tetranitro-1,3,5,7-tetrazocine. The conventional octahydro-1,3,5,7-tetranitro-1,3,5,7-tetrazocine process produces hexahydro-1,3,5-trinitro-1,3,5-triazine as a side product which does not typically exceed 2% relative to octahydro-1,3,5,7-tetranitro-1,3,5,7-tetrazocine because purging the hexahydro-1,3,5-trinitro-1,3,5-triazine side product above 2% relative is not economically viable. The prior art does not disclose a method for purging the excess hexahydro-1,3,5-trinitro-1,3,5-triazine from octahydro-1,3,5,7-tetranitro-1,3,5,7-tetrazocine.

The present invention therefore provides processes for the preparation of hexahydro-1,3,5-trinitro-1,3,5-triazine and octahydro-1,3,5,7-tetranitro-1,3,5,7-tetrazocine that overcome the disadvantages of earlier processes.

SUMMARY OF THE INVENTION

The present invention provides improved nitrolysis processes for making hexahydro-1,3,5-trinitro-1,3,5-triazine and octahydro-1,3,5,7-tetranitro-1,3,5,7-tetrazocine that are substantially-free of methanoic acid. By substantially free is meant that there is little or no methanoic acid that is detectable by conventional analytical methods. The typical RDX waste stream is 0.15-0.20 wt % formic acid. The typical HMX waste stream is 0.35-0.45 wt %. Generally, the formic acid is reduced from the conventional processes by ≥90%. For example, in some embodiments of the processes of the present invention with respect to RDX, the residual methanoic acid is below about 0.02% by weight. For example, in some embodiments of the processes of the present invention with respect to HMX, the residual methanoic acid is below about 0.045% by weight. Although a definitive lower range of residual methanoic acid is not necessarily defined, a targeted amount can be on the order of 0.01% or less or essentially below the level of detection of analytical methods normally employed.

In further aspects of the invention, the process conditions include:

a). following the nitrolysis age step, quenching the nitrolysis step with water to −0.0-0.50 weight percent acetic anhydride;

b). avoidance of a simmer step;

c). neutralizing the excess nitric acid with ammonia or ammonium acetate);

d). filtering the solid hexahydro-1,3,5-trinitro-1,3,5-triazine or the solid octahydro-1,3,5,7-tetranitro-1,3,5,7-tetrazocine, residual linear nitramines, and residual ammonium nitrate, and recovering virgin ANsol (ammonium nitrate solution) from the filtered solids with a hot water wash;

e). directing the neutralized, anhydrous spent acid to the dissolution of 1,3,5,7-tetraazatricyclo[3.3.1.13,7]decane and the heel of the successive nitrolysis batch, or, alternatively, directing the spent acid to the evaporators before employing the processed acid toward dissolution of 1,3,5,7-tetraazatricyclo[3.3.1.13,7]decane and creation of a heel for a successive nitrolysis batch; and f). slurrying of crude hexahydro-1,3,5-trinitro-1,3,5-triazine or crude octahydro-1,3,5,7-tetranitro-1,3,5,7-tetrazocine in hot 0.0-90 nitric acid, and recrystallizing the filtered solids via the legacy Bachmann process to yield product free of linear nitramines and meeting Military Specification.

In further aspects of the invention, residual acetic anhydride is recovered for recycling back into the process.

In further embodiments the present comprises a methanoic acid free process for producing hexahydro-1,3,5-trinitro-1,3,5-triazine (RDX), by nitrolysis of 1,3,5,7-tetraazatricyclo[3.3.1.1$^{3,7}$]decane.

In further embodiments the present invention provides a methanoic acid free process for producing hexahydro-1,3,5-trinitro-1,3,5-triazine, by nitrolysis of 1,3,5,7-tetraazatricyclo[3.3.1.1$^{3,7}$]decane, comprising:

(a) while maintaining a temperature of about 40-80° C., concurrently introducing a stream of 1,3,5,7-tetraaza-tricyclo[3.3.1.1³,⁷]decane in acetic acid (Feed Stream 1), a stream of ammonium nitrate in nitric acid (Feed Stream 2), and a stream of acetic anhydride (Feed Stream 3) into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine.

In further embodiments the present invention provides a methanoic acid free process for producing hexahydro-1,3,5-trinitro-1,3,5-triazine, by nitrolysis of 1,3,5,7-tetraazatricyclo[3.3.1.1³,⁷]decane, comprising:

(a) while maintaining a temperature of about 40-80° C., concurrently introducing a stream of 1,3,5,7-tetraaza-tricyclo[3.3.1.1³,⁷]decane in acetic acid (Feed Stream 1), a stream of ammonium nitrate in nitric acid (Feed Stream 2), and a stream of acetic anhydride (Feed Stream 3) into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine; and (b) (age stage; indicating aging of the mixture) maintaining the resulting slurry at about 40-80° C. for about 45 minutes (also referred to as the age step for the indicated time period) to affect nitrolysis of the 1,3,5,7-tetraazatricyclo[3.3.1.1³,⁷]decane to produce a slurry containing hexahydro-1,3,5-trinitro-1,3,5-triazine and a spent acid mixture containing acetic acid, acetic anhydride, nitric acid, and ammonium nitrate, or alternatively, adding a quantity of nitric acid (0.0-2.0 equivalents relative to the amount of hexamine added in Feed Stream 1) at 0-15 minutes of the 45 minutes age step, or at 15-30 minutes of the 45 minutes age step, or at 30-45 minutes of the 45 minutes age step.

In further embodiment the present invention provides a methanoic acid free process for producing hexahydro-1,3,5-trinitro-1,3,5-triazine, by nitrolysis of 1,3,5,7-tetraazatricyclo[3.3.1.1³,⁷]decane, comprising:

(a) while maintaining a temperature of about 40-80° C., concurrently introducing a stream of 1,3,5,7-tetraaza-tricyclo[3.3.1.1³,⁷]decane in acetic acid (Feed Stream 1), a stream of ammonium nitrate in nitric acid (Feed Stream 2), and a stream of acetic anhydride (Feed Stream 3) into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1³,⁷]decane to produce a slurry containing hexahydro-1,3,5-trinitro-1,3,5-triazine and a spent acid mixture containing acetic acid, acetic anhydride, nitric acid, and ammonium nitrate, or alternatively, adding a quantity of nitric acid (0.0-2.0 equivalents relative to the amount of hexamine added in Feed Stream 1) at 0-15 minutes of the 45 minutes age step, or at 15-30 minutes of the 45 minutes age step, or at 30-45 minutes of the 45 minutes age step; and (c) adding ammonia or an ammonia source to the slurry of step (b) sufficient to neutralize the nitric acid.

In further embodiments, the present invention provides a methanoic acid free process for producing hexahydro-1,3,5-trinitro-1,3,5-triazine, by nitrolysis of 1,3,5,7-tetraazatri-cyclo[3.3.1.1³,⁷]decane, comprising:

(a) while maintaining a temperature of about 40-80° C., concurrently introducing a stream of 1,3,5,7-tetraaza-tricyclo[3.3.1.1³,⁷]decane in acetic acid (Feed Stream 1), a stream of ammonium nitrate in nitric acid (Feed Stream 2), and a stream of acetic anhydride (Feed Stream 3) into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1³,⁷]decane to produce a slurry containing hexahydro-1,3,5-trinitro-1,3,5-triazine and a spent acid mixture containing acetic acid, acetic anhydride, nitric acid, and ammonium nitrate;

(c) adding ammonia or an ammonia source to the slurry of step (b) sufficient to neutralize the nitric acid; and (d) quenching the neutralized slurry of step (c) with water to produce an anhydrous spent acid mixture containing about 0.0-10 wt % acetic anhydride.

In further embodiments the present invention provides a methanoic acid free process for producing hexahydro-1,3,5-trinitro-1,3,5-triazine, by nitrolysis of 1,3,5,7-tetraazatri-cyclo[3.3.1.1³,⁷]decane, comprising:

(a) while maintaining a temperature of about 40-80° C., concurrently introducing a stream of 1,3,5,7-tetraaza-tricyclo[3.3.1.1³,⁷]decane in acetic acid (Feed Stream 1), a stream of ammonium nitrate in nitric acid (Feed Stream 2), and a stream of acetic anhydride (Feed Stream 3) into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1³,⁷]decane to produce a slurry containing hexahydro-1,3,5-trinitro-1,3,5-triazine and a spent acid mixture containing acetic acid, acetic anhydride, nitric acid, and ammonium nitrate, or alternatively, adding a quantity of nitric acid (0.0-2.0 equivalents relative to the amount of hexamine added in Feed Stream 1) at 0-15 minutes of the 45 minutes age step, or at 15-30 minutes of the 45 minutes age step, or at 30-45 minutes of the 45 minutes age step;

(c) adding ammonia or an ammonia source to the slurry of step (b) sufficient to neutralize the nitric acid;

(d) quenching the neutralized slurry of step (c) with water to produce an anhydrous spent acid mixture containing about 0.0-10 wt % acetic anhydride; and (e) separating the hexahydro-1,3,5-trinitro-1,3,5-triazine and the ammonium nitrate from the anhydrous spent acid mixture of step (d).

In further embodiments the present invention provides a methanoic acid free process for producing hexahydro-1,3,5-trinitro-1,3,5-triazine, by nitrolysis of 1,3,5,7-tetraazatri-cyclo[3.3.1.1³,⁷]decane, comprising:

(a) while maintaining a temperature of about 40-80° C., concurrently introducing a stream of 1,3,5,7-tetraaza-tricyclo[3.3.1.1³,⁷]decane in acetic acid (Feed Stream 1), a stream of ammonium nitrate in nitric acid (Feed Stream 2), and a stream of acetic anhydride (Feed Stream 3) into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1$^{3,7}$]decane to produce a slurry containing hexahydro-1,3,5-trinitro-1,3,5-triazine and a spent acid mixture containing acetic acid, acetic anhydride, nitric acid, and ammonium nitrate, or alternatively, adding a quantity of nitric acid (0.0-2.0 equivalents relative to the amount of hexamine added in Feed Stream 1) at 0-15 minutes of the 45 minutes age step, or at 15-30 minutes of the 45 minutes age step, or at 30-45 minutes of the 45 minutes age step;

(c) adding ammonia or an ammonia source to the slurry of step (b) sufficient to neutralize the nitric acid;

(d) quenching the neutralized slurry of step (c) with water to produce an anhydrous spent acid mixture containing about 0.0-10 wt % acetic anhydride;

(e) separating the hexahydro-1,3,5-trinitro-1,3,5-triazine and the ammonium nitrate from the anhydrous spent acid mixture of step (d); and (f) stirring the hexahydro-1,3,5-trinitro-1,3,5-triazine from step (e) in a 0.0-90 wt % nitric acid solution at reflux to destroy undesired linear nitramines to provide crude hexahydro-1,3,5-trinitro-1,3,5-triazine.

In further embodiments the present invention provides a methanoic acid free process for producing hexahydro-1,3,5-trinitro-1,3,5-triazine, by nitrolysis of 1,3,5,7-tetraazatricyclo[3.3.1.1$^{3,7}$]decane, comprising:

(a) while maintaining a temperature of about 40-80° C., concurrently introducing a stream of 1,3,5,7-tetraazatricyclo[3.3.1.1$^{3,7}$]decane in acetic acid (Feed Stream 1), a stream of ammonium nitrate in nitric acid (Feed Stream 2), and a stream of acetic anhydride (Feed Stream 3) into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1$^{3,7}$]decane to produce a slurry containing hexahydro-1,3,5-trinitro-1,3,5-triazine and a spent acid mixture containing acetic acid, acetic anhydride, nitric acid, and ammonium nitrate, or alternatively, adding a quantity of nitric acid (0.0-2.0 equivalents relative to the amount of hexamine added in Feed Stream 1) at 0-15 minutes of the 45 minutes age step, or at 15-30 minutes of the 45 minutes age step, or at 30-45 minutes of the 45 minutes age step;

(c) adding ammonia or an ammonia source to the slurry of step (b) sufficient to neutralize the nitric acid;

(d) quenching the neutralized slurry of step (c) with water to produce an anhydrous spent acid mixture containing about 0.0-10 wt % acetic anhydride;

(e) separating the hexahydro-1,3,5-trinitro-1,3,5-triazine and the ammonium nitrate from the anhydrous spent acid mixture of step (d);

(f) stirring the hexahydro-1,3,5-trinitro-1,3,5-triazine from step (e) in a 0.0-90 wt % nitric acid solution at reflux to destroy undesired linear nitramines to provide crude hexahydro-1,3,5-trinitro-1,3,5-triazine; and (g) collecting the crude hexahydro-1,3,5-trinitro-1,3,5-triazine from step (f) by filtration.

In further embodiments, the present invention provides for a methanoic acid free process for producing hexahydro-1,3,5-trinitro-1,3,5-triazine, by nitrolysis of 1,3,5,7-tetraazatricyclo[3.3.1.1$^{3,7}$]decane, comprising any one of, or any combination of two or more of the following steps (a) through (g):

(a) while maintaining a temperature of about 40-80° C., concurrently introducing a stream of 1,3,5,7-tetraazatricyclo[3.3.1.1$^{3,7}$]decane in acetic acid, a stream of ammonium nitrate in nitric acid, and a stream of acetic anhydride into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1$^{3,7}$]decane to produce a slurry containing hexahydro-1,3,5-trinitro-1,3,5-triazine and a spent acid mixture containing acetic acid, acetic anhydride, nitric acid, and ammonium nitrate;

(c) adding ammonia or an ammonia source to the slurry of step (b) sufficient to neutralize the nitric acid;

(d) quenching the neutralized slurry of step (c) with water to produce an anhydrous spent acid mixture containing about 0.0-10 wt % acetic anhydride;

(e) separating the hexahydro-1,3,5-trinitro-1,3,5-triazine and the ammonium nitrate from the anhydrous spent acid mixture of step (d);

(f) stirring the hexahydro-1,3,5-trinitro-1,3,5-triazine from step (e) in a 0.0-90 wt % nitric acid solution at reflux to destroy undesired linear nitramines to provide crude hexahydro-1,3,5-trinitro-1,3,5-triazine; and (g) collecting the crude hexahydro-1,3,5-trinitro-1,3,5-triazine from step (f) by filtration.

In further embodiments the present invention provides a process comprising the further step of washing the hexahydro1,3,5-trinitro-1,3,5-triazine and ammonium nitrate separated from step (e) with hot water to produce washed hexahydro1,3,5-trinitro-1,3,5-triazine prior to proceeding to step (f).

In further embodiments the present invention provides a process comprising the further step (h) of washing the crude hexahydro-1,3,5-trinitro-1,3,5-triazine from step (g with water.

In further embodiments the present invention provides a process comprising the further step (i) or the further step (j) of recrystallizing the washed or unwashed hexahydro-1,3,5-trinitro-1,3,5-triazine from step (h) or from step (g), respectively.

In further embodiments the present invention provides a process wherein the recrystallization is from a solvent selected from the group consisting of acetone, cyclohexanone, water, dimethyl sulfoxide (DMSO), dimethylformamide (DMF), dimethyacetamide (DMAc), N-methylpyrrolidone (NMP), 2-Methylcyclohexanone, cyclohexyne, formamide, γ-butyrolactone, γ-valerolactone, δ-valerolactone, ε-caprolactone, and mixtures thereof.

In further embodiments the present invention provides a process wherein the recrystallization solvent is a mixture of cyclohexanone and acetone In further embodiments the present invention provides a process wherein the ammonia source of step (c) is ammonium acetate.

In further embodiments the present invention provides a process wherein step (c) is performed by first cooling the slurry to about 20-60° C. prior to adding the ammonia or ammonia source.

In further embodiments the present invention provides a process wherein step (c) is performed by first cooling the slurry to about 25-55° C. prior to adding the ammonia or ammonia source.

In further embodiments the present invention provides a process wherein step (c) is performed by first cooling the slurry to about 45° C. prior to adding the ammonia or ammonia source.

In further embodiments the present invention provides a process wherein in step (f) the mixture is subsequently cooled to about 10-60° C. prior to filtration.

In further embodiments the present invention provides a process wherein in step (f) the mixture is subsequently cooled to about 20-50° C. prior to filtration.

In further embodiments the present invention provides a process wherein in step (f) the mixture is subsequently cooled to about 25° C. prior to filtration.

In further embodiments the present invention provides a process wherein in step (a) the temperature is maintained at about 50-75° C.

In further embodiments the present invention provides a process wherein in step (a) the temperature is maintained at about 65° C.

In further embodiments the present invention provides a process wherein in step (b) the slurry is maintained at about 50-75° C.

In further embodiments the present invention provides a process wherein in step (b) the slurry is maintained at about 65° C.

In further embodiments the present invention provides a process wherein in step (d) the quenching of the neutralized slurry of step (c) with water is conducted to produce an anhydrous spent acid mixture containing about 0.0-5 wt % acetic anhydride.

In further embodiments the present invention provides a process wherein in step (d) the quenching of the neutralized slurry of step (c) with water is conducted to produce an anhydrous spent acid mixture containing about 0.0-0.5 wt % acetic anhydride.

In further embodiments the present invention provides a process wherein in step (f) the washed or unwashed hexahydro-1,3,5-trinitro-1,3,5-triazine from step (e) is stirred in about 0-60 wt % nitric acid solution.

In further embodiments the present invention provides a process wherein in step (f) the washed or unwashed hexahydro-1,3,5-trinitro-1,3,5-triazine from step (e) is stirred in about 0-40 wt % nitric acid solution.

In further embodiments the present invention provides a process wherein in step (f) the washed or unwashed hexahydro-1,3,5-trinitro-1,3,5-triazine from step (e) is stirred in about 0-10 wt % nitric acid solution.

In further embodiments the present invention provides a process wherein at least a portion of the anhydrous spent acid mixture from step (e) is directly recycled.

In further embodiments the present invention provides a process wherein a portion of the anhydrous spent acid mixture from step (e) is directly recycled via at least one of the following three means:

(i) recycled to the heel, (ii) recycled to dissolve the 1,3,5,7-tetraazatricyclo[3.3.1.1$^{3,7}$]decane, and/or (iv) recycled through pre-distillation evaporators to provide acetic acid and a slurry of acetic acid, RDX, ammonium nitrate and trace impurities.

In further embodiments the present invention provides a process wherein the portion of the anhydrous spent acid mixture from step (e) that is directly recycled through pre-distillation evaporators is followed by conversion of the acetic acid obtained therefrom to acetic anhydride in a ketene furnace.

In further embodiments the present invention provides a process wherein the slurry from pre-distillation evaporator is collected and recycled to the crude hexahydro-1,3,5-trinitro-1,3,5-triazine filtration step (e) from subsequent batches.

In further embodiments the present invention provides a process wherein the ammonium nitrate content in the 1,3,5,7-tetraazatricyclo[3.3.1.1$^{3,7}$]decane feed stream and/or the acetic acid in the heel are determined and the ammonium nitrate content of the composition of the heel is adjusted based on the determinations to ensure that the ammonium nitrate concentration is returned to that of the starting, standard heel concentration.

In further embodiments the present invention provides a process wherein the resultant aqueous filtrate from step (f) is collected and recycled through pre-distillation evaporators followed by azeotropic distillation.

In further embodiments the present invention provides a methanoic acid free no quench process, i.e. without a quenching step, for producing hexahydro-1,3,5-trinitro-1,3,5-triazine, by nitrolysis of 1,3,5,7-tetraazatricyclo[3.3.1.1$^{3,7}$]decane, comprising:

(a) while maintaining a temperature of about 40-80° C., concurrently introducing a stream of 1,3,5,7-tetraazatricyclo[3.3.1.1$^{3,7}$]decane in acetic acid (Feed Stream 1), a stream of ammonium nitrate in nitric acid (Feed Stream 2), and a stream of acetic anhydride (Feed Stream 3) into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1$^{3,7}$]decane to produce a slurry containing hexahydro-1,3,5-trinitro-1,3,5-triazine and a spent acid mixture containing acetic acid, acetic anhydride, nitric acid, and ammonium nitrate, or alternatively, adding a quantity of nitric acid (0.0-2.0 equivalents relative to the amount of hexamine added in Feed Stream 1) at 0-15 minutes of the 45 minutes age step, or at 15-30 minutes of the 45 minutes age step, or at 30-45 minutes of the 45 minutes age step;

(c) adding ammonia or an ammonia source to the slurry of step (b) sufficient to neutralize the nitric acid;

(d) separating the hexahydro-1,3,5-trinitro-1,3,5-triazine and the ammonium nitrate from the anhydrous spent acid mixture of step (c);

(e) stirring the hexahydro-1,3,5-trinitro-1,3,5-triazine from step (d) in a 0.0-90 wt % nitric acid solution at reflux to destroy undesired linear nitramines to provide crude hexahydro-1,3,5-trinitro-1,3,5-triazine; and (f) collecting the crude hexahydro-1,3,5-trinitro-1,3,5-triazine from step (e) by filtration.

In further embodiments, the present invention provides for a methanoic acid free process for producing hexahydro-1,3,5-trinitro-1,3,5-triazine, by nitrolysis of 1,3,5,7-tetraazatricyclo[3.3.1.1$^{3,7}$]decane, comprising any one of, or any combination of two or more of the following steps (a) through (f):

(a) while maintaining a temperature of about 40-80° C., concurrently introducing a stream of 1,3,5,7-tetraazatricyclo[3.3.1.1$^{3,7}$]decane in acetic acid, a stream of ammonium nitrate in nitric acid, and a stream of acetic anhydride into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1$^{3,7}$]decane to produce a slurry containing hexahydro-1,3,5-trinitro-1,3,5-triazine and a spent acid mixture containing acetic acid, acetic anhydride, nitric acid, and ammonium nitrate;

(c) adding ammonia or an ammonia source to the slurry of step (b) sufficient to neutralize the nitric acid;

(d) separating the hexahydro-1,3,5-trinitro-1,3,5-triazine and the ammonium nitrate from the anhydrous spent acid mixture of step (c);

(e) stirring the hexahydro-1,3,5-trinitro-1,3,5-triazine from step (d) in a 0.0-90 wt % nitric acid solution at reflux to destroy undesired linear nitramines to provide crude hexahydro-1,3,5-trinitro-1,3,5-triazine; and (f) collecting the crude hexahydro-1,3,5-trinitro-1,3,5-triazine from step (e) by filtration.

In further embodiments the present invention provides a methanoic acid free no quench process comprising the further step of washing the hexahydro1,3,5-trinitro-1,3,5-triazine and ammonium nitrate separated from step (d) with hot water to produce washed hexahydro1,3,5-trinitro-1,3,5-triazine prior to proceeding to step (e).

In further embodiments the present invention provides a methanoic acid free no quench process comprising the further step (g) of washing the crude hexahydro-1,3,5-trinitro-1,3,5-triazine from step (f) is washed with water.

In further embodiments the present invention provides a methanoic acid free no quench process comprising the further step (h) or the further step (i) of recrystallizing the washed, or unwashed hexahydro-1,3,5-trinitro-1,3,5-triazine from step (g) or from step (f), respectively.

In further embodiments the present invention provides a methanoic acid free no quench process wherein the recrystallization is from a solvent selected from the group consisting of acetone, cyclohexanone, water, dimethyl sulfoxide (DMSO), dimethylformamide (DMF), dimethyacetamide (DMAc), N-methylpyrrolidone (NMP), 2-Methylcyclohexanone, cyclohexyne, formamide, γ-butyrolactone, γ-valerolactone, δ-valerolactone, ε-caprolactone, and mixtures thereof.

In further embodiments the present invention provides a methanoic acid free no quench process wherein the recrystallization solvent is a mixture of cyclohexanone and acetone In further embodiments the present invention provides a methanoic acid free no quench process wherein the ammonia source of step (c) is ammonium acetate.

In further embodiments the present invention provides a methanoic acid free no quench process wherein step (c) is performed by first cooling the slurry to about 20-60° C. prior to adding the ammonia or ammonia source.

In further embodiments the present invention provides a methanoic acid free no quench process wherein step (c) is performed by first cooling the slurry to about 25-55° C. prior to adding the ammonia or ammonia source.

In further embodiments the present invention provides a methanoic acid free no quench process wherein step (c) is performed by first cooling the slurry to about 45° C. prior to adding the ammonia or ammonia source.

In further embodiments the present invention provides a methanoic acid free no quench process wherein in step (d) the mixture is subsequently cooled to about 10-60° C. prior to filtration.

In further embodiments the present invention provides a methanoic acid free no quench process wherein in step (d) the mixture is subsequently cooled to about 20-50° C. prior to filtration.

In further embodiments the present invention provides a methanoic acid free no quench process wherein in step (d) the mixture is subsequently cooled to about 25° C. prior to filtration.

In further embodiments the present invention provides a methanoic acid free no quench process wherein in step (a) the temperature is maintained at about 50-75° C.

In further embodiments the present invention provides a methanoic acid free no quench process wherein in step (a) the temperature is maintained at about 65° C.

In further embodiments the present invention provides a methanoic acid free no quench process wherein in step (b) the slurry is maintained at about 50-75° C.

In further embodiments the present invention provides a methanoic acid free no quench process wherein in step (b) the slurry is maintained at about 65° C.

In further embodiments the present invention provides a methanoic acid free no quench process wherein in step (e) the washed or unwashed hexahydro-1,3,5-trinitro-1,3,5-triazine from step (d) is stirred in about 0-60 wt % nitric acid solution.

In further embodiments the present invention provides a methanoic acid free no quench process wherein in step (e) the washed or unwashed hexahydro-1,3,5-trinitro-1,3,5-triazine from step (d) is stirred in about 0-40 wt % nitric acid solution.

In further embodiments the present invention provides a methanoic acid free no quench process wherein in step (e) the washed or unwashed hexahydro-1,3,5-trinitro-1,3,5-triazine from step (d) is stirred in about 0-10 wt % nitric acid solution.

In further embodiments the present invention provides a methanoic acid free no quench process wherein at least a portion of the anhydrous spent acid mixture from step (d) is directly recycled.

In further embodiments the present invention provides a methanoic acid free no quench process wherein a portion of the anhydrous spent acid mixture from step (d) is directly recycled via at least one of the following three means:

(i) recycled to the heel, (ii) following quench with water to 0.0-0.50 wt % acetic anhydride, recycled to dissolve the 1,3,5,7-tetraazatricyclo[3.3.1.1$^{3,7}$]decane, and/or (iii) recycled through pre-distillation evaporators to provide solution of acetic acid and acetic anhydride and a slurry of acetic acid, acetic anhydride, hexahydro-1,3,5-trinitro-1,3,5-triazine, ammonium nitrate and trace impurities.

In further embodiments the present invention provides a methanoic acid free no quench process wherein the portion of the anhydrous spent acid mixture from step (d) that is directly recycled through pre-distillation evaporators is followed by azeotropic distillation to separate acetic acid from acetic anhydride.

In further embodiments the present invention provides a methanoic acid free no quench process wherein the slurry from pre-distillation evaporator is collected and recycled to the crude hexahydro-1,3,5-trinitro-1,3,5-triazine filtration step (d) from subsequent batches.

In further embodiments the present invention provides a methanoic acid free no quench process wherein the ammonium nitrate content in the 1,3,5,7-tetraazatricyclo[3.3.1.1$^{3,7}$]decane feed stream is determined and the ammonium nitrate composition of the heel and/or ammonium nitrate/nitric acid feed stream is adjusted based on the determination to ensure the overall ammonium nitrate concentration in the reaction remains the same.

In further embodiments the present invention provides a methanoic acid free no quench process wherein the ammonium nitrate and acetic anhydride content in the acetic acid of the heel is determined and the ammonium nitrate and acetic anhydride content of the heel and/or the acetic anhydride feed stream and/or the ammonium nitrate/nitric acid feed stream is adjusted based on the determination to ensure the overall ammonium nitrate concentration and acetic anhydride concentration in the reaction remains the same.

In further embodiments the present invention provides a methanoic acid free no quench process wherein the resultant aqueous filtrate from step (f) is collected and recycled through pre-distillation evaporators followed by azeotropic distillation.

In further embodiments the present invention provides a methanoic acid free no quench process wherein the portion of the spent acid mixture not directed to the heel is processed via pre-distillation evaporators followed by azeotropic distillation to provide methanoic acid free glacial acetic acid and acetic anhydride.

In further embodiments the present invention provides a methanoic acid free no quench process wherein the acetic anhydride content in the acetic acid in the heel are determined and the acetic anhydride content of the composition of the heel is adjusted based on the determinations to ensure that the acetic anhydride concentration is returned to that of the starting, standard heel concentration.

In further embodiments the present invention provides a methanoic acid free no neutralization process, i.e. without a neutralization step, for producing hexahydro-1,3,5-trinitro-1,3,5-triazine, by nitrolysis of 1,3,5,7-tetraazatricyclo[3.3.1.1$^{3,7}$]decane, comprising:

(a) while maintaining a temperature of about 40-80° C., concurrently introducing a stream of 1,3,5,7-tetraazatricyclo[3.3.1.1$^{3,7}$]decane in acetic acid (Feed Stream 1), a stream of ammonium nitrate in nitric acid (Feed Stream 2), and a stream of acetic anhydride (Feed Stream 3) into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1$^{3,7}$]decane to produce a slurry containing hexahydro-1,3,5-trinitro-1,3,5-triazine and a spent acid mixture containing acetic acid, acetic anhydride, nitric acid, and ammonium nitrate, or alternatively, adding a quantity of nitric acid (0.0-2.0 equivalents relative to the amount of hexamine added in Feed Stream 1) at 0-15 minutes of the 45 minutes age step, or at 15-30 minutes of the 45 minutes age step, or at 30-45 minutes of the 45 minutes age step;

(c) quenching the non-neutralized slurry of step (b) with water to produce an anhydrous spent acid mixture containing about 0.0-10 wt % acetic anhydride;

(d) separating the hexahydro-1,3,5-trinitro-1,3,5-triazine and the ammonium nitrate from the anhydrous spent acid mixture of step (c);

(e) stirring the hexahydro-1,3,5-trinitro-1,3,5-triazine from step (d) in a 0.0-90 wt % nitric acid solution at reflux to destroy undesired linear nitramines to provide crude hexahydro-1,3,5-trinitro-1,3,5-triazine; and (f) collecting the crude hexahydro-1,3,5-trinitro-1,3,5-triazine from step (e) by filtration.

In further embodiments, the present invention provides for a methanoic acid free process for producing hexahydro-1,3,5-trinitro-1,3,5-triazine, by nitrolysis of 1,3,5,7-tetraazatricyclo[3.3.1.1$^{3,7}$]decane, comprising any one of, or any combination of two or more of the following steps (a) through (f):

(a) while maintaining a temperature of about 40-80° C., concurrently introducing a stream of 1,3,5,7-tetraazatricyclo[3.3.1.1$^{3,7}$]decane in acetic acid, a stream of ammonium nitrate in nitric acid, and a stream of acetic anhydride into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1$^{3,7}$]decane to produce a slurry containing hexahydro-1,3,5-trinitro-1,3,5-triazine and a spent acid mixture containing acetic acid, acetic anhydride, nitric acid, and ammonium nitrate;

(c) quenching the non-neutralized slurry of step (b) with water to produce an anhydrous spent acid mixture containing about 0.0-10 wt % acetic anhydride;

(d) separating the hexahydro-1,3,5-trinitro-1,3,5-triazine and the ammonium nitrate from the anhydrous spent acid mixture of step (c);

(e) stirring the hexahydro-1,3,5-trinitro-1,3,5-triazine from step (d) in a 0.0-90 wt % nitric acid solution at reflux to destroy undesired linear nitramines to provide crude hexahydro-1,3,5-trinitro-1,3,5-triazine; and (f) collecting the crude hexahydro-1,3,5-trinitro-1,3,5-triazine from step (e) by filtration.

In further embodiments the present invention provides a methanoic acid free no neutralization process comprising the further step of washing the hexahydro1,3,5-trinitro-1,3,5-triazine and ammonium nitrate separated from step (d) with hot water to produce washed hexahydro1,3,5-tirnitro-1,3,5-triazine prior to proceeding to step (e).

In further embodiments the present invention provides a methanoic acid free no neutralization process comprising the further step (g) of washing the crude hexahydro-1,3,5-trinitro-1,3,5-triazine from step (f) is washed with water.

In further embodiments the present invention provides a methanoic acid free no neutralization process comprising the further step (h) or the further step (i) of recrystallizing the washed, or unwashed hexahydro-1,3,5-trinitro-1,3,5-triazine from step (g) or step (f), respectively.

In further embodiments the present invention provides a methanoic acid free no neutralization process wherein the recrystallization is from a solvent selected from the group consisting of acetone, cyclohexanone, water, dimethyl sulfoxide (DMSO), dimethylformamide (DMF), dimethyacetamide (DMAc), N-methylpyrrolidone (NMP), 2-Methyl-cyclohexanone, cyclohexyne, formamide, γ-butyrolactone, γ-valerolactone, δ-valerolactone, ε-caprolactone, and mixtures thereof.

In further embodiments the present invention provides a methanoic acid free no neutralization process wherein the recrystallization solvent is a mixture of cyclohexanone and acetone In further embodiments the present invention provides a methanoic acid free no neutralization process wherein step (c) is performed by first cooling the slurry to about 20-60° C. prior to adding the water.

In further embodiments the present invention provides a methanoic acid free no neutralization process wherein step (c) is performed by first cooling the slurry to about 25-55° C. prior to adding the water.

In further embodiments the present invention provides a methanoic acid free no neutralization process wherein step (c) is performed by first cooling the slurry to about 45° C. prior to adding the water.

In further embodiments the present invention provides a methanoic acid free no neutralization process wherein in step (f) the mixture is subsequently cooled to about 10-60° C. prior to filtration.

In further embodiments the present invention provides a methanoic acid free no neutralization process wherein in step (f) the mixture is subsequently cooled to about 20-50° C. prior to filtration.

In further embodiments the present invention provides a methanoic acid free no neutralization process wherein in step (f) the mixture is subsequently cooled to about 25° C. prior to filtration.

In further embodiments the present invention provides a methanoic acid free no neutralization process wherein in step (a) the temperature is maintained at about 50-75° C.

In further embodiments the present invention provides a methanoic acid free no neutralization process wherein in step (a) the temperature is maintained at about 65° C.

In further embodiments the present invention provides a methanoic acid free no neutralization process wherein in step (b) the slurry is maintained at about 50-75° C.

In further embodiments the present invention provides a methanoic acid free no neutralization process wherein in step (b) the slurry is maintained at about 65° C.

In further embodiments the present invention provides a methanoic acid free no neutralization process wherein the quenching of the non-neutralized slurry of step (c) with water is conducted to produce an anhydrous spent acid mixture containing about 0.0-5 wt % acetic anhydride.

In further embodiments the present invention provides a methanoic acid free no neutralization process wherein the quenching of the non-neutralized slurry of step (c) with water is conducted to produce an anhydrous spent acid mixture containing about 0.0-0.5 wt % acetic anhydride.

In further embodiments the present invention provides a methanoic acid free no neutralization process wherein in step (e) the washed or unwashed hexahydro-1,3,5-trinitro-1,3,5-triazine from step (d) is stirred in about 0-60 wt % nitric acid solution.

In further embodiments the present invention provides a methanoic acid free no neutralization process wherein in step (e) the washed or unwashed hexahydro-1,3,5-trinitro-1,3,5-triazine from step (d) is stirred in about 0-40 wt % nitric acid solution.

In further embodiments the present invention provides a methanoic acid free no neutralization process wherein in step (e) the washed or unwashed hexahydro-1,3,5-trinitro-1,3,5-triazine from step (d) is stirred in about 0-10 wt % nitric acid solution.

In further embodiments the present invention provides a methanoic acid free no neutralization process wherein at least a portion of the anhydrous spent acid mixture from step (d) is directly recycled.

In further embodiments the present invention provides a methanoic acid free no neutralization process wherein a portion of the anhydrous spent acid mixture from step (d) is directly recycled via at least one of the following three means:

(i) recycled to the heel, (ii) following neutralization with ammonia, recycled to dissolve the 1,3,5,7-tetraazatricyclo[3.3.1.1$^{3,7}$]decane, and/or (iii) following neutralization with ammonia, recycled through pre-distillation evaporators to provide acetic acid and a slurry of acetic acid, hexahydro-1,3,5-trinitro-1,3,5-triazine, ammonium nitrate and trace impurities.

In further embodiments the present invention provides a methanoic acid free no neutralization process wherein the portion of the neutralized, anhydrous spent acid mixture from step (d) that is directly recycled through pre-distillation evaporators is followed by conversion of the acetic acid obtained therefrom to acetic anhydride in a ketene furnace.

In further embodiments the present invention provides a methanoic acid free no neutralization process wherein the slurry from pre-distillation evaporator is collected and recycled to the crude hexahydro-1,3,5-trinitro-1,3,5-triazine filtration step from subsequent batches.

In further embodiments the present invention provides a methanoic acid free no neutralization process wherein the ammonium nitrate content in the 1,3,5,7-tetraazatricyclo [3.3.1.1$^{3,7}$]decane feed stream is determined and the ammonium nitrate composition of the heel and/or ammonium nitrate/nitric acid feed stream is adjusted based on the determination to ensure the overall ammonium nitrate concentration in the reaction remains the same.

In further embodiments the present invention provides a methanoic acid free no neutralization process wherein the ammonium nitrate and nitric acid content in the acetic acid of the heel is determined and the ammonium nitrate and nitric acid content of the heel and/or the ammonium nitrate/nitric acid feed stream is adjusted based on the determination to ensure the overall ammonium nitrate concentration and nitric acid concentration in the reaction remains the same.

In further embodiments the present invention provides a methanoic acid free no neutralization process wherein the resultant aqueous filtrate from step (f) is collected and recycled through pre-distillation evaporators followed by azeotropic distillation.

In further embodiments the present invention provides a methanoic acid free no neutralization process wherein the portion of the spent acid mixture not directed to the heel is neutralized with ammonia and the resultant acetic acid filtrate is processed via pre-distillation evaporators to provide methanoic acid free glacial acetic acid.

In further embodiments the present invention provides both a methanoic acid free no quench and no neutralization process, i.e. without a quenching step and without a neutralization step, for producing hexahydro-1,3,5-trinitro-1,3,5-triazine, by nitrolysis of 1,3,5,7-tetraazatricyclo[3.3.1.1$^{3,7}$]decane, comprising:

(a) while maintaining a temperature of about 40-80° C., concurrently introducing a stream of 1,3,5,7-tetraazatricyclo[3.3.1.1$^{3,7}$]decane in acetic acid (Feed Stream 1), a stream of ammonium nitrate in nitric acid (Feed Stream 2), and a stream of acetic anhydride (Feed Stream 3) into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1$^{3,7}$]decane to produce a slurry containing hexahydro-1,3,5-trinitro-1,3,5-triazine and a spent acid mixture containing acetic acid, acetic anhydride, nitric acid, and ammonium nitrate, or alternatively, adding a quantity of nitric acid (0.0-2.0 equivalents relative to the amount of hexamine added in Feed Stream 1) at 0-15 minutes of the 45 minutes age step, or at 15-30 minutes of the 45 minutes age step, or at 30-45 minutes of the 45 minutes age step;

(c) separating the hexahydro-1,3,5-trinitro-1,3,5-triazine and the ammonium nitrate from the anhydrous spent acid mixture of step (b);

(d) stirring the hexahydro-1,3,5-trinitro-1,3,5-triazine from step (c) in a 0.0-90 wt % nitric acid solution at reflux to destroy undesired linear nitramines to provide crude hexahydro-1,3,5-trinitro-1,3,5-triazine; and (e) collecting the crude hexahydro-1,3,5-trinitro-1,3,5-triazine from step (d) by filtration.

In further embodiments, the present invention provides for a methanoic acid free process for producing hexahydro-1,3,5-trinitro-1,3,5-triazine, by nitrolysis of 1,3,5,7-tetraazatricyclo[3.3.1.1$^{3,7}$]decane, comprising any one of, or any combination of two or more of the following steps (a) through (e):

(a) while maintaining a temperature of about 40-80° C., concurrently introducing a stream of 1,3,5,7-tetraazatricyclo[3.3.1.1$^{3,7}$]decane in acetic acid, a stream of ammonium nitrate in nitric acid, and a stream of acetic anhydride into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1$^{3,7}$]decane to produce a slurry containing hexahydro-1,3,5-trinitro-1,3,5-triazine and a spent acid mixture containing acetic acid, acetic anhydride, nitric acid, and ammonium nitrate;

(c) separating the hexahydro-1,3,5-trinitro-1,3,5-triazine and the ammonium nitrate from the anhydrous spent acid mixture of step (b);

(d) stirring the hexahydro-1,3,5-trinitro-1,3,5-triazine from step (c) in a 0.0-90 wt % nitric acid solution at reflux to destroy undesired linear nitramines to provide crude hexahydro-1,3,5-trinitro-1,3,5-triazine; and (e) collecting the crude hexahydro-1,3,5-trinitro-1,3,5-triazine from step (d) by filtration.

In further embodiments the present invention provides a methanoic acid free no quench and no neutralization process comprising the further step of washing the hexahydro1,3,5-trinitro-1,3,5-triazine and ammonium nitrate separated from step (c) with hot water to produce washed hexahydro1,3,5-tirnitro-1,3,5-triazine prior to proceeding to step (d).

In further embodiments the present invention provides a methanoic acid free no quench and no neutralization process comprising the further step (f of washing the crude hexahydro-1,3,5-trinitro-1,3,5-triazine from step (e) is washed with water.

In further embodiments the present invention provides a methanoic acid free no quench and no neutralization process comprising the further step (g) or the further step (h) of recrystalizing the washed, or unwashed hexahydro-1,3,5-trinitro-1,3,5-triazine from step (f) or from step (e), respectively.

In further embodiments the present invention provides a methanoic acid free no quench and no neutralization process wherein the recrystallization is from a solvent selected from the group consisting of acetone, cyclohexanone, water, dimethyl sulfoxide (DMSO), dimethylformamide (DMF), dimethyacetamide (DMAc), N-methylpyrrolidone (NMP), 2-Methylcyclohexanone, cyclohexyne, formamide, γ-butyrolactone, γ-valerolactone, δ-valerolactone, ε-caprolactone, and mixtures thereof.

In further embodiments the present invention provides a methanoic acid free no quench and no neutralization process wherein the recrystallization solvent is a mixture of cyclohexanone and acetone In further embodiments the present invention provides a methanoic acid free no quench and no neutralization process wherein in step (d) the mixture is subsequently cooled to about 10-60° C. prior to filtration.

In further embodiments the present invention provides a methanoic acid free no quench and no neutralization process wherein in step (d) the mixture is subsequently cooled to about 20-50° C. prior to filtration.

In further embodiments the present invention provides a methanoic acid free no quench and no neutralization process wherein in step (d) the mixture is subsequently cooled to about 25° C. prior to filtration.

In further embodiments the present invention provides a methanoic acid free no quench and no neutralization process wherein in step (a) the temperature is maintained at about 50-75° C.

In further embodiments the present invention provides a methanoic acid free no quench and no neutralization process wherein in step (a) the temperature is maintained at about 65° C.

In further embodiments the present invention provides a methanoic acid free no quench and no neutralization process wherein in step (b) the slurry is maintained at about 50-75° C.

In further embodiments the present invention provides a methanoic acid free no quench and no neutralization process wherein in step (b) the slurry is maintained at about 65° C.

In further embodiments the present invention provides a methanoic acid free no quench and no neutralization process wherein in step (d) the washed or unwashed hexahydro-1,3,5-trinitro-1,3,5-triazine from step (c) is stirred in about 0-60 wt % nitric acid solution.

In further embodiments the present invention provides a methanoic acid free no quench and no neutralization process wherein in step (d) the washed or unwashed hexahydro-1,3,5-trinitro-1,3,5-triazine from step (c) is stirred in about 0-40 wt % nitric acid solution.

In further embodiments the present invention provides a methanoic acid free no quench and no neutralization process wherein in step (d) the washed or unwashed hexahydro-1,3,5-trinitro-1,3,5-triazine from step (c) is stirred in about 0-10 wt % nitric acid solution.

In further embodiments the present invention provides a methanoic acid free no quench and no neutralization process wherein at least a portion of the anhydrous, non-neutralized spent acid mixture from step (c) is directly recycled.

In further embodiments the present invention provides a methanoic acid free no quench and no neutralization process wherein a portion of the anhydrous, non-neutralized spent acid mixture from step (c) is directly recycled via at least one of the following three means:

(I) recycled to the heel, (II) following neutralization with ammonia and quenching the acetic anhydride with water to 0.0-0.50 wt % acetic anhydride, recycled to dissolve the 1,3,5,7-tetraazatricyclo[3.3.1.1$^{3,7}$]decane, and/or (III) following neutralization with ammonia, recycled through pre-distillation evaporators to provide a solution of acetic acid and acetic anhydride and a slurry of acetic acid, acetic anhydride, hexahydro-1,3,5-trinitro-1,3,5-triazine, ammonium nitrate and trace impurities.

In further embodiments the present invention provides a methanoic acid free no quench and no neutralization process wherein the portion of the anhydrous, neutralized spent acid mixture from step (c) that is directly recycled through pre-distillation evaporators is followed by azeotropic distillation to separate acetic acid from acetic anhydride.

In further embodiments the present invention provides a methanoic acid free no quench and no neutralization process wherein the slurry from pre-distillation evaporator is collected and recycled to the crude hexahydro-1,3,5-trinitro-1,3,5-triazine filtration step from subsequent batches.

In further embodiments the present invention provides a methanoic acid free no quench and no neutralization process wherein the ammonium nitrate content in the 1,3,5,7-tetraazatricyclo[3.3.1.1$^{3,7}$]decane feed stream is determined and the ammonium nitrate composition of the heel and/or ammonium nitrate/nitric acid feed stream is adjusted based on the determination to ensure the overall ammonium nitrate concentration in the reaction remains the same.

In further embodiments the present invention provides a methanoic acid free no quench and no neutralization process wherein the ammonium nitrate, nitric acid and acetic anhydride content in the acetic acid of the heel is determined and the ammonium nitrate, nitric acid and acetic anhydride content of the heel and/or the ammonium nitrate/nitric acid feed stream and/or the acetic anhydride feed stream is adjusted based on the determination to ensure the overall ammonium nitrate concentration and nitric acid concentration and acetic anhydride concentration in the reaction remains the same.

In further embodiments the present invention provides a methanoic acid free no quench and no neutralization process wherein the resultant aqueous filtrate from step (f) is collected and recycled through pre-distillation evaporators followed by azeotropic distillation.

In further embodiments the present invention provides a methanoic acid free no quench and no neutralization process wherein the portion of the spent acid mixture not directed to the heel is neutralized with ammonia and the resultant acetic acid/acetic anhydride filtrate is processed via pre-distillation evaporators followed by azeotropic distillation to provide methanoic acid free glacial acetic acid and acetic anhydride.

In further embodiments, the present invention provides a methanoic acid free process with a quench to about 0-35 wt % aqueous acetic acid for producing hexahydro-1,3,5-trinitro-1,3,5-triazine, by nitrolysis of 1,3,5,7-tetraazatricyclo[3.3.1.1$^{3,7}$]decane, comprising:

(a) while maintaining a temperature of about 40-80° C., concurrently introducing a stream of 1,3,5,7-tetraazatricyclo[3.3.1.1$^{3,7}$]decane in acetic acid (Feed Stream 1), a stream of ammonium nitrate in nitric acid (Feed Stream 2), and a stream of acetic anhydride (Feed Stream 3) into a starting standard heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1$^{3,7}$]decane to produce a slurry containing hexahydro-1,3,5-trinitro-1,3,5-triazine and a spent acid mixture containing acetic acid, acetic anhydride, nitric acid, and ammonium nitrate, or alternatively, adding a quantity of nitric acid (0.0-2.0 equivalents relative to the amount of hexamine added in Feed Stream 1) at 0-15 minutes of the 45 minutes age step, or at 15-30 minutes of the 45 minutes age step, or at 30-45 minutes of the 45 minutes age step;

(c) adding ammonia or an ammonia source to the slurry of step (b) sufficient to neutralize the nitric acid;

(d) quenching the neutralized slurry of step (c) with water to produce an aqueous spent acid mixture containing about 0.0-35 wt % water;

(e) separating the hexahydro-1,3,5-trinitro-1,3,5-triazine and the ammonium nitrate from the aqueous spent acid mixture of step (d);

(f) stirring the hexahydro-1,3,5-trinitro-1,3,5-triazine from step (e) in a 0.0-90 wt % nitric acid solution at reflux to destroy undesired linear nitramines to provide crude hexahydro-1,3,5-trinitro-1,3,5-triazine; and (g) collecting the crude hexahydro-1,3,5-trinitro-1,3,5-triazine from step (f) by filtration.

In further embodiments, the present invention provides for a methanoic acid free process for producing hexahydro-1,3,5-trinitro-1,3,5-triazine, by nitrolysis of 1,3,5,7-tetraazatricyclo[3.3.1.1$^{3,7}$]decane, comprising any one of, or any combination of two or more of the following steps (a) through (g):

(a) while maintaining a temperature of about 40-80° C., concurrently introducing a stream of 1,3,5,7-tetraazatricyclo[3.3.1.1$^{3,7}$]decane in acetic acid, a stream of ammonium nitrate in nitric acid, and a stream of acetic anhydride into a starting heel, the starting heel containing a mixture comprising a majority of acetic acid with nitric acid, ammonium nitrate and acetic anhydride, to produce a slurry, wherein the streams are in proportions greater than necessary for producing the hexahydro-1,3,5-trinitro-1,3,5-triazine;

(b) (age stage) maintaining the resulting slurry at about 40-80° C. for about 45 minutes to affect nitrolysis of the 1,3,5,7-tetraazatricyclo[3.3.1.1$^{3,7}$]decane to produce a slurry containing hexahydro-1,3,5-trinitro-1,3,5-triazine and a spent acid mixture containing acetic acid, acetic anhydride, nitric acid, and ammonium nitrate;

(c) adding ammonia or an ammonia source to the slurry of step (b) sufficient to neutralize the nitric acid;

(d) quenching the neutralized slurry of step (c) with water to produce an aqueous spent acid mixture containing about 0.0-35 wt % water;

(e) separating the hexahydro-1,3,5-trinitro-1,3,5-triazine and the ammonium nitrate from the aqueous spent acid mixture of step (d);

(f) stirring the hexahydro-1,3,5-trinitro-1,3,5-triazine from step (e) in a 0.0-90 wt % nitric acid solution at reflux to destroy undesired linear nitramines to provide crude hexahydro-1,3,5-trinitro-1,3,5-triazine; and (g) collecting the crude hexahydro-1,3,5-trinitro-1,3,5-triazine from step (f) by filtration.

In further embodiments, the present invention provides a methanoic acid free process with a quench to about 0-35 wt % aqueous acetic acid comprising the further step of washing the hexahydro1,3,5-trinitro-1,3,5-triazine and ammonium nitrate separated from step (e) with hot water to produce washed hexahydro1,3,5-tirnitro-1,3,5-triazine prior to proceeding to step (f).

In further embodiments, the present invention provides a methanoic acid free process with a quench to about 0-35 wt % aqueous acetic acid comprising the further step (h) of washing the crude hexahydro-1,3,5-trinitro-1,3,5-triazine from step (g) is washed with water.

In further embodiments, the present invention provides a methanoic acid free process with a quench to about 0-35 wt % aqueous acetic acid comprising the further step (i) or the further step (j) of recrystallizing the washed, or unwashed hexahydro-1,3,5-trinitro-1,3,5-triazine from step (h) or step (g) respectively.

In further embodiments, the present invention provides a methanoic acid free process with a quench to about 0-35 wt % aqueous acetic acid wherein the recrystallization is from a solvent selected from the group consisting of acetone, cyclohexanone, water, dimethyl sulfoxide (DMSO), dimethylformamide (DMF), dimethyacetamide (DMAc), N-methylpyrrolidone (NMP), 2-Methylcyclohexanone, cyclohexyne, formamide, γ-butyrolactone, γ-valerolactone, δ-valerolactone, ε-caprolactone, and mixtures thereof.

In further embodiments, the present invention provides a methanoic acid free process with a quench to about 0-35 wt % aqueous acetic acid wherein the recrystallization solvent is a mixture of cyclohexanone and acetone In further embodiments, the present invention provides a methanoic acid free process with a quench to about 0-35 wt % aqueous acetic acid wherein the aqueous spent acid from step (e) is processed through the pre-distillation evaporators, followed by azeotropic distillation to separate acetic acid from water.

In further embodiments, the present invention provides a methanoic acid free process with a quench to about 0-35 wt % aqueous acetic acid wherein the ammonia source of step (c) is ammonium acetate.

In further embodiments, the present invention provides a methanoic acid free process with a quench to about 0-35 wt % aqueous acetic acid wherein step (c) is performed by first cooling the slurry to about 20-60° C. prior to adding the ammonia or ammonia source.

In further embodiments, the present invention provides a methanoic acid free process with a quench to about 0-35 wt % aqueous acetic acid wherein step (c) is performed by first cooling the slurry to about 25-55° C. prior to adding the ammonia or ammonia source.

In further embodiments, the present invention provides a methanoic acid free process with a quench to about 0-35 wt % aqueous acetic acid wherein step (c) is performed by first cooling the slurry to about 45° C. prior to adding the ammonia or ammonia source.

In further embodiments, the present invention provides a methanoic acid free process with a quench to about 0-35 wt % aqueous acetic acid wherein in step (f) the mixture is subsequently cooled to about 10-60° C. prior to filtration.

In further embodiments, the present invention provides a methanoic acid free process with a quench to about 0-35 wt % aqueous acetic acid wherein in step (f) the mixture is subsequently cooled to about 20-50° C. prior to filtration.

In further embodiments, the present invention provides a methanoic acid free process with a quench to about 0-35 wt % aqueous acetic acid wherein in step (f) the mixture is subsequently cooled to about 25° C. prior to filtration.

In further embodiments, the present invention provides a methanoic acid free process with a quench to about 0-35 wt % aqueous acetic acid wherein in step (a) the temperature is maintained at about 50-75° C.

In further embodiments, the present invention provides a methanoic acid free process with a quench to about 0-35 wt % aqueous acetic acid wherein in step (a) the temperature is maintained at about 65° C.

In further embodiments, the present invention provides a methanoic acid free process with a quench to about 0-35 wt % aqueous acetic acid wherein in step (b) the slurry is maintained at about 50-75° C.

In further embodiments, the present invention provides a methanoic acid free process with a quench to about 0-35 wt % aqueous acetic acid wherein in step (b) the slurry is maintained at about 65° C.

In further embodiments, the present invention provides a methanoic acid free process with a quench to about 0-35 wt % aqueous acetic acid wherein in step (f) the washed hexahydro-1,3,5-trinitro-1,3,5-triazine from step (e) is stirred in about 0-60 wt % nitric acid solution.

In further embodiments, the present invention provides a methanoic acid free process with a quench to about 0-35 wt % aqueous acetic acid wherein in step (f) the washed hexahydro-1,3,5-trinitro-1,3,5-triazine from step (e) is stirred in about 0-40 wt % nitric acid solution.

In further embodiments, the present invention provides a methanoic acid free process with a quench to about 0-35 wt % aqueous acetic acid wherein in step (f) the washed hexahydro-1,3,5-trinitro-1,3,5-triazine from step (e) is stirred in about 0-10 wt % nitric acid solution.

In further embodiments the present invention comprises a methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane.

In further embodiments the present invention comprises a methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane) (Feed Stream 1), a stream of ammonium nitrate in nitric acid (Feed Stream 2), and a stream of acetic anhydride into a starting heel (Feed Stream 3), the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates.

In further embodiments the present invention comprises a methanoic acid free process for producing octahydro-1,3,5, 7-tetranitro-1,3,5,7-tetrazocine, by nitrolysis of 1,3,5,7-tet- raazatricyclo[3.3.1.1$^{3,7}$]decane, comprising:

(a) (stage 1) while maintaining a temperature of about 30-80° C., concurrently introducing a stream of 1,3,5, 7-tetraazatricyclo[3.3.1.1$^{3,7}$]decane in acetic acid (x moles 1,3,5,7-tetraazatricyclo[3.3.1.1$^{3,7}$]decane) (Feed Stream 1), a stream of ammonium nitrate in nitric acid (Feed Stream 2), and a stream of acetic anhydride into a starting heel (Feed Stream 3), the starting heel con- taining a mixture comprising a majority of acetic acid with acetic anhydride, to produce a slurry, wherein the streams are in proportions greater than necessary for producing the octahydro-1,3,5,7-tetranitro-1,3,5,7-tet- razocine intermediates; and (b) (stage 2) following the addition in step (a) and a pause of 0-20 minutes at 30-80° C., while maintaining a temperature of about 30-80° C., concurrently introduc- ing a stream of ammonium nitrate in nitric acid (Feed Stream 2), and a stream of acetic anhydride (Feed Stream 3) into the slurry from step (a), to produce a slurry, wherein the streams are in proportions greater than necessary for producing the octahydro-1,3,5,7- tetranitro-1,3,5,7-tetrazocine intermediates.

In further embodiments the present invention comprises a methanoic acid free process for producing octahydro-1,3,5, 7-tetranitro-1,3,5,7-tetrazocine, by nitrolysis of 1,3,5,7-tet- raazatricyclo[3.3.1.1$^{3,7}$]decane, comprising:

(a) (stage 1) while maintaining a temperature of about 30-80° C., concurrently introducing a stream of 1,3,5, 7-tetraazatricyclo[3.3.1.1$^{3,7}$]decane in acetic acid (x moles 1,3,5,7-tetraazatricyclo[3.3.1.1$^{3,7}$]decane) (Feed Stream 1), a stream of ammonium nitrate in nitric acid (Feed Stream 2), and a stream of acetic anhydride into a starting heel (Feed Stream 3), the starting heel con- taining a mixture comprising a majority of acetic acid with acetic anhydride, to produce a slurry, wherein the streams are in proportions greater than necessary for producing the octahydro-1,3,5,7-tetranitro-1,3,5,7-tet- razocine intermediates;

(b) (stage 2) following the addition in step (a) and a pause of 0-20 minutes at 30-80° C., while maintaining a temperature of about 30-80° C., concurrently introduc- ing a stream of ammonium nitrate in nitric acid (Feed Stream 2), and a stream of acetic anhydride (Feed Stream 3) into the slurry from step (a), to produce a slurry, wherein the streams are in proportions greater than necessary for producing the octahydro-1,3,5,7- tetranitro-1,3,5,7-tetrazocine intermediates; and (c) (stage 3) following the addition in step (b) and a pause of 0-20 minutes at 30-80° C., while maintaining a temperature of about 30-80° C., concurrently introduc- ing a stream of ammonium nitrate in nitric acid (Feed Steam 2), and a stream of acetic anhydride (Feed Stream 3) into the slurry from step (b), to produce a slurry, wherein the streams are in proportions greater than necessary for producing the octahydro-1,3,5,7- tetranitro-1,3,5,7-tetrazocine.

In further embodiments the present invention comprises a methanoic acid free process for producing octahydro-1,3,5, 7-tetranitro-1,3,5,7-tetrazocine, by nitrolysis of 1,3,5,7-tet- raazatricyclo[3.3.1.1$^{3,7}$]decane, comprising:

(a) (stage 1) while maintaining a temperature of about 30-80° C., concurrently introducing a stream of 1,3,5, 7-tetraazatricyclo[3.3.1.1$^{3,7}$]decane in acetic acid (x moles 1,3,5,7-tetraazatricyclo[3.3.1.1$^{3,7}$]decane) (Feed Stream 1), a stream of ammonium nitrate in nitric acid (Feed Stream 2), and a stream of acetic anhydride into a starting heel (Feed Stream 3), the starting heel con- taining a mixture comprising a majority of acetic acid with acetic anhydride, to produce a slurry, wherein the streams are in proportions greater than necessary for producing the octahydro-1,3,5,7-tetranitro-1,3,5,7-tet- razocine intermediates;

(b) (stage 2) following the addition in step (a) and a pause of 0-20 minutes at 30-80° C., while maintaining a temperature of about 30-80° C., concurrently introduc- ing a stream of ammonium nitrate in nitric acid (Feed Stream 2), and a stream of acetic anhydride (Feed Stream 3) into the slurry from step (a), to produce a slurry, wherein the streams are in proportions greater than necessary for producing the octahydro-1,3,5,7- tetranitro-1,3,5,7-tetrazocine intermediates; (c) (stage 3) following the addition in step (b) and a pause of 0-20 minutes at 30-80° C., while maintaining a temperature of about 30-80° C., concurrently introducing a stream of ammonium nitrate in nitric acid (Feed Steam 2), and a stream of acetic anhydride (Feed Stream 3) into the slurry from step (b), to produce a slurry, wherein the streams are in proportions greater than necessary for producing the octahydro-1,3,5,7-tetranitro-1,3,5,7-tet- razocine; and (d) (age stage; indicating aging of the mixture) maintain- ing the resulting slurry from step (c) at about 30-80° C. for about 45 minutes to affect nitrolysis of the 1,3,5,7- tetraazatricyclo[3.3.1.1$^{3,7}$]decane to produce a slurry containing octahydro-1,3,5,7-tetranitro-1,3,5,7-tetrazo- cine and a spent acid mixture containing acetic acid, acetic anhydride, nitric acid, and ammonium nitrate.

In further embodiments the present invention comprises a methanoic acid free process for producing octahydro-1,3,5, 7-tetranitro-1,3,5,7-tetrazocine, by nitrolysis of 1,3,5,7-tet- raazatricyclo[3.3.1.1$^{3,7}$]decane, comprising:

(a) (stage 1) while maintaining a temperature of about 30-80° C., concurrently introducing a stream of 1,3,5, 7-tetraazatricyclo[3.3.1.1$^{3,7}$]decane in acetic acid (x moles 1,3,5,7-tetraazatricyclo[3.3.1.1$^{3,7}$]decane) (Feed Stream 1), a stream of ammonium nitrate in nitric acid (Feed Stream 2), and a stream of acetic anhydride into a starting heel (Feed Stream 3), the starting heel con- taining a mixture comprising a majority of acetic acid with acetic anhydride, to produce a slurry, wherein the streams are in proportions greater than necessary for producing the octahydro-1,3,5,7-tetranitro-1,3,5,7-tet- razocine intermediates;

(b) (stage 2) following the addition in step (a) and a pause of 0-20 minutes at 30-80° C., while maintaining a temperature of about 30-80° C., concurrently introduc- ing a stream of ammonium nitrate in nitric acid (Feed Stream 2), and a stream of acetic anhydride (Feed Stream 3) into the slurry from step (a), to produce a slurry, wherein the streams are in proportions greater than necessary for producing the octahydro-1,3,5,7- tetranitro-1,3,5,7-tetrazocine intermediates; (c) (stage 3) following the addition in step (b) and a pause of 0-20 minutes at 30-80° C., while maintaining a temperature of about 30-80° C., concurrently introducing a stream of ammonium nitrate in nitric acid (Feed Steam 2), and a stream of acetic anhydride (Feed Stream 3) into the slurry from step (b), to produce a slurry, wherein the streams are in proportions greater than necessary for producing the octahydro-1,3,5,7-tetranitro-1,3,5,7-tet- razocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate; and (e) adding ammonia or an ammonia source to the slurry of step (d) sufficient to neutralize the nitric acid.

In further embodiments the present invention comprises a methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane) (Feed Stream 1), a stream of ammonium nitrate in nitric acid (Feed Stream 2), and a stream of acetic anhydride into a starting heel (Feed Stream 3), the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid (Feed Stream 2), and a stream of acetic anhydride (Feed Stream 3) into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid (Feed Steam 2), and a stream of acetic anhydride (Feed Stream 3) into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid; and.

(f) quenching the neutralized slurry of step (e) with water to produce an anhydrous spent acid mixture containing about 0.0-20 wt % acetic anhydride.

In further embodiments the present invention comprises a methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane) (Feed Stream 1), a stream of ammonium nitrate in nitric acid (Feed Stream 2), and a stream of acetic anhydride into a starting heel (Feed Stream 3), the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid (Feed Stream 2), and a stream of acetic anhydride (Feed Stream 3) into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid (Feed Steam 2), and a stream of acetic anhydride (Feed Stream 3) into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid;

(f) quenching the neutralized slurry of step (e) with water to produce an anhydrous spent acid mixture containing about 0.0-20 wt % acetic anhydride; and (g) separating the octahydro-1,3,5,7-tetranitro-1,3,5,7-tetrazocine and the ammonium nitrate from the anhydrous spent acid mixture of step (f).

In further embodiments the present invention comprises a methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane) (Feed Stream 1), a stream of ammonium nitrate in nitric acid (Feed Stream 2), and a stream of acetic anhydride into a starting heel (Feed Stream 3), the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid (Feed Stream 2), and a stream of acetic anhydride (Feed Stream 3) into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid (Feed Steam 2), and a stream of acetic anhydride (Feed Stream 3) into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid;

(f) quenching the neutralized slurry of step (e) with water to produce an anhydrous spent acid mixture containing about 0.0-20 wt % acetic anhydride;

(g) separating the octahydro-1,3,5,7-tetranitro-1,3,5,7-tetrazocine and the ammonium nitrate from the anhydrous spent acid mixture of step (f); and (h) stirring the octahydro-1,3,5,7-tetranitro-1,3,5,7-tetrazocine from step (g) in a 0.0-90 wt % nitric acid solution at reflux to destroy undesired linear nitramines to provide crude octahydro-1,3,5,7-tetranitro-1,3,5,7-tetrazocine.

In further embodiments, the present invention provides for a methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising any one of, or any combination of two or more of the following steps (a) through (i):

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane) (Feed Stream 1), a stream of ammonium nitrate in nitric acid (Feed Stream 2), and a stream of acetic anhydride into a starting heel (Feed Stream 3), the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid (Feed Stream 2), and a stream of acetic anhydride (Feed Stream 3) into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid (Feed Steam 2), and a stream of acetic anhydride (Feed Stream 3) into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid;

(f) quenching the neutralized slurry of step (e) with water to produce an anhydrous spent acid mixture containing about 0.0-20 wt % acetic anhydride;

(g) separating the octahydro-1,3,5,7-tetranitro-1,3,5,7-tetrazocine and the ammonium nitrate from the anhydrous spent acid mixture of step (f);

(h) stirring the octahydro-1,3,5,7-tetranitro-1,3,5,7-tetrazocine from step (g) in a 0.0-90 wt % nitric acid solution at reflux to destroy undesired linear nitramines to provide crude octahydro-1,3,5,7-tetranitro-1,3,5,7-tetrazocine; and (i) collecting the crude octahydro-1,3,5,7-tetranitro-1,3,5,7-tetrazocine from step (h) by filtration.

In further embodiments the present invention provides a methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane) (Feed Stream 1), a stream of ammonium nitrate in nitric acid (Feed Stream 2), and a stream of acetic anhydride into a starting heel (Feed Stream 3), the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid (Feed Stream 2), and a stream of acetic anhydride (Feed Stream 3) into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid (Feed Steam 2), and a stream of acetic anhydride (Feed Stream 3) into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid;

(f) quenching the neutralized slurry of step (e) with water to produce an anhydrous spent acid mixture containing about 0.0-20 wt % acetic anhydride;

(g) separating the octahydro-1,3,5,7-tetranitro-1,3,5,7-tetrazocine and the ammonium nitrate from the anhydrous spent acid mixture of step (f);

(h) stirring the octahydro-1,3,5,7-tetranitro-1,3,5,7-tetrazocine from step (g) in a 0.0-90 wt % nitric acid solution at reflux to destroy undesired linear nitramines to provide crude octahydro-1,3,5,7-tetranitro-1,3,5,7-tetrazocine; and (i) collecting the crude octahydro-1,3,5,7-tetranitro-1,3,5, 7-tetrazocine from step (h) by filtration.

In further embodiments the present invention provides a process comprising the further step of washing the octahydro-1,3,5,7-tetranitro-1,3,5,7-tetrazocine separated from step (g) with hot water to produce washed octahydro-1,3,5, 7-tetranitro-1,3,5,7-tetrazocine prior to proceeding to step (h).

In further embodiments the present invention provides a process comprising the further step (j) of washing the crude octahydro-1,3,5,7-tetranitro-1,3,5,7-tetrazocine from step (i) is washed with water.

In further embodiments the present invention provides a process comprising the further step (k), or the further step (l) of recrystallizing the washed, or unwashed octahydro-1,3, 5,7-tetranitro-1,3,5,7-tetrazocine from step (j) or from step (i) respectively.

In further embodiments the present invention provides a process wherein the recrystallization is from a solvent selected from the group consisting of acetone, cyclohexanone, water, dimethyl sulfoxide (DMSO), dimethylformamide (DMF), dimethyacetamide (DMAc), N-methylpyrrolidone (NMP), 2-Methylcyclohexanone, cyclohexyne, formamide, γ-butyrolactone, γ-valerolactone, δ-valerolactone, ε-caprolactone, and mixtures thereof.

In further embodiments the present invention provides a process comprising the further step (1) of recrystallizing the washed or unwashed octahydro-1,3,5,7-tetranitro-1,3,5,7-tetrazocine from step (i) from a mixture of water and acetone.

In further embodiments the present invention provides a process wherein the ammonia source of step (e) is ammonium acetate.

In further embodiments the present invention provides a process wherein step (e) is performed by first cooling the slurry to about 20-60° C. prior to adding the ammonia or ammonia source.

In further embodiments the present invention provides a process wherein step (e) is performed by first cooling the slurry to about 25-55° C. prior to adding the ammonia or ammonia source.

In further embodiments the present invention provides a process wherein step (e) is performed by first cooling the slurry to about 45° C. prior to adding the ammonia or ammonia source.

In further embodiments the present invention provides a process wherein in step (j) the mixture is subsequently cooled or warmed to about 20-90° C. prior to filtration.

In further embodiments the present invention provides a process wherein in step (j) the mixture is subsequently cooled or warmed to about 20-50° C. prior to filtration.

In further embodiments the present invention provides a process wherein in step (j) the mixture is subsequently cooled to about 25° C. prior to filtration.

In further embodiments the present invention provides a process wherein in step (a) the temperature is maintained at about 40-75° C.

In further embodiments the present invention provides a process wherein in step (a) the temperature is maintained at about 44° C.

In further embodiments the present invention provides a process wherein in step (b) the slurry is maintained at about 40-75° C.

In further embodiments the present invention provides a process wherein in step (b) the slurry is maintained at about 44° C.

In further embodiments the present invention provides a process wherein in step (f) the quenching of the neutralized slurry of step (e) with water is conducted to produce an anhydrous spent acid mixture containing about 0.0-10 wt % acetic anhydride.

In further embodiments the present invention provides a process wherein in step (f) the quenching of the neutralized slurry of step (e) with water is conducted to produce an anhydrous spent acid mixture containing about 0.0-0.5 wt % acetic anhydride.

In further embodiments the present invention provides a process wherein in step (h) the washed or unwashed octahydro-1,3,5,7-tetranitro-1,3,5,7-tetrazocine from step (g) is stirred in about 0-60 wt % nitric acid solution.

In further embodiments the present invention provides a process wherein in step (h) the washed or unwashed octahydro-1,3,5,7-tetranitro-1,3,5,7-tetrazocine from step (g) is stirred in about 0-40 wt % nitric acid solution.

In further embodiments the present invention provides a process wherein in step (h) the washed or unwashed octahydro-1,3,5,7-tetranitro-1,3,5,7-tetrazocine from step (g) is stirred in about 0-10 wt % nitric acid solution.

In further embodiments the present invention provides a process wherein at least a portion of the anhydrous spent acid mixture from step (e) is directly recycled.

In further embodiments the present invention provides a process wherein a portion of the anhydrous spent acid mixture from step (e) is directly recycled via at least one of the following three means:

(i) recycled to the heel, (ii) recycled to dissolve the 1,3,5,7-tetraazatricyclo [3.3.1.1$^{3,7}$]decane, and/or (iii) recycled through pre-distillation evaporators to provide acetic acid and a slurry of acetic acid, RDX, HMX, ammonium nitrate and trace impurities.

In further embodiments the present invention provides a process wherein the portion of the anhydrous spent acid mixture from step (g) that is directly recycled through pre-distillation evaporators is followed by conversion of the acetic acid obtained therefrom to acetic anhydride in a ketene furnace.

In further embodiments the present invention provides a process wherein the slurry from pre-distillation evaporator is collected and recycled to the crude hexahydro-1,3,5-trinitro-1,3,5-triazine from step (g) from subsequent RDX batches.

In further embodiments the present invention provides a process wherein the slurry from pre-distillation evaporator is collected and recycled to the crude octahydro-1,3,5,7-tetranitro-1,3,5,7-tetrazocine from step (g) from subsequent HMX batches.

In further embodiments the present invention provides a process wherein the ammonium nitrate content in the 1,3, 5,7-tetraazatricyclo[3.3.1.1$^{3,7}$]decane feed stream and/or the acetic acid in the heel are determined and the amount, in moles (y), is calculated. 0.0-0.50 equivalents, relative to (y), of 1,3,5,7-tetraazatricyclo[3.3.1.1$^{3,7}$]decane added to the heel prior the start of stage 1. While maintaining a temperature of 20-50° C., 0.0-1.0 equivalents, relative to (y), of nitric acid added to the heel prior the start of stage 1.

In further embodiments the present invention provides a process wherein the resultant aqueous filtrate from step (j) is collected and recycled through pre-distillation evaporators followed by azeotropic distillation.

In further embodiments the present invention provides a process wherein the resultant aqueous filtrate from step (k) is collected and recycled through pre-distillation evaporators followed by azeotropic distillation.

In further embodiments the present invention provides a process wherein while maintaining a temperature of about 20-45° C., to a standard starting heel, containing a mixture comprising a majority of acetic acid with acetic anhydride, are added 0.0-0.10× moles 1,3,5,7-tetraazatricyclo[3.3.1.1$^{3,7}$]decane, 0.0×-0.20× moles ammonium nitrate and 0.0-0.20× moles nitric acid prior to commencing step (a);

In further embodiments the present invention provides a process wherein while maintaining a temperature of about 20-45° C., to a standard starting heel, containing a mixture comprising a majority of acetic acid with acetic anhydride, are added 0.10×-0.20× moles 1,3,5,7-tetraazatricyclo[3.3.1.1$^{3,7}$]decane, 0.20×-0.40× moles ammonium nitrate and 0.20×-0.40× moles nitric acid prior to commencing step (a);

In further embodiments the present invention provides a process wherein while maintaining a temperature of about 20-45° C., to a standard starting heel, containing a mixture comprising a majority of acetic acid with acetic anhydride, are added 0.20×-0.30× moles 1,3,5,7-tetraazatricyclo[3.3.1.1$^{3,7}$]decane, 0.40×-0.60× moles ammonium nitrate and 0.40×-0.60× moles nitric acid prior to commencing step (a);

In further embodiments the present invention provides a process wherein while maintaining a temperature of about 20-45° C., to a standard starting heel, containing a mixture comprising a majority of acetic acid with acetic anhydride, are added 0.30×-0.40× moles 1,3,5,7-tetraazatricyclo[3.3.1.1$^{3,7}$]decane, 0.60×-0.80× moles ammonium nitrate and 0.60×-0.80× moles nitric acid prior to commencing step (a);

In further embodiments the present invention provides a process wherein while maintaining a temperature of about 20-45° C., to a standard starting heel, containing a mixture comprising a majority of acetic acid with acetic anhydride, are added 0.40×-0.50× moles 1,3,5,7-tetraazatricyclo[3.3.1.1$^{3,7}$]decane, 0.80×-1.0× moles ammonium nitrate and 0.80×-1.0× moles nitric acid prior to commencing step (a);

In further embodiments the present invention provides a process wherein in step (d), at 0-15 minutes of the 45 minute hold time, 0.0-2.0× moles of nitric acid are added while maintaining the temperature at 30-80° C.;

In further embodiments the present invention provides a process wherein in step (d), at 15-30 minutes of the 45 minute hold time, 0.0-2.0× moles of nitric acid are added while maintaining the temperature at 30-80° C.;

In further embodiments the present invention provides a process wherein in step (d), at 30-45 minutes of the 45 minute hold time, 0.0-2.0× moles of nitric acid are added while maintaining the temperature at 30-80° C.

In further embodiments the present invention provides a process wherein in step (a), the ammonium nitrate is replaced with sodium nitrate.

In further embodiments the present invention provides a process wherein in step (b), the ammonium nitrate is replaced with sodium nitrate.

In further embodiments the present invention provides a process wherein in step (c), the ammonium nitrate is replaced with sodium nitrate.

In further embodiments the present invention provides a process while maintaining a temperature of about 20-45° C., adding the full quantity of 1,3,5,7-tetraazatricyclo[3.3.1.1$^{3,7}$]decane in acetic acid (x moles of 1,3,5,7-tetraazatricyclo[3.3.1.1$^{3,7}$]decane) to a starting standard heel containing a mixture comprising a majority of acetic acid with acetic anhydride, while maintaining a temperature of about 20-45° C., to the mixture is added ammonium nitrate (1.0×-2.0×) and nitric acid (1.0×-2.0×) prior to commencing step (a). The 1,3,5,7-tetraazatricyclo[3.3.1.1$^{3,7}$]decane in acetic acid feed stream and ammonium nitrate in nitric acid feed stream reduced to zero mass added during step (a). Alternatively, replace ammonium nitrate with sodium nitrate accounting for mole equivalents.

In further embodiments the present invention provides a methanoic acid free no quench process, i.e. without a quenching step for producing octahydro-1,3,5,7-tetranitro-1,3,5,7-tetrazocine, by nitrolysis of 1,3,5,7-tetraazatricyclo [3.3.1.1$^{3,7}$]decane, comprising:

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid;

(f) separating the octahydro-1,3,5,7-tetranitro-1,3,5,7-tetrazocine and the ammonium nitrate from the anhydrous spent acid mixture of step (e);

(g) stirring the octahydro-1,3,5,7-tetranitro-1,3,5,7-tetrazocine from step (f) in a 0.0-90 wt % nitric acid solution at reflux to destroy undesired linear nitramines to provide crude octahydro-1,3,5,7-tetranitro-1,3,5,7-tetrazocine; and (h) collecting the crude octahydro-1,3,5,7-tetranitro-1,3,5,7-tetrazocine from step (g) by filtration.

In further embodiments, the present invention provides for a methanoic acid free process for producing octahydro-1,3,5,7-tetranitro-1,3,5,7-tetrazocine, by nitrolysis of 1,3,5,

33

7-tetraazatricyclo[3.3.1.1$^{3,7}$]decane, comprising any one of, or any combination of two or more of the following steps (a) through (h):

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid;

(f) separating the octahydro-1,3,5,7-tetranitro-1,3,5,7-tetrazocine and the ammonium nitrate from the anhydrous spent acid mixture of step (e);

(g) stirring the octahydro-1,3,5,7-tetranitro-1,3,5,7-tetrazocine from step (f) in a 0.0-90 wt % nitric acid solution at reflux to destroy undesired linear nitramines to provide crude octahydro-1,3,5,7-tetranitro-1,3,5,7-tetrazocine; and (h) collecting the crude octahydro-1,3,5,7-tetranitro-1,3,5,7-tetrazocine from step (g) by filtration.

In further embodiments the present invention provides a methanoic acid free no quench process comprising the further step of washing the octahydro-1,3,5,7-tetranitro-1,3,5,7-tetrazocine separated from step (h) with hot water to produce washed octahydro-1,3,5,7-tetranitro-1,3,5,7-tetrazocine prior to proceeding to step (g).

In further embodiments the present invention provides a methanoic acid free no quench process comprising the further step (i) of washing the crude octahydro-1,3,5,7-tetranitro-1,3,5,7-tetrazocine from step (h) is washed with water.

In further embodiments the present invention provides a methanoic acid free no quench process comprising the further step (j), or the further step of (k) of recrystallizing the washed, or unwashed octahydro-1,3,5,7-tetranitro-1,3,5,7-tetrazocine from step (h) or from step (g) respectively.

In further embodiments the present invention provides a methanoic acid free no quench process wherein the recrystallization is from a solvent selected from the group consisting of acetone, cyclohexanone, water, dimethyl sulfoxide (DMSO), dimethylformamide (DMF), dimethyacetamide (DMAc), N-methylpyrrolidone (NMP), 2-Methylcyclohexanone, cyclohexyne, formamide, γ-butyrolactone, γ-valerolactone, δ-valerolactone, ε-caprolactone, and mixtures thereof.

In further embodiments the present invention provides a methanoic acid free no quench process the further step (1) of recrystallizing the washed or unwashed octahydro-1,3,5,7-tetranitro-1,3,5,7-tetrazocine from step (h) from a mixture of water and acetone.

In further embodiments the present invention provides a methanoic acid free no quench process wherein the ammonia source of step (e) is ammonium acetate.

In further embodiments the present invention provides a methanoic acid free no quench process wherein step (e) is performed by first cooling the slurry to about 20-60° C. prior to adding the ammonia or ammonia source.

In further embodiments the present invention provides a methanoic acid free no quench process wherein step (e) is performed by first cooling the slurry to about 25-55° C. prior to adding the ammonia or ammonia source.

In further embodiments the present invention provides a methanoic acid free no quench process wherein step (e) is performed by first cooling the slurry to about 45° C. prior to adding the ammonia or ammonia source.

In further embodiments the present invention provides a methanoic acid free no quench process wherein in step (f) the mixture is subsequently cooled or warmed to about 20-90° C. prior to filtration.

In further embodiments the present invention provides a methanoic acid free no quench process wherein in step (f) the mixture is subsequently cooled or warmed to about 20-50° C. prior to filtration.

In further embodiments the present invention provides a methanoic acid free no quench process wherein in step (f) the mixture is subsequently cooled to about 25° C. prior to filtration.

In further embodiments the present invention provides a methanoic acid free no quench process wherein in step (a) the temperature is maintained at about 40-75° C.

In further embodiments the present invention provides a methanoic acid free no quench process wherein in step (a) the temperature is maintained at about 44° C.

In further embodiments the present invention provides a methanoic acid free no quench process wherein in step (b) the slurry is maintained at about 40-75° C.

In further embodiments the present invention provides a methanoic acid free no quench process wherein in step (b) the slurry is maintained at about 44° C.

In further embodiments the present invention provides a methanoic acid free no quench process wherein in step (g) the washed or unwashed octahydro-1,3,5,7-tetranitro-1,3,5,7-tetrazocine from step (f) is stirred in about 0-60 wt % nitric acid solution.

In further embodiments the present invention provides a methanoic acid free no quench process wherein in step (g) the washed or unwashed octahydro-1,3,5,7-tetranitro-1,3,5,7-tetrazocine from step (f) is stirred in about 0-40 wt % nitric acid solution.

In further embodiments the present invention provides a methanoic acid free no quench process wherein in step (g)

the washed or unwashed octahydro-1,3,5,7-tetranitro-1,3,5,7-tetrazocine from step (f) is stirred in about 0-10 wt % nitric acid solution.

In further embodiments the present invention provides a methanoic acid free no quench process wherein at least a portion of the anhydrous spent acid mixture from step (f) is directly recycled.

In further embodiments the present invention provides a methanoic acid free no quench process wherein a portion of the anhydrous spent acid mixture from step (f) is directly recycled via at least one of the following three means:

(i) recycled to the heel, (ii) following quenching of the acetic anhydride with water to 0.0-0.50 wt % acetic anhydride, recycled to dissolve the 1,3,5,7-tetraazatricyclo[3.3.1.1$^{3,7}$]decane, and/or (iii) recycled through pre-distillation evaporators to provide a solution of acetic acid and acetic anhydride, and a slurry of acetic acid, RDX, HMX, ammonium nitrate and trace impurities.

In further embodiments the present invention provides a methanoic acid free no quench process wherein the portion of the anhydrous spent acid mixture from step (f) that is directly recycled through pre-distillation evaporators is followed by azeotropic distillation to separate acetic acid from acetic anhydride..

In further embodiments the present invention provides a methanoic acid free no quench process wherein the slurry from pre-distillation evaporator is collected and recycled to the crude hexahydro-1,3,5-trinitro-1,3,5-triazine filtration from step (f) from subsequent RDX batches.

In further embodiments the present invention provides a methanoic acid free no quench process wherein the slurry from pre-distillation evaporator is collected and recycled to the crude octahydro-1,3,5,7-tetranitro-1,3,5,7-tetrazocine filtration from step (f) from subsequent HMX batches.

In further embodiments the present invention provides a methanoic acid free no quench process wherein the ammonium nitrate content in the 1,3,5,7-tetraazatricyclo[3.3.1.1$^{3,7}$]decane feed stream and/or the acetic acid in the heel are determined and the amount, in moles (y), is calculated. 0.0-0.50 equivalents, relative to (y), of 1,3,5,7-tetraazatricyclo[3.3.1.1$^{3,7}$]decane added to the heel prior the start of stage 1. While maintaining a temperature of 20-45° C., 0.0-1.0 equivalents, relative to (y), of nitric acid added to the heel prior the start of stage 1.

In further embodiments the present invention provides a methanoic acid free no quench process wherein the resultant aqueous filtrate is collected and recycled through pre-distillation evaporators followed by azeotropic distillation.

In further embodiments the present invention provides a methanoic acid free no quench process wherein while maintaining a temperature of about 20-45° C., to a standard starting heel, containing a mixture comprising a majority of acetic acid with acetic anhydride, are added 0.0-0.10× moles 1,3,5,7-tetraazatricyclo[3.3.1.1$^{3,7}$]decane, 0.0×-0.20× moles ammonium nitrate and 0.0-0.20× moles nitric acid prior to commencing step (a);

In further embodiments the present invention provides a methanoic acid free no quench process while maintaining a temperature of about 20-45° C., to a standard starting heel, containing a mixture comprising a majority of acetic acid with acetic anhydride, are added 0.10×-0.20× moles 1,3,5,7-tetraazatricyclo[3.3.1.1$^{3,7}$]decane, 0.20×-0.40× moles ammonium nitrate and 0.20-0.40× moles nitric acid prior to commencing step (a);

In further embodiments the present invention provides a methanoic acid free no quench process wherein while maintaining a temperature of about 20-45° C., to a standard starting heel, containing a mixture comprising a majority of acetic acid with acetic anhydride, are added 0.20×-0.30× moles 1,3,5,7-tetraazatricyclo[3.3.1.1$^{3,7}$]decane, 0.40×-0.60× moles ammonium nitrate and 0.40×-0.60× moles nitric acid prior to commencing step (a);

In further embodiments the present invention provides a methanoic acid free no quench process wherein while maintaining a temperature of about 20-45° C., to a standard starting heel, containing a mixture comprising a majority of acetic acid with acetic anhydride, are added 0.30×-0.40× moles 1,3,5,7-tetraazatricyclo[3.3.1.1$^{3,7}$]decane, 0.60×-0.80× moles ammonium nitrate and 0.60×-0.80× moles nitric acid prior to commencing step (a);

In further embodiments the present invention provides a methanoic acid free no quench process wherein while maintaining a temperature of about 20-45° C., to a standard starting heel, containing a mixture comprising a majority of acetic acid with acetic anhydride, are added 0.40×-0.50× moles 1,3,5,7-tetraazatricyclo[3.3.1.1$^{3,7}$]decane, 0.80×-1.0× moles ammonium nitrate and 0.80×-1.0× moles nitric acid prior to commencing step (a);

In further embodiments the present invention provides a methanoic acid free no quench process wherein in step (d), at 0-15 minutes of the 45 minute hold time, 0.0-2.0× moles of nitric acid are added while maintaining the temperature at 30-80° C.;

In further embodiments the present invention provides a methanoic acid free no quench process wherein in step (d), at 15-30 minutes of the 45 minute hold time, 0.0-2.0× moles of nitric acid are added while maintaining the temperature at 30-80° C.;

In further embodiments the present invention provides a methanoic acid free no quench process wherein in step (d), at 30-45 minutes of the 45 minute hold time, 0.0-2.0× moles of nitric acid are added while maintaining the temperature at 30-80° C.

In further embodiments the present invention provides a methanoic acid free no quench process wherein step (a), the ammonium nitrate is replaced with sodium nitrate.

In further embodiments the present invention provides a methanoic acid free no quench process wherein in step (b), the ammonium nitrate is replaced with sodium nitrate.

In further embodiments the present invention provides a methanoic acid free no quench process wherein in step (c), the ammonium nitrate is replaced with sodium nitrate.

In further embodiments the present invention provides a methanoic acid free no quench process while maintaining a temperature of about 20-45° C., adding the full quantity of 1,3,5,7-tetraazatricyclo[3.3.1.1$^{3,7}$]decane in acetic acid (x moles of 1,3,5,7-tetraazatricyclo[3.3.1.1$^{3,7}$]decane) to a starting standard heel containing a mixture comprising a majority of acetic acid with acetic anhydride, while maintaining a temperature of about 20-45° C., to the mixture is added ammonium nitrate (1.0×-2.0×) and nitric acid (1.0×-2.0×) prior to commencing step (a). The 1,3,5,7-tetraazatricyclo[3.3.1.1$^{3,7}$]decane in acetic acid of feed stream 1 and ammonium nitrate in nitric acid of feed stream 2 reduced to zero mass added during step (a). Alternatively, replace ammonium nitrate with sodium nitrate accounting for mole equivalents.

In further embodiments the present invention provides a methanoic acid free no neutralization process, i.e. without a neutralization step for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) quenching the slurry of step (d) with water to produce an anhydrous spent acid mixture containing about 0.0-20 wt % acetic anhydride;

(f) separating the octahydro-1,3,5,7-tetranitro-1,3,5,7-tetrazocine and the ammonium nitrate from the anhydrous spent acid mixture of step (e);

(g) stirring the octahydro-1,3,5,7-tetranitro-1,3,5,7-tetrazocine from step (f) in a 0.0-90 wt % nitric acid solution at reflux to destroy undesired linear nitramines to provide crude octahydro-1,3,5,7-tetranitro-1,3,5,7-tetrazocine; and (h) collecting the crude octahydro-1,3,5,7-tetranitro-1,3,5,7-tetrazocine from step (g) by filtration.

In further embodiments, the present invention provides for a methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising any one of, or any combination of two or more of the following steps (a) through (h):

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) quenching the slurry of step (d) with water to produce an anhydrous spent acid mixture containing about 0.0-20 wt % acetic anhydride;

(f) separating the octahydro-1,3,5,7-tetranitro-1,3,5,7-tetrazocine and the ammonium nitrate from the anhydrous spent acid mixture of step (e);

(g) stirring the octahydro-1,3,5,7-tetranitro-1,3,5,7-tetrazocine from step (f) in a 0.0-90 wt % nitric acid solution at reflux to destroy undesired linear nitramines to provide crude octahydro-1,3,5,7-tetranitro-1,3,5,7-tetrazocine; and (h) collecting the crude octahydro-1,3,5,7-tetranitro-1,3,5,7-tetrazocine from step (g) by filtration.

In further embodiments the present invention provides a methanoic acid free no neutralization process comprising the further step of washing the octahydro-1,3,5,7-tetranitro-1,3,5,7-tetrazocine separated from step (h) with hot water to produce washed octahydro-1,3,5,7-tetranitro-1,3,5,7-tetrazocine prior to proceeding to step (g).

In further embodiments the present invention provides a methanoic acid free no neutralization process comprising the further step (i) of washing the crude octahydro-1,3,5,7-tetranitro-1,3,5,7-tetrazocine from step (h) is washed with water.

In further embodiments the present invention provides a methanoic acid free no neutralization process comprising the further step (j), or the further step of (k) of recrystallizing the washed, or unwashed octahydro-1,3,5,7-tetranitro-1,3,5,7-tetrazocine from step (h) or from step (g) respectively.

In further embodiments the present invention provides a methanoic acid free no neutralization process wherein the recrystallization is from a solvent selected from the group consisting of acetone, cyclohexanone, water, dimethyl sulfoxide (DMSO), dimethylformamide (DMF), dimethyacetamide (DMAc), N-methylpyrrolidone (NMP), 2-Methylcyclohexanone, cyclohexyne, formamide, γ-butyrolactone, γ-valerolactone, δ-valerolactone, ε-caprolactone, and mixtures thereof.

In further embodiments the present invention provides a methanoic acid free no neutralization process comprising the further step (1) of recrystallizing the washed or unwashed octahydro-1,3,5,7-tetranitro-1,3,5,7-tetrazocine from step (h) from a mixture of water and acetone.

In further embodiments the present invention provides a methanoic acid free no neutralization process wherein the ammonia source of step (e) is ammonium acetate.

In further embodiments the present invention provides a methanoic acid free no neutralization process wherein step (e) is performed by first cooling the slurry to about 20-60° C. prior to adding the ammonia or ammonia source.

In further embodiments the present invention provides a methanoic acid free no neutralization process wherein step (e) is performed by first cooling the slurry to about 25-55° C. prior to adding the ammonia or ammonia source.

In further embodiments the present invention provides a methanoic acid free no neutralization process wherein step (e) is performed by first cooling the slurry to about 45° C. prior to adding the ammonia or ammonia source.

In further embodiments the present invention provides a methanoic acid free no neutralization process wherein in step (f) the mixture is subsequently cooled or warmed to about 20-90° C. prior to filtration.

In further embodiments the present invention provides a methanoic acid free no neutralization process wherein in step (f) the mixture is subsequently cooled or warmed to about 20-50° C. prior to filtration.

In further embodiments the present invention provides a methanoic acid free no neutralization process wherein in step (f) the mixture is subsequently cooled to about 25° C. prior to filtration.

In further embodiments the present invention provides a methanoic acid free no neutralization process wherein in step (a) the temperature is maintained at about 40-75° C.

In further embodiments the present invention provides a methanoic acid free no neutralization process wherein in step (a) the temperature is maintained at about 44° C.

In further embodiments the present invention provides a methanoic acid free no neutralization process wherein in step (b) the slurry is maintained at about 40-75° C.

In further embodiments the present invention provides a methanoic acid free no neutralization process wherein in step (b) the slurry is maintained at about 44° C.

In further embodiments the present invention provides a methanoic acid free no neutralization process wherein in step (e) the quenching of the slurry of step (d) with water is conducted to produce an anhydrous spent acid mixture containing about 0.0-10 wt % acetic anhydride.

In further embodiments the present invention provides a methanoic acid free no neutralization process wherein in step (e) the quenching of the slurry of step (d) with water is conducted to produce an anhydrous spent acid mixture containing about 0.0-0.5 wt % acetic anhydride.

In further embodiments the present invention provides a methanoic acid free no neutralization process wherein in step (g) the washed or unwashed octahydro-1,3,5,7-tetrani-tro-1,3,5,7-tetrazocine from step (f) is stirred in about 0-60 wt % nitric acid solution.

In further embodiments the present invention provides a methanoic acid free no neutralization process wherein in step (g) the washed or unwashed octahydro-1,3,5,7-tetrani-tro-1,3,5,7-tetrazocine from step (f) is stirred in about 0-40 wt % nitric acid solution.

In further embodiments the present invention provides a methanoic acid free no neutralization process wherein in step (g) the washed or unwashed octahydro-1,3,5,7-tetrani-tro-1,3,5,7-tetrazocine from step (f) is stirred in about 0-10 wt % nitric acid solution.

In further embodiments the present invention provides a methanoic acid free no neutralization process wherein at least a portion of the anhydrous spent acid mixture from step (f) is directly recycled.

In further embodiments the present invention provides a methanoic acid free no neutralization process wherein a portion of the anhydrous spent acid mixture from step (f) is directly recycled via at least one of the following three means:

(i) recycled to the heel, (ii) following neutralization of nitric acid with ammonia, recycled to dissolve the 1,3,5,7-tetraazatricyclo [3.3.1.1$^{3,7}$]decane, and/or (iii) following neutralization of nitric acid with ammonia, recycled through pre-distillation evaporators to provide acetic acid and a slurry of acetic acid, RDX, HMX, ammonium nitrate and trace impurities.

In further embodiments the present invention provides a methanoic acid free no neutralization process wherein the portion of the anhydrous spent acid mixture from step (f) that is directly recycled through pre-distillation evaporators is followed by conversion of the acetic acid obtained there-from to acetic anhydride in a ketene furnace.

In further embodiments the present invention provides a methanoic acid free no neutralization process wherein the slurry from pre-distillation evaporator is collected and recycled to the crude hexahydro-1,3,5-trinitro-1,3,5-triazine filtration from step (f) from subsequent RDX batches.

In further embodiments the present invention provides a methanoic acid free no neutralization process wherein the slurry from pre-distillation evaporator is collected and recycled to the crude octahydro-1,3,5,7-tetranitro-1,3,5,7-tetrazocine filtration from step (f) from subsequent HMX batches.

In further embodiments the present invention provides a methanoic acid free no neutralization process wherein the ammonium nitrate content in the 1,3,5,7-tetraazatricyclo [3.3.1.1$^{3,7}$]decane feed stream and/or the acetic acid in the heel are determined and the amount, in moles (y), is calcu-lated. The process of stage 1 wherein the nitric acid content in the acetic acid of the heel is determined and the amount, in moles (y1) is calculated. 0.0-0.50 equivalents, relative to (y), of 1,3,5,7-tetraazatricyclo[3.3.1.1$^{3,7}$]decane added to the heel prior to the start of stage 1. While maintaining a temperature of 20-45° C., 0.0 to (y−y1) moles of nitric acid is added to the heel prior to the start of stage 1. If (y−y1) is a negative number, then no additional nitric acid is added to the recycled heel In further embodiments the present invention provides a methanoic acid free no neutralization process wherein the resultant aqueous filtrate is collected and recycled through pre-distillation evaporators followed by azeotropic distilla-tion.

In further embodiments the present invention provides a methanoic acid free no neutralization process wherein while maintaining a temperature of about 20-45° C., to a standard starting heel, containing a mixture comprising a majority of acetic acid with acetic anhydride, are added 0.0-0.10× moles 1,3,5,7-tetraazatricyclo[3.3.1.1$^{3,7}$]decane, 0.0×-0.20× moles ammonium nitrate and 0.0-0.20× moles nitric acid prior to commencing step (a);

In further embodiments the present invention provides a methanoic acid free no neutralization process wherein while maintaining a temperature of about 20-45° C., to a standard starting heel, containing a mixture comprising a majority of acetic acid with acetic anhydride, are added 0.10×-0.20× moles 1,3,5,7-tetraazatricyclo[3.3.1.1$^{3,7}$]decane, 0.20×-

0.40x moles ammonium nitrate and 0.20x-0.40x moles nitric acid prior to commencing step (a);

In further embodiments the present invention provides a methanoic acid free no neutralization process wherein while maintaining a temperature of about 20-45° C., to a standard starting heel, containing a mixture comprising a majority of acetic acid with acetic anhydride, are added 0.20x-0.30x moles 1,3,5,7-tetraazatricyclo[3.3.1.1$^{3,7}$]decane, 0.40x-0.60x moles ammonium nitrate and 0.40x-0.60x moles nitric acid prior to commencing step (a);

In further embodiments the present invention provides a methanoic acid free no neutralization process wherein while maintaining a temperature of about 20-45° C., to a standard starting heel, containing a mixture comprising a majority of acetic acid with acetic anhydride, are added 0.30x-0.40x moles 1,3,5,7-tetraazatricyclo[3.3.1.1$^{3,7}$]decane, 0.60x-0.80x moles ammonium nitrate and 0.60x-0.80x moles nitric acid prior to commencing step (a);

In further embodiments the present invention provides a methanoic acid free no neutralization process wherein while maintaining a temperature of about 20-45° C., to a standard starting heel, containing a mixture comprising a majority of acetic acid with acetic anhydride, are added 0.40x-0.50x moles 1,3,5,7-tetraazatricyclo[3.3.1.1$^{3,7}$]decane, 0.80x-1.0x moles ammonium nitrate and 0.80x-1.0x moles nitric acid prior to commencing step (a);

In further embodiments the present invention provides a methanoic acid free no neutralization process wherein in step (d), at 0-15 minutes of the 45 minute hold time, 0.0-2.0x moles of nitric acid are added while maintaining the temperature at 30-80° C.;

In further embodiments the present invention provides a methanoic acid free no neutralization process wherein in step (d), at 15-30 minutes of the 45 minute hold time, 0.0-2.0x moles of nitric acid are added while maintaining the temperature at 30-80° C.;

In further embodiments the present invention provides a methanoic acid free no neutralization process wherein in step (d), at 30-45 minutes of the 45 minute hold time, 0.0-2.0x moles of nitric acid are added while maintaining the temperature at 30-80° C.

In further embodiments the present invention provides a methanoic acid free no neutralization process wherein in step (a), the ammonium nitrate is replaced with sodium nitrate.

In further embodiments the present invention provides a methanoic acid free no neutralization process wherein in step (b), the ammonium nitrate is replaced with sodium nitrate.

In further embodiments the present invention provides a methanoic acid free no neutralization process wherein in step (c), the ammonium nitrate is replaced with sodium nitrate.

In further embodiments the present invention provides a methanoic acid free no neutralization process while maintaining a temperature of about 20-45° C., adding the full quantity of 1,3,5,7-tetraazatricyclo[3.3.1.1$^{3,7}$]decane in acetic acid (x moles of 1,3,5,7-tetraazatricyclo[3.3.1.1$^{3,7}$]decane) to a starting standard heel containing a mixture comprising a majority of acetic acid with acetic anhydride, while maintaining a temperature of about 20-45° C., to the mixture is added ammonium nitrate (1.0x-2.0x) and nitric acid (1.0x-2.0x) prior to commencing step (a). The 1,3,5,7-tetraazatricyclo[3.3.1.1$^{3,7}$]decane in acetic acid of feed stream 1 and ammonium nitrate in nitric acid of feed stream 2 reduced to zero mass added during step (a). Alternatively, replace ammonium nitrate with sodium nitrate accounting for mole equivalents.

In further embodiments the present invention provides both a methanoic acid free no quench and no neutralization process, i.e. without a quenching step and without a neutralization step process for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) separating the octahydro-1,3,5,7-tetranitro-1,3,5,7-tetrazocine and the ammonium nitrate from the anhydrous spent acid mixture of step (d);

(f) stirring the octahydro-1,3,5,7-tetranitro-1,3,5,7-tetrazocine from step (e) in a 0.0-90 wt % nitric acid solution at reflux to destroy undesired linear nitramines to provide crude octahydro-1,3,5,7-tetranitro-1,3,5,7-tetrazocine; and (g) collecting the crude octahydro-1,3,5,7-tetranitro-1,3,5,7-tetrazocine from step (f) by filtration.

In further embodiments, the present invention provides for a methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising any one of, or any combination of two or more of the following steps (a) through (g):

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) separating the octahydro-1,3,5,7-tetranitro-1,3,5,7-tetrazocine and the ammonium nitrate from the anhydrous spent acid mixture of step (d);

(f) stirring the octahydro-1,3,5,7-tetranitro-1,3,5,7-tetrazocine from step (e) in a 0.0-90 wt % nitric acid solution at reflux to destroy undesired linear nitramines to provide crude octahydro-1,3,5,7-tetranitro-1,3,5,7-tetrazocine; and (g) collecting the crude octahydro-1,3,5,7-tetranitro-1,3,5,7-tetrazocine from step (f) by filtration.

In further embodiments the present invention provides both a methanoic acid free no quench and no neutralization process comprising the further step of washing the octahydro-1,3,5,7-tetranitro-1,3,5,7-tetrazocine separated from step (g) with hot water to produce washed octahydro-1,3,5,7-tetranitro-1,3,5,7-tetrazocine prior to proceeding to step (f).

In further embodiments the present invention provides both a methanoic acid free no quench and no neutralization process comprising the further step (h) of washing the crude octahydro-1,3,5,7-tetranitro-1,3,5,7-tetrazocine from step (g) is washed with water.

In further embodiments the present invention provides both a methanoic acid free no quench and no neutralization process comprising the further step (i), or the further step of (j) of recrystallizing the washed, or unwashed octahydro-1,3,5,7-tetranitro-1,3,5,7-tetrazocine from step (g) or from step (f) respectively.

In further embodiments the present invention provides both a methanoic acid free no quench and no neutralization process wherein the recrystallization is from a solvent selected from the group consisting of acetone, cyclohexanone, water, dimethyl sulfoxide (DMSO), dimethylformamide (DMF), dimethyacetamide (DMAc), N-methylpyrrolidone (NMP), 2-Methylcyclohexanone, cyclohexyne, formamide, γ-butyrolactone, γ-valerolactone, δ-valerolactone, ε-caprolactone, and mixtures thereof.

In further embodiments the present invention provides both a methanoic acid free no quench and no neutralization process comprising the further step (k) of recrystallizing the washed or unwashed octahydro-1,3,5,7-tetranitro-1,3,5,7-tetrazocine from step (g) from a mixture of water and acetone.

In further embodiments the present invention provides both a methanoic acid free no quench and no neutralization process wherein in step (e) the mixture is subsequently cooled or warmed to about 20-90° C. prior to filtration.

In further embodiments the present invention provides both a methanoic acid free no quench and no neutralization process wherein in step (e) the mixture is subsequently cooled or warmed to about 20-50° C. prior to filtration.

In further embodiments the present invention provides both a methanoic acid free no quench and no neutralization process wherein in step (e) the mixture is subsequently cooled to about 25° C. prior to filtration.

In further embodiments the present invention provides both a methanoic acid free no quench and no neutralization process wherein in step (a) the temperature is maintained at about 40-75° C.

In further embodiments the present invention provides both a methanoic acid free no quench and no neutralization process wherein in step (a) the temperature is maintained at about 44° C.

In further embodiments the present invention provides both a methanoic acid free no quench and no neutralization process wherein in step (b) the slurry is maintained at about 40-75° C.

In further embodiments the present invention provides both a methanoic acid free no quench and no neutralization process wherein in step (b) the slurry is maintained at about 44° C.

In further embodiments the present invention provides both a methanoic acid free no quench and no neutralization process wherein in step (f) the washed or unwashed octahydro-1,3,5,7-tetranitro-1,3,5,7-tetrazocine from step (e) is stirred in about 0-60 wt % nitric acid solution.

In further embodiments the present invention provides both a methanoic acid free no quench and no neutralization process wherein in step (f) the washed or unwashed octahydro-1,3,5,7-tetranitro-1,3,5,7-tetrazocine from step (e) is stirred in about 0-40 wt % nitric acid solution.

In further embodiments the present invention provides both a methanoic acid free no quench and no neutralization process wherein in step (f) the washed or unwashed octahydro-1,3,5,7-tetranitro-1,3,5,7-tetrazocine from step (e) is stirred in about 0-10 wt % nitric acid solution.

In further embodiments the present invention provides both a methanoic acid free no quench and no neutralization process wherein at least a portion of the anhydrous spent acid mixture from step (e) is directly recycled.

In further embodiments the present invention provides both a methanoic acid free no quench and no neutralization process wherein a portion of the anhydrous spent acid mixture from step (e) is directly recycled via at least one of the following three means:

(i) recycled to the heel, (ii) following neutralization of nitric acid with ammonia, and quenching the acetic anhydride to 0.0-0.50 wt % acetic anhydride, recycled to dissolve the 1,3,5,7-tetraazatricyclo[3.3.1.1$^{3,7}$]decane, and/or (iii) following neutralization of nitric acid with ammonia, recycled through pre-distillation evaporators to provide solution of acetic acid and acetic anhydride, RDX, HMX, ammonium nitrate and trace impurities.

In further embodiments the present invention provides both a methanoic acid free no quench and no neutralization process wherein the portion of the anhydrous spent acid mixture from step (e) that is directly recycled through pre-distillation evaporators is followed by azeotropic distillation to separate acetic acid from acetic anhydride.

In further embodiments the present invention provides both a methanoic acid free no quench and no neutralization process wherein the slurry from pre-distillation evaporator is collected and recycled to the crude hexahydro-1,3,5-trinitro-1,3,5-triazine filtration from step (e) from subsequent RDX batches.

In further embodiments the present invention provides both a methanoic acid free no quench and no neutralization process wherein the slurry from pre-distillation evaporator is collected and recycled to the crude octahydro-1,3,5,7-tetranitro-1,3,5,7-tetrazocine filtration from step (e) from subsequent HMX batches.

In further embodiments the present invention provides both a methanoic acid free no quench and no neutralization process wherein the ammonium nitrate content in the 1,3,5,7-tetraazatricyclo[3.3.1.1$^{3,7}$]decane feed stream and/or the acetic acid in the heel are determined and the amount, in moles (y), is calculated. The process of stage 1 wherein the nitric acid content in the acetic acid of the heel is determined and the amount, in moles (y$^1$) is calculated. 0.0-0.50 equivalents, relative to (y), of 1,3,5,7-tetraazatricyclo[3.3.1.1$^{3,7}$] decane added to the heel prior the start of stage 1. While maintaining a temperature of 20-45° C., 0.0 to (y–y$^1$) moles of nitric acid added to the heel prior the start of stage 1. If (y–y$^1$) is a negative number, then no additional nitric acid is added to the recycled heel.

In further embodiments the present invention provides both a methanoic acid free no quench and no neutralization process wherein the resultant aqueous filtrate is collected and recycled through pre-distillation evaporators followed by azeotropic distillation.

In further embodiments the present invention provides both a methanoic acid free no quench and no neutralization process wherein while maintaining a temperature of about 20-45° C., to a standard starting heel, containing a mixture comprising a majority of acetic acid with acetic anhydride, are added 0.0-0.10× moles 1,3,5,7-tetraazatricyclo[3.3.1.1$^{3,7}$]decane, 0.0×-0.20× moles ammonium nitrate and 0.0-0.20× moles nitric acid prior to commencing step (a);

In further embodiments the present invention provides both a methanoic acid free no quench and no neutralization process wherein while maintaining a temperature of about 20-45° C., to a standard starting heel, containing a mixture comprising a majority of acetic acid with acetic anhydride, are added 0.10×-0.20× moles 1,3,5,7-tetraazatricyclo[3.3.1.1$^{3,7}$]decane, 0.20×-0.40× moles ammonium nitrate and 0.20×-0.40× moles nitric acid prior to commencing step (a);

In further embodiments the present invention provides both a methanoic acid free no quench and no neutralization process wherein while maintaining a temperature of about 20-45° C., to a standard starting heel, containing a mixture comprising a majority of acetic acid with acetic anhydride, are added 0.20×-0.30× moles 1,3,5,7-tetraazatricyclo[3.3.1.1$^{3,7}$]decane, 0.40×-0.60× moles ammonium nitrate and 0.40×-0.60× moles nitric acid prior to commencing step (a);

In further embodiments the present invention provides both a methanoic acid free no quench and no neutralization process wherein while maintaining a temperature of about 20-45° C., to a standard starting heel, containing a mixture comprising a majority of acetic acid with acetic anhydride, are added 0.30×-0.40× moles 1,3,5,7-tetraazatricyclo

[3.3.1.1$^{3,7}$]decane, 0.60×-0.80× moles ammonium nitrate and 0.60×-0.80× moles nitric acid prior to commencing step (a);

In further embodiments the present invention provides both a methanoic acid free no quench and no neutralization process wherein while maintaining a temperature of about 20-45° C., to a standard starting heel, containing a mixture comprising a majority of acetic acid with acetic anhydride, are added 0.40×-0.50× moles 1,3,5,7-tetraazatricyclo[3.3.1.1$^{3,7}$]decane, 0.80×-1.0× moles ammonium nitrate and 0.80×-1.0× moles nitric acid prior to commencing step (a);

In further embodiments the present invention provides both a methanoic acid free no quench and no neutralization process wherein in step (d), at 0-15 minutes of the 45 minute hold time, 0.0-2.0× moles of nitric acid are added while maintaining the temperature at 30-80° C.;

In further embodiments the present invention provides both a methanoic acid free no quench and no neutralization process wherein in step (d), at 15-30 minutes of the 45 minute hold time, 0.0-2.0× moles of nitric acid are added while maintaining the temperature at 30-80° C.;

In further embodiments the present invention provides both a methanoic acid free no quench and no neutralization process wherein in step (d), at 30-45 minutes of the 45 minute hold time, 0.0-2.0× moles of nitric acid are added while maintaining the temperature at 30-80° C.

In further embodiments the present invention provides both a methanoic acid free no quench and no neutralization process wherein in step (a), the ammonium nitrate is replaced with sodium nitrate.

In further embodiments the present invention provides both a methanoic acid free no quench and no neutralization process wherein in step (b), the ammonium nitrate is replaced with sodium nitrate.

In further embodiments the present invention provides both a methanoic acid free no quench and no neutralization process wherein in step (c), the ammonium nitrate is replaced with sodium nitrate.

In further embodiments the present invention provides both a methanoic acid free no quench and no neutralization process while maintaining a temperature of about 20-45° C., adding the full quantity of 1,3,5,7-tetraazatricyclo[3.3.1.1$^{3,7}$]decane in acetic acid (x moles of 1,3,5,7-tetraazatricyclo[3.3.1.1$^{3,7}$]decane) to a starting standard heel containing a mixture comprising a majority of acetic acid with acetic anhydride, while maintaining a temperature of about 20-45° C., to the mixture is added ammonium nitrate (1.0×-2.0×) and nitric acid (1.0×-2.0×) prior to commencing step (a). The 1,3,5,7-tetraazatricyclo[3.3.1.1$^{3,7}$]decane in acetic acid of feed stream 1 and ammonium nitrate in nitric acid of feed stream 2 reduced to zero mass added during step (a). Alternatively, replace ammonium nitrate with sodium nitrate accounting for mole equivalents.

In further embodiments, the present invention provides a methanoic acid free process with a quench to about 0-20 wt % aqueous acetic acid for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid;

(f) quenching the neutralized slurry of step (e) with water to produce an aqueous spent acid mixture containing about 0.0-20 wt % aqueous acetic acid;

(g) separating the octahydro-1,3,5,7-tetranitro-1,3,5,7-tetrazocine and the ammonium nitrate from the anhydrous spent acid mixture of step (f);

(h) stirring the octahydro-1,3,5,7-tetranitro-1,3,5,7-tetrazocine from step (g) in a 0.0-90 wt % nitric acid solution at reflux to destroy undesired linear nitramines to provide crude octahydro-1,3,5,7-tetranitro-1,3,5,7-tetrazocine; and (i) collecting the crude octahydro-1,3,5,7-tetranitro-1,3,5,7-tetrazocine from step (h) by filtration.

In further embodiments, the present invention provides for a methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising any one of, or any combination of two or more of the following steps (a) through (i):

(a) (stage 1) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) (stage 2) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) (stage 3) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1,3,5,7-tetranitro-1,3,5,7-tetrazocine;

(d) (age stage) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid;

(f) quenching the neutralized slurry of step (e) with water to produce an aqueous spent acid mixture containing about 0.0-20 wt % aqueous acetic acid;

(g) separating the octahydro-1,3,5,7-tetranitro-1,3,5,7-tetrazocine and the ammonium nitrate from the anhydrous spent acid mixture of step (f);

(h) stirring the octahydro-1,3,5,7-tetranitro-1,3,5,7-tetrazocine from step (g) in a 0.0-90 wt % nitric acid solution at reflux to destroy undesired linear nitramines to provide crude octahydro-1,3,5,7-tetranitro-1,3,5,7-tetrazocine; and (i) collecting the crude octahydro-1,3,5,7-tetranitro-1,3,5,7-tetrazocine from step (h) by filtration.

In further embodiments, the present invention provides a methanoic acid free process with a quench to about 0-20 wt % aqueous acetic acid comprising the further step of washing the octahydro-1,3,5,7-tetranitro-1,3,5,7-tetrazocine separated from step (g) with hot water to produce washed octahydro-1,3,5,7-tetranitro-1,3,5,7-tetrazocine prior to proceeding to step (h).

In further embodiments, the present invention provides a methanoic acid free process with a quench to about 0-20 wt % aqueous acetic acid comprising the further step (j) of washing the crude octahydro-1,3,5,7-tetranitro-1,3,5,7-tetrazocine from step (i) is washed with water.

In further embodiments, the present invention provides a methanoic acid free process with a quench to about 0-20 wt % aqueous acetic acid comprising the further step (k), or the further step (l) of recrystallizing the washed, or unwashed octahydro-1,3,5,7-tetranitro-1,3,5,7-tetrazocine from step (j) or from step (i) respectively.

In further embodiments, the present invention provides a methanoic acid free process with a quench to about 0-20 wt % aqueous acetic acid wherein the recrystallization is from a solvent selected from the group consisting of acetone, cyclohexanone, water, dimethyl sulfoxide (DMSO), dimethylformamide (DMF), dimethylacetamide (DMAc), N-methylpyrrolidone (NMP), 2-Methylcyclohexanone, cyclohexyne, formamide, γ-butyrolactone, γ-valerolactone, δ-valerolactone, ε-caprolactone, and mixtures thereof.

In further embodiments, the present invention provides a methanoic acid free process with a quench to about 0-20 wt % aqueous acetic acid comprising the further step (l) of recrystallizing the washed or unwashed octahydro-1,3,5,7-tetranitro-1,3,5,7-tetrazocine from step (i) from a mixture of water and acetone.

In further embodiments, the present invention provides a methanoic acid free process with a quench to about 0-20 wt % aqueous acetic acid wherein the ammonia source of step (e) is ammonium acetate.

In further embodiments, the present invention provides a methanoic acid free process with a quench to about 0-20 wt % aqueous acetic acid wherein step (e) is performed by first cooling the slurry to about 20-60° C. prior to adding the ammonia or ammonia source.

In further embodiments, the present invention provides a methanoic acid free process with a quench to about 0-20 wt % aqueous acetic acid wherein step (e) is performed by first cooling the slurry to about 25-55° C. prior to adding the ammonia or ammonia source.

In further embodiments, the present invention provides a methanoic acid free process with a quench to about 0-20 wt % aqueous acetic acid wherein step (e) is performed by first cooling the slurry to about 45° C. prior to adding the ammonia or ammonia source.

In further embodiments, the present invention provides a methanoic acid free process with a quench to about 0-20 wt % aqueous acetic acid wherein in step (g) the mixture is subsequently cooled or warmed to about 20-90° C. prior to filtration.

In further embodiments, the present invention provides a methanoic acid free process with a quench to about 0-20 wt % aqueous acetic acid wherein in step (g) the mixture is subsequently cooled or warmed to about 20-50° C. prior to filtration.

In further embodiments, the present invention provides a methanoic acid free process with a quench to about 0-20 wt % aqueous acetic acid wherein in step (g) the mixture is subsequently cooled to about 25° C. prior to filtration.

In further embodiments, the present invention provides a methanoic acid free process with a quench to about 0-20 wt % aqueous acetic acid wherein in step (a) the temperature is maintained at about 40-75° C.

In further embodiments, the present invention provides a methanoic acid free process with a quench to about 0-20 wt % aqueous acetic acid wherein in step (a) the temperature is maintained at about 44° C.

In further embodiments, the present invention provides a methanoic acid free process with a quench to about 0-20 wt % aqueous acetic acid wherein in step (b) the slurry is maintained at about 40-75° C.

In further embodiments, the present invention provides a methanoic acid free process with a quench to about 0-20 wt % aqueous acetic acid wherein in step (b) the slurry is maintained at about 44° C.

In further embodiments, the present invention provides a methanoic acid free process with a quench to about 0-20 wt % aqueous acetic acid wherein in step (h) the washed or unwashed octahydro-1,3,5,7-tetranitro-1,3,5,7-tetrazocine from step (g) is stirred in about 0-60 wt % nitric acid solution.

In further embodiments, the present invention provides a methanoic acid free process with a quench to about 0-20 wt % aqueous acetic acid wherein in step (h) the washed or unwashed octahydro-1,3,5,7-tetranitro-1,3,5,7-tetrazocine from step (g) is stirred in about 0-40 wt % nitric acid solution.

In further embodiments, the present invention provides a methanoic acid free process with a quench to about 0-20 wt % aqueous acetic acid wherein in step (h) the washed or unwashed octahydro-1,3,5,7-tetranitro-1,3,5,7-tetrazocine from step (g) is stirred in about 0-10 wt % nitric acid solution.

In further embodiments, the present invention provides a methanoic acid free process with a quench to about 0-20 wt % aqueous acetic acid wherein the resultant aqueous filtrate from step (g) is directed to the pre-distillation evaporators followed by azeotropic distillation to separate acetic acid from water.

In further embodiments, the present invention provides a methanoic acid free process with a quench to about 0-20 wt % aqueous acetic acid wherein while maintaining a temperature of about 20-45° C., to a standard starting heel, containing a mixture comprising a majority of acetic acid with acetic anhydride, are added 0.0-0.10× moles 1,3,5,7-tetraazatricyclo[3.3.1.1$^{3,7}$]decane, 0.0×-0.20× moles ammonium nitrate and 0.0-0.20× moles nitric acid prior to commencing step (a);

In further embodiments, the present invention provides a methanoic acid free process with a quench to about 0-20 wt % aqueous acetic acid wherein while maintaining a temperature of about 20-45° C., to a standard starting heel, containing a mixture comprising a majority of acetic acid with acetic anhydride, are added 0.10×-0.20× moles 1,3,5,7-tetraazatricyclo[3.3.1.1$^{3,7}$]decane, 0.20×-0.40× moles ammonium nitrate and 0.20×-0.40× moles nitric acid prior to commencing step (a);

In further embodiments, the present invention provides a methanoic acid free process with a quench to about 0-20 wt % aqueous acetic acid wherein while maintaining a temperature of about 20-45° C., to a standard starting heel, containing a mixture comprising a majority of acetic acid with acetic anhydride, are added 0.20×-0.30× moles 1,3,5,7-tetraazatricyclo[3.3.1.1$^{3,7}$]decane, 0.40×-0.60× moles ammonium nitrate and 0.40×-0.60× moles nitric acid prior to commencing step (a);

In further embodiments, the present invention provides a methanoic acid free process with a quench to about 0-20 wt % aqueous acetic acid wherein while maintaining a temperature of about 20-45° C., to a standard starting heel, containing a mixture comprising a majority of acetic acid with acetic anhydride, are added 0.30×-0.40× moles 1,3,5,7-tetraazatricyclo[3.3.1.1$^{3,7}$]decane, 0.60×-0.80× moles ammonium nitrate and 0.60×-0.80× moles nitric acid prior to commencing step (a);

In further embodiments, the present invention provides a methanoic acid free process with a quench to about 0-20 wt % aqueous acetic acid wherein while maintaining a temperature of about 20-45° C., to a standard starting heel, containing a mixture comprising a majority of acetic acid with acetic anhydride, are added 0.40×-0.50× moles 1,3,5,7-tetraazatricyclo[3.3.1.1$^{3,7}$]decane, 0.80×-1.0× moles ammonium nitrate and 0.80×-1.0× moles nitric acid prior to commencing step (a);

In further embodiments, the present invention provides a methanoic acid free process with a quench to about 0-20 wt % aqueous acetic acid wherein in step (d), at 0-15 minutes of the 45 minute hold time, 0.0-2.0× moles of nitric acid are added while maintaining the temperature at 30-80° C.;

In further embodiments, the present invention provides a methanoic acid free process with a quench to about 0-20 wt % aqueous acetic acid wherein in step (d), at 15-30 minutes of the 45 minute hold time, 0.0-2.0× moles of nitric acid are added while maintaining the temperature at 30-80° C.;

In further embodiments, the present invention provides a methanoic acid free process with a quench to about 0-20 wt % aqueous acetic acid wherein in step (d), at 30-45 minutes of the 45 minute hold time, 0.0-2.0× moles of nitric acid are added while maintaining the temperature at 30-80° C.

In further embodiments, the present invention provides a methanoic acid free process with a quench to about 0-20 wt % aqueous acetic acid wherein in step (a), the ammonium nitrate is replaced with sodium nitrate.

In further embodiments, the present invention provides a methanoic acid free process with a quench to about 0-20 wt % aqueous acetic acid wherein in step (b), the ammonium nitrate is replaced with sodium nitrate.

In further embodiments, the present invention provides a methanoic acid free process with a quench to about 0-20 wt % aqueous acetic acid wherein in step (c), the ammonium nitrate is replaced with sodium nitrate.

In further embodiments, the present invention provides a methanoic acid free process with a quench to about 0-20 wt % aqueous acetic acid while maintaining a temperature of about 20-45° C., adding the full quantity of 1,3,5,7-tetraaza-tricyclo[3.3.1.1$^{3,7}$]decane in acetic acid (x moles of 1,3,5, 7-tetraazatricyclo[3.3.1.1$^{3,7}$]decane) to a starting standard heel containing a mixture comprising a majority of acetic acid with acetic anhydride, while maintaining a temperature of about 20-45° C., to the mixture is added ammonium nitrate (1.0×-2.0×) and nitric acid (1.0×-2.0×) prior to commencing step (a). The 1,3,5,7-tetraazatricyclo[3.3.1.1$^{3,7}$]decane in acetic acid feed stream 1 and ammonium nitrate in nitric acid feed stream 2 reduced to zero mass added during step (a). Alternatively, replace ammonium nitrate with sodium nitrate accounting for mole equivalents.

These and other embodiments of the present invention will become apparent from the disclosure herein.

BRIEF DESCRIPTION OF THE DRAWINGS

Figure 12B:
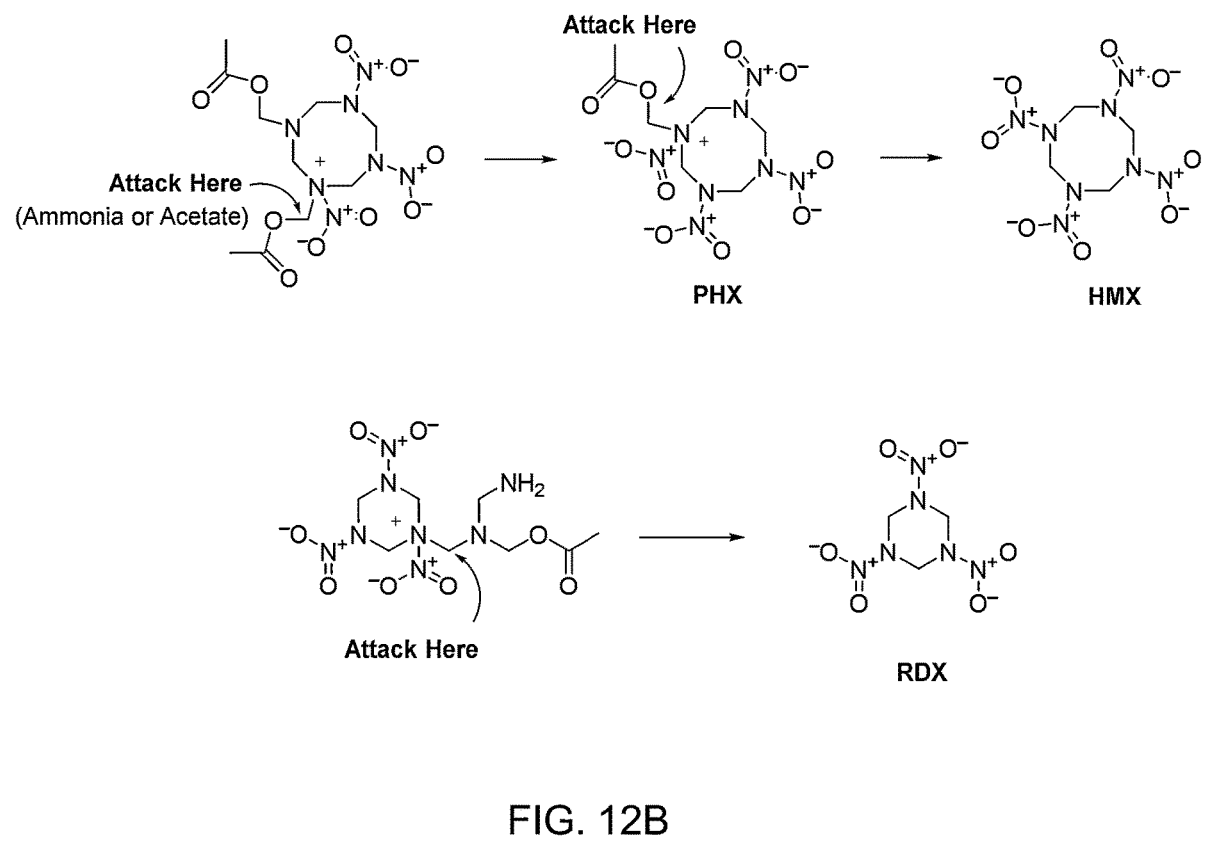
Figure 12D:
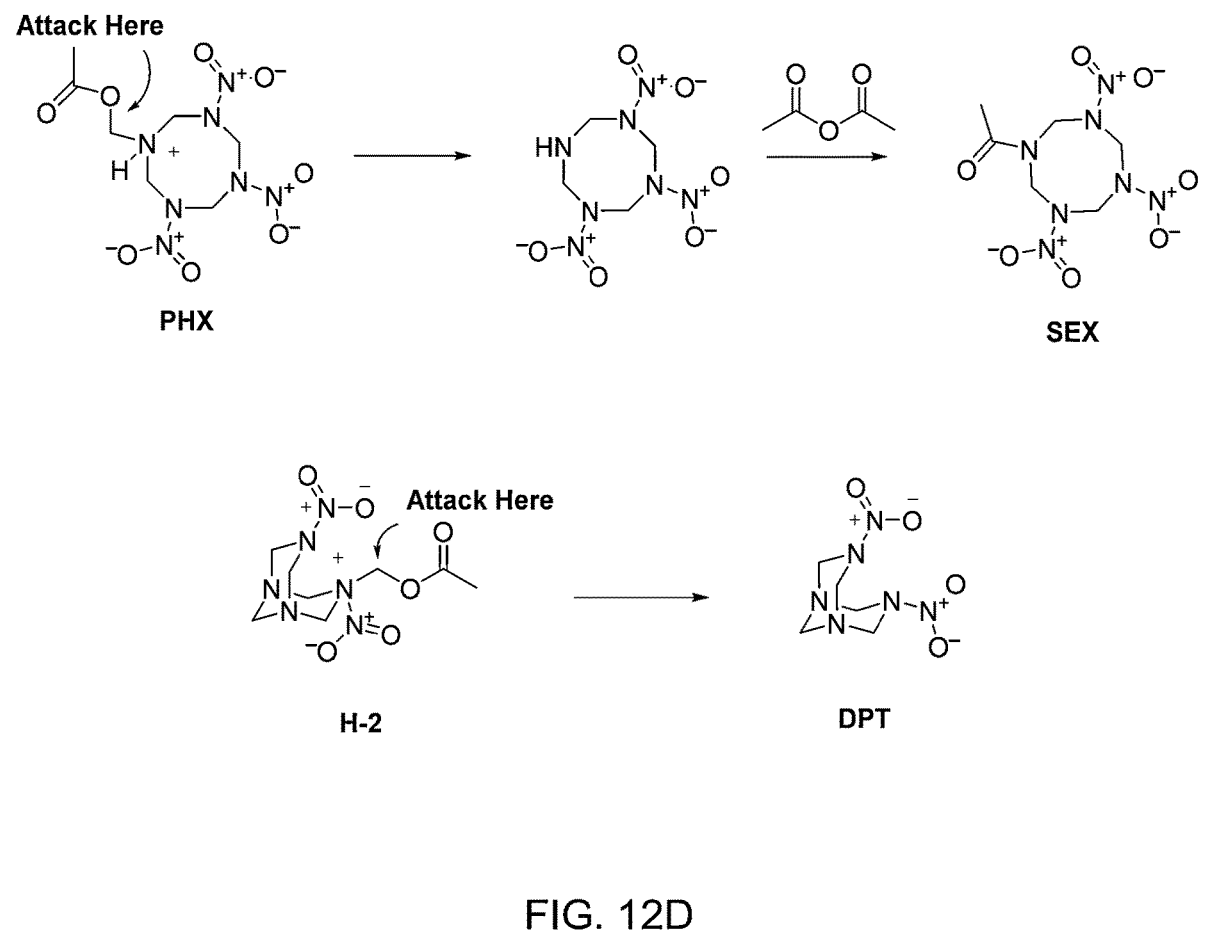

FIGS. 12A, 12B, 12C, and 12D provide an illustrative and nonlimiting mechanistic chemical rationale for the Example 18. for the Octahydro-1,3,5,7-tetranitro-1,3,5,7-tetrazocine modification where the ammonium nitrate is replaced with sodium nitrate.

DETAILED DESCRIPTION

Definitions

Figure 1:
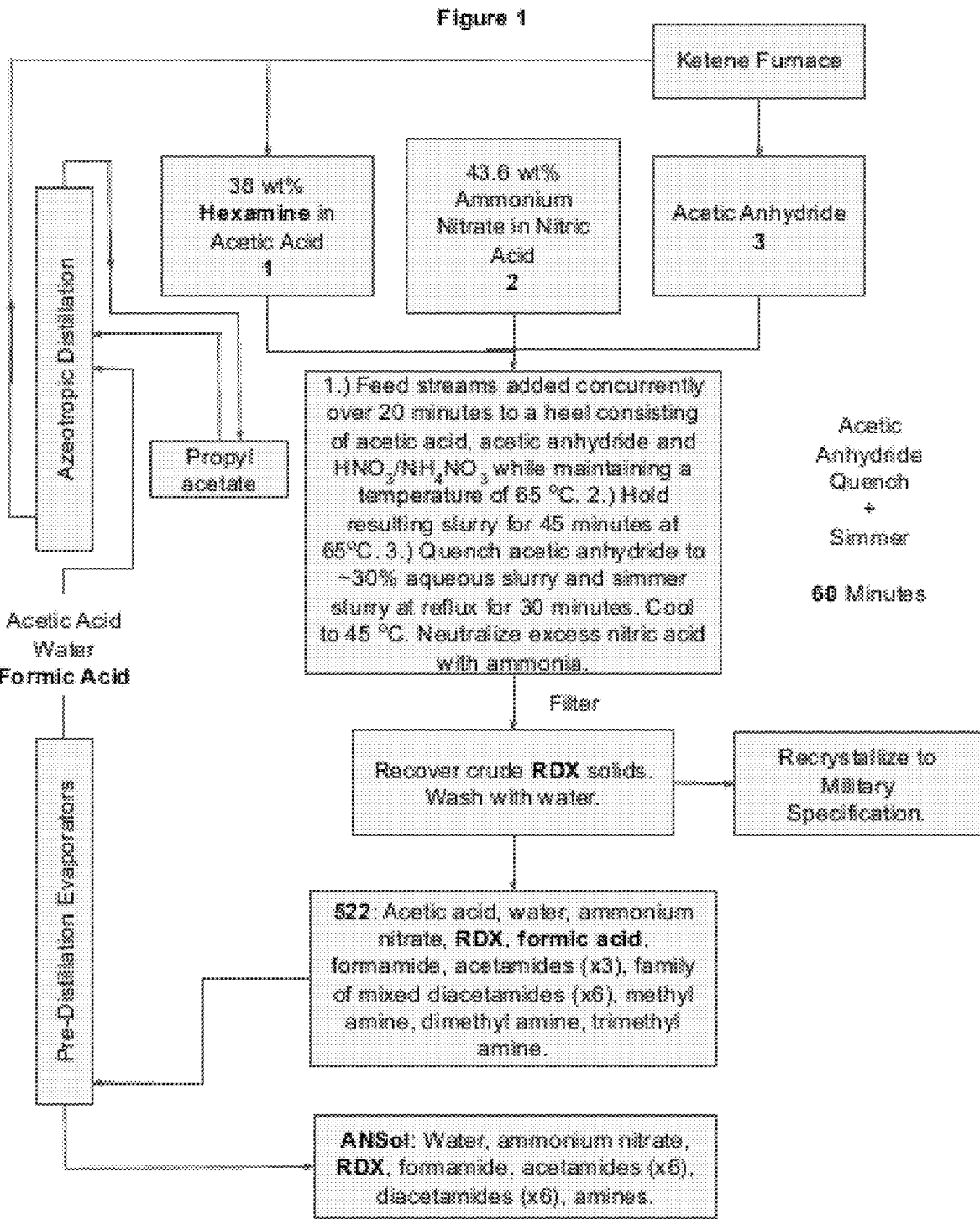
FIG. 1—Conventional process for making hexahydro-1, 3,5-trinitro-1,3,5-triazine.

The term "RDX" is another name for hexahydro-1,3,5-trinitro-1,3,5-triazine corresponding to the CAS registry number 121-82-4.

The term "HMX" is another name for octahydro-1,3,5,7-tetranitro-1,3,5,7-tetrazocine corresponding to the CAS registry number 2691-41-0.

The terms "1,3,5,7-tetraazatricyclo[3.3.1.1$^{3,7}$]decane", "hexamine", "hexamethylenetetramine", "methenamine", "formin", "aminoform" and "urotropine" are synonyms for the chemical compound having the IUPAC name 1,3,5,7-tetraazaadamantane, corresponding to CAS registry number 100-97-0.

The term methanoic acid free, as used herein means that the processes for producing RDX and/or HMX generate substantially no methanoic acid, which is also known as formic acid. The processes generally provide no detectable levels of methanoic acid, The typical RDX waste stream contains about 0.15-0.20 wt % formic acid. The typical HMX waste stream contains about 0.35-0.45 wt %. In the present invention, generally, the formic acid is reduced from the conventional processes by ≥90%. For example, in some embodiments of the processes of the present invention with respect to RDX, the residual methanoic acid is below about 0.02% by weight. For example, in some embodiments of the processes of the present invention with respect to HMI-4X, the residual methanoic acid is below about 0.045% by weight. Although a definitive lower range of residual methanoic acid is not necessarily defined, a targeted amount can be on the order of 0.01% or less or essentially below the level of detection of common analytical methods normally employed.

The term "standard heel" refers to the combination of chemicals and solvents present in the reactor or tank heel for the RDX and HMX processes prior to the addition of Feed Streams A, B and C. The heel refers to the volume at the lowest operable level.

The term "starting standard heel" refers to the initial heel that is prepared at the beginning of the processes of the present invention. In other words, a "starting standard heel" is the heel that is normally formed with the Legacy Bachmann RDX Process and The Legacy Bachmann HMX process. They are different. For RDX the "starting standard heel" is acetic acid/acetic anhydride/nitric acid/ammonium nitrate. For HMX claims, the "starting standard heel" is acetic acid/acetic anhydride.

Methanoic Acid Free Nitramine Production Process

As presented above, the present invention provides improved nitrolysis processes for making the explosive compounds hexahydro-1,3,5-trinitro-1,3,5-triazine and octa-hydro-1,3,5,7-tetranitro-1,3,5,7-tetrazocine. Unlike prior conventional large-scale manufacturing processes, these processes of the present invention have the advantage of being substantially-free of methanoic acid.

The present processes are achieved by a controlled quench of acetic anhydride to an anhydrous state, neutral-ization of nitric acid, without application of heat to the resultant product mixture to eliminate levels of excess water while reducing residual levels of remaining acetic anhy-dride, and also by neutralizing excess nitric acid remaining in the resultant product mixture.

The following are some aspects of the processes of the present invention:

a.) No aqueous acetic acid simmer step.

b.) The aqueous nitric acid solution used to remove the linear nitramines from the crude solids is filtered and recycled to the next batch.

c.) The spent acid filtrate recovered from the crude filtration can be recycled through the pre-distillation columns, or recycled directly to the next nitration and hexamine dissolution, or the unquenched (no acetic quench) filtrate can be azeotropically distilled to yield clean acetic acid and acetic anhydride. In other words, the residual acetic anhydride is recovered for recycling back into the process.

d.) The ANSol recovered from the pre-distillation evaporator bottoms can be recycled back to the crude filtration step. And, e.) Throughput times are reduced with the removal of the simmer step.

Variants for the Processes

The processes of the present invention for preparing RDX and HMX can encompass many variations. Some of these, which are contemplated as being nonlimiting, are described as follows.

RDX Variables

1. RDX process.
   a. Concurrent addition of feed streams A, B and C followed by an age step.
   b. Neutralize Nitric Acid.
   c. Quench Acetic Anhydride to 0.0-0.50 wt %.
   d. Filter crude RDX solids. Filtrate is anhydrous spent acid.
   e. Stir crude solids in 0.0-90 wt % Nitric Acid at 98-100° C. for 15-60 minutes to destroy linear nitramines.
   f. Filter the solids from the 0.0-90 wt % nitric acid and recrystallize via the legacy process.
   g. Run the anhydrous spent acid through the pre-distillation evaporators to complete the process cycle. (This clean, anhydrous acetic acid will be distributed to hexamine dissolution, nitration heel, and ketene furnaces.)

2. Anhydrous Spent Acid is recycled directly to hexamine dissolution and subsequent nitration heel. No pre-distillation evaporators. The ammonium nitrate present in the directly recycled spent acetic acid is accounted for and the amount of ammonium nitrate added to the subsequent nitration heel is adjusted to keep the standard starting heel conditions the same from batch to batch.

Example (assuming 1.0 wt % ammonium nitrate recycled acetic acid): 451.4 g acetic acid added to the heel. 451.4*0.01=4.51 g ammonium nitrate (note that the asterisk indicates a multiplication and is used at other places similarly in this document). 152.4 g of a 38 wt % 1,3,5,7-tetraazatricyclo[3.3.1.13,7]decane solution in acetic acid added via the feed stream. 0.62*152.4*0.01=0.94 g ammonium nitrate. 5.45 g (0.067 mol) total ammonium nitrate added to the heel from recycled acetic acid and 1,3,5,7-tetraazatricyclo[3.3.1.13,7]decane feed stream. Standard heel contains 11.8 g ammonium nitrate. 11.80-5.45=6.35 g ammonium nitrate to be added to the recycled heel.

3. Recycle Anhydrous Spent Acid to Heel Only. Only recycled to the subsequent nitration heel, and not the hexamine dissolution. Account for ammonium nitrate brought forward. Why? I'm not sure the Army is going to allow spent acid that has not been distilled in some fashion to be used in the hexamine dissolution. Hedging my bets here.

4. Do not Neutralize Nitric Acid. Do not Quench Acetic Anhydride. Recycle untreated spent acid directly to subsequent nitration heel. Account for ammonium nitrate, nitric acid and acetic anhydride brought forward when setting the standard starting heel. Neutralize remaining spent acid and run through pre-distillation evaporators and azeotropic columns to separate acetic anhydride from acetic acid.

Example (assuming 1.0 wt % ammonium nitrate, assuming 2.5 wt % nitric acid, assuming 4.0 wt % acetic anhydride): 451.4 g acetic acid added to the heel. 451.4*0.01=4.51 g ammonium nitrate. 451.4*0.025=11.29 g nitric acid. 451.4*0.040=18.06 g acetic anhydride. Standard heel contains 11.80 g ammonium nitrate, 15.2 g nitric acid and 21.9 g acetic anhydride. To the heel from untreated, recycled acetic acid (nitric acid not neutralized, acetic anhydride not quenched) is added 11.80-4.51=7.29 g ammonium nitrate, 15.20-11.29=3.91 g nitric acid and 21.90-18.06=3.84 g acetic anhydride to be added to the recycled heel.

5. Same as 4. The portion not utilized in the heel is neutralized and quenched and used in the hexamine dissolution. The remaining spent acid run through the pre-distillation evaporators and then the ketene furnaces.

6. Quench with water to 35 wt % aqueous acetic acid. Process the filtrate through the pre-distillation evaporators then the azeotropic distillation columns to separate the acetic acid and water from each other.

7. Neutralize Nitric Acid. Do not Quench Acetic Anhydride. Recycle to subsequent nitration heel only and account for ammonium nitrate and acetic anhydride brought forward when setting the standard starting heel. Remaining spent acid processed through the pre-distillation columns and azeotropic columns to separate acetic anhydride from acetic acid.

8. Do Not Neutralize Nitric Acid. Quench Acetic Anhydride. Recycle to subsequent nitration heel only and account for nitric acid and ammonium nitrate brought forward when setting the standard starting heel. Neutralize remaining spent acid and recycle to hexamine heel and/or pre-distillation evaporators.

9. Add 0.0-2.0 Equiv. Nitric Acid during the 45 minute age step. Add quantity of nitric acid (0.0-2.0 equivalents relative to the amount of hexamine added in Feed Stream 1) at 0-15 minutes of the 45 minutes age step, or at 15-30 minutes of the 45 minutes age step, or at 30-45 minutes of the 45 minutes age step.

Reaction Product Streams

The following are an embodiment of the reaction product streams for RDX.

To a starting standard heel consisting of approximately 451.4 g acetic acid, approximately 21.9 g acetic anhydride, approximately 11.8 g ammonium nitrate and approximately 15.2 g nitric acid, is added concurrently. These amounts are for a typical laboratory scale, but the practitioner can appreciate appropriately scaling up for larger production amounts, also accounting for minimum stir and heel volumes.

Feed Stream 1: 152.38 g of a solution of 38 wt % 1,3,5,7-tetraazatricyclo[3.3.1.1$^{3,7}$]decane in acetic acid, Feed Stream 2: 217.35 g of a solution of 43.6 wt % ammonium nitrate in nitric acid, and Feed Stream 3: 330.63 g acetic anhydride.

For example, the three streams added concurrently over 20 minutes while maintaining a temperature of 65° C.

For RDX, the three Feed Streams are typically added concurrently over a period of about 10 to about 30 minutes, 15 to about 25 minutes, and typically about 20 minutes. The rate of addition can be adjusted accordingly based upon the specific needs and variations decided in the process.

HMX Variables The heel conditions for HMX when ammonium nitrate is present calls for adding 0.50-1.0 equiv. of hexamine and 1.0 equiv. of nitric acid relative to the moles of ammonium nitrate carried forward to the heel via the recycled anhydrous acetic acid and/or the hexamine acetic acid feed stream.

1. HMX Process
    a. Stage 1
    b. Stage 2
    c. Stage 3, followed by an age step, which can range from about 30 minutes to about 60 minutes with a typical age time of about 45 minutes.
    d. Neutralize Nitric Acid.
    e. Quench Acetic Anhydride to 0.0-0.50 wt %.
    f. Filter crude HMX solids. Filtrate is anhydrous spent acid.
    g. Stir crude solids in 0.0-90 wt % Nitric Acid at 98-100° C. for 15-60 minutes to destroy linear nitramines.
    h. Filter the solids from the 0.0-90 wt % nitric acid and recrystallize via the legacy process.
    i. Run the anhydrous spent acid through the pre-distillation evaporators to complete the process cycle. This clean, anhydrous acetic acid will be distributed to hexamine dissolution, nitration heel, and ketene furnaces.
    1. Anhydrous Spent Acid is recycled directly to hexamine dissolution and/or subsequent nitration heel and/or pre-distillation evaporators. The ammonium nitrate present in the directly recycled spent acetic acid is accounted for. The standard heel conditions for HMX when ammonium nitrate is present calls for adding 0.50-1.0 equiv. of hexamine and 1.0 equiv. of nitric acid relative to the moles of ammonium nitrate carried forward to the heel via the recycled anhydrous acetic acid and/or the hexamine acetic acid feed stream.

Example (assuming 1.0 wt % ammonium nitrate recycled acetic acid): 437.6 g acetic acid added to the heel. 437.6*0.01=4.38 g ammonium nitrate. 152.4 g of a 38 wt % 1,3,5,7-Tetraazatricyclo[3.3.1.1$^{3,7}$]decane solution in acetic acid added via the feed stream. 0.62*152.4*0.01=0.94 g ammonium nitrate. 5.32 g (0.067 mol) total ammonium nitrate added to the heel/reaction. 4.22 g (0.067 mol) nitric acid and 4.69-9.38 g (0.034-0.067 mol) 1,3,5,7-Tetraazatricyclo[3.3.1.1$^{3,7}$]decane added to the recycled heel. (not applicable to processes run with virgin acetic acid.)

2. Hexamine Spike Heel. Neutralize nitric acid. Quench acetic anhydride. To a standard stating heel is added Hexamine (z moles), ammonium nitrate (1.0z-2.0z moles) and nitric acid (1.0z-2.0z moles) prior to commencing stage 1. No recycle to heel or hexamine. All spent acid to the pre-distillation evaporators.

3. Hexamine Spike Heel. Neutralize nitric acid. Quench acetic anhydride. To a standard stating heel is added Hexamine (z moles), ammonium nitrate (1.0z-2.0z moles) and nitric acid (1.0z-2.0z moles) prior to commencing stage 1. Spent acid is recycled directly to hexamine dissolution and/or subsequent nitration heel and/or the pre-distillation evaporators. The ammonium nitrate present in the directly recycled spent acetic acid to the heel and/or hexamine dissolution is accounted for, and the amount of ammonium nitrate added to the subsequent nitration heel is adjusted to keep the starting spiked heel conditions the same from batch to batch. The starting heel conditions for HMX when ammonium nitrate is present is different from the standard starting heel conditions for HMX when ammonium nitrate is not present.

Example: 25% 1,3,5,7-Tetraazatricyclo[3.3.1.13,7]decane heel (assuming 1.0 wt % ammonium nitrate recycled acetic acid): 437.6 g acetic acid added to the heel. 437.6*0.01=4.38 g ammonium nitrate. 152.4 g of a 38 wt % 1,3,5,7-Ttetraazatricyclo[3.3.1.13,7]decane solution in acetic acid added via the feed stream. 0.62*152.4*0.01=0.94 g ammonium nitrate. 5.32 g (0.067 mol) total ammonium nitrate added to the heel. A 25% 1,3,5,7-Tetraazatricyclo[3.3.1.13,7]decane heel requires 13.04 g nitric acid, 16.54 g ammonium nitrate, 14.48 g 1,3,5,7-Ttetraazatricyclo[3.3.1.13,7]decane. Accounting for ammonium nitrate brought forward in the recycled heel and recycled 1,3,5,7-Ttetraazatricyclo[3.3.1.13,7]decane solution feed stream, 13.04 g nitric acid, 11.22 g (16.54-5.32 g) ammonium nitrate, 14.48 g 1,3,5,7-Ttetraazatricyclo[3.3.1.13,7]decane added to the recycled heel at the start of the process.

4. Hexamine Spike Heel. Neutralize nitric acid. Do Not Quench acetic anhydride. To a standard starting heel is added Hexamine (z moles), ammonium nitrate (1.0z-2.0z moles) and nitric acid (1.0z-2.0z moles) prior to commencing stage 1. Spent Acid is processed through the pre-distillation evaporators then to the azeotropic distillation columns to separate acetic anhydride from the acetic acid.

5. Add 0.0-2.0 Equiv. Nitric Acid during the 45 minute age step. Add quantity of nitric acid (0.0-2.0 equivalents relative to the amount of hexamine added in Feed Stream 1) at 0-15 minutes of the 45 minutes age step, or at 15-30 minutes of the 45 minutes age step, or at 30-45 minutes of the 45 minutes age step.

6. Quench with water to 20 wt % aqueous acetic acid. Process the filtrate through the pre-distillation evaporators then the azeotropic distillation columns.

7. Neutralize Nitric Acid. Do Not Quench Acetic Anhydride. Spent Acid is processed through the pre-distillation evaporators then to the azeotropic distillation columns to separate acetic anhydride from the acetic acid. The ammonium nitrate and acetic anhydride present in the spent acid recycled to the heel is accounted for and adjustments made to ensure the starting standard heel conditions remain the same form batch to batch.

8. Charge All Reaction Hexamine to Heel. To a starting standard heel at 20-45° C. is added 152.4 g of a 38 wt % 1,3,5,7-Tetraazatricyclo[3.3.1.1$^{3,7}$]decane solution in acetic acid (0.414 moles of 1,3,5,7-Tetraazatricyclo[3.3.1.1$^{3,7}$]decane), ammonium nitrate (0.414 moles to 0.828 moles) and nitric acid (0.414 moles to 0.828 moles) prior to commencing stage 1 addition. During Stage 1, feed streams 1 and 2 having zero mass added and feed stream 3 performed as in the standard HMX process. Stage 2, and stage 3 and the age step performed as in the standard HMX process.

9. Replace Ammonium Nitrate with Sodium Nitrate. Replace ammonium nitrate with an equimolar amount of sodium nitrate. Sodium nitrate can be replaced with an equimolar amount of an appropriate metal salt of nitric acid.

10. Nitric Acid Neutralized. Do Not Quench Acetic Anhydride. Recycle to heel only. Account for ammonium nitrate and acetic anhydride brought forward. Remaining spent acid is run through the pre-distillation evaporators then the azeotropic distillation columns. The standard heel conditions for HMX when ammonium nitrate is present calls for adding 0.50-1.0 equiv. of hexamine and 1.0 equiv. of nitric acid relative to the moles of ammonium nitrate carried forward to the heel via the recycled anhydrous acetic acid and/or the hexamine acetic acid feed stream. The amount of acetic anhydride brought forward to the subsequent nitration heel from the recycled spent acid to be determined and accounted for when determining the proper amount of acetic anhydride to add to the stating heel.

11. Do Not Neutralize Nitric Acid. Do Not Quench Acetic Anhydride. Recycle to heel only. Account for ammonium nitrate, nitric acid and acetic anhydride carried forward when setting the heel. Remaining spent acid neutralized and quenched and run through the pre-distillation evaporators and/or recycled to the hexamine dissolution. Ammonium nitrate content in the hexamine feed stream accounted for when setting the subsequent nitration heel.

Reaction Product Streams

The following are an embodiment of the reaction product streams for HMX.

To a standard starting heel consisting of approximately 437.6 g acetic acid and approximately 10.9 g acetic anhydride is added concurrently, Stage 1:

Feed Stream 1: 152.4 g of a 38 wt % 1,3,5,7-Tetraazatricyclo[3.3.1.1$^{3,7}$]decane solution in acetic acid.

Feed Stream 2: 94.9 g of a 43.6 wt % ammonium nitrate solution in nitric acid,

Feed Stream 3: 325.5 g of acetic anhydride

For HMX, the three Feed Streams for Stage 1 are typically added concurrently over a period of about 10 to about 30 minutes, 15 to about 25 minutes, and typically about 20 minutes. The rate of addition can be adjusted accordingly based upon the specific needs and variations decided in the process.

Stage 2:

Feed Stream 2: 26.9 g of 43.6 wt % ammonium nitrate solution in nitric acid,

Feed Stream 3: 96.9 g acetic anhydride.

For HMX, the two Feed Streams for Stage 2 are typically added concurrently over a period of about 2 to about 20 minutes, 5 to about 10 minutes, and typically about 7 minutes. The rate of addition can be adjusted accordingly based upon the specific needs and variations decided in the process.

Stage 3:

Feed Stream 2: 124.0 g 43.6 wt % ammonium nitrate in nitric acid,

Feed Stream 3: 352.3 g acetic anhydride

For HMX, the two Feed Streams for Stage 3 are typically added concurrently over a period of about 2 to about 20 minutes, 5 to about 10 minutes, and typically about 8 minutes. The rate of addition can be adjusted accordingly based upon the specific needs and variations decided in the process.

Experiments Investigating Recycling Acetic Anhydride at Concentrations Greater than 0.50 wt % in Acetic Anhydride.

1.) Make up a series solutions of wt % acetic anhydride in acetic acid. 0.50 to 20 wt % acetic anhydride in acetic acid graduated by increments of 0.25 wt %. (78 solutions)

2.) Make up 38 wt % hexamine solutions in the series of solvent systems created above. Allow resulting hexamine solutions to hold at 25° C. for 3 days.

3.) Run standard RDX reaction with the series of 38 wt % hexamine solutions. (78 reactions)

a.) Plot RDX yield against wt % acetic anhydride in acetic acid solution used in the respective 38 wt % hexamine feed streams. Determine if Military specification is met.

b.) Plot wt % HMX in RDX against wt % acetic anhydride in acetic acid solution used in the respective 38 wt % hexamine feed streams. Determine if Military specification is met.

4.) Run standard HMX reaction with the series of 38 wt % hexamine solutions. (78 reactions)

a.) Plot HMX yield against wt % acetic anhydride in acetic acid solution used in the respective 38 wt % hexamine feed streams. Determine if Military specification is met.

b.) Plot wt % RDX in HMX against wt % acetic anhydride in acetic acid solution used in the respective 38 wt % hexamine feed streams. Determine if Military specification is met.

EXAMPLES

The following examples further described and demonstrate embodiments within the scope of the present invention. The Examples are given solely for purpose of illustration and are not to be construed as limitations of the present invention, as many variations thereof are possible without departing from the spirit and scope of the invention.

Throughout this disclosure, all recited temperatures are the central point in a range of +/−5° C. and all recited times are the central point in a range of +/−5 minutes.

A. Prior Conventional Process
Hexahydro-1,3,5-trinitro-1,3,5-triazine

Referring to the flow diagram of the hexahydro-1,3,5-trinitro-1,3,5-triazine nitrolysis shown in FIG. 1, the three feed streams which are entered into the reactor are as follows (see U.S. Pat. No. 4,163,845, which provides a basis for the prior conventional process):

Feed Stream 1: 152.38 g of a solution of 38 wt % 1,3,5,7-tetraazatricyclo[3.3.1.1$^{3,7}$]decane in acetic acid, Feed Stream 2: 217.35 g of a solution of 43.6 wt % ammonium nitrate in nitric acid, and Feed Stream 3: 330.63 g acetic anhydride.

The Feed Streams were added concurrently over 20 minutes to an agitated reactor containing a heel maintained at 65° C. and consisting of 451.4 g acetic acid, 21.9 g acetic anhydride, 11.8 g ammonium nitrate and 15.2 g nitric acid. Following the addition of the reagent Feed Streams the resulting slurry is aged at 65° C. for 45 minutes to ensure completion of the nitrolysis. Upon completion of the nitrolysis step 575 g water is added at a rate to ensure the reaction slurry temperature does not exceed 69° C. The resulting aqueous acetic acid slurry is heated to 98-100° C. for 30 minutes to destroy undesired linear nitramines. The slurry is cooled to 45° C. and filtered. The solids are washed with water and dried. The filtrate is processed through pre-distillation evaporators to separate the volatile components from the nonvolatile components. The process stream consisting mainly of acetic acid, water and methanoic acid are directed to the pre-distillation evaporators, followed by the distillation facility for final processing to glacial acetic acid (containing methanoic acid as a minor component) to complete the process cycle. A portion of the glacial acetic acid is directed toward the ketene furnaces to regenerate acetic anhydride and complete the process cycle.

Figure 2:
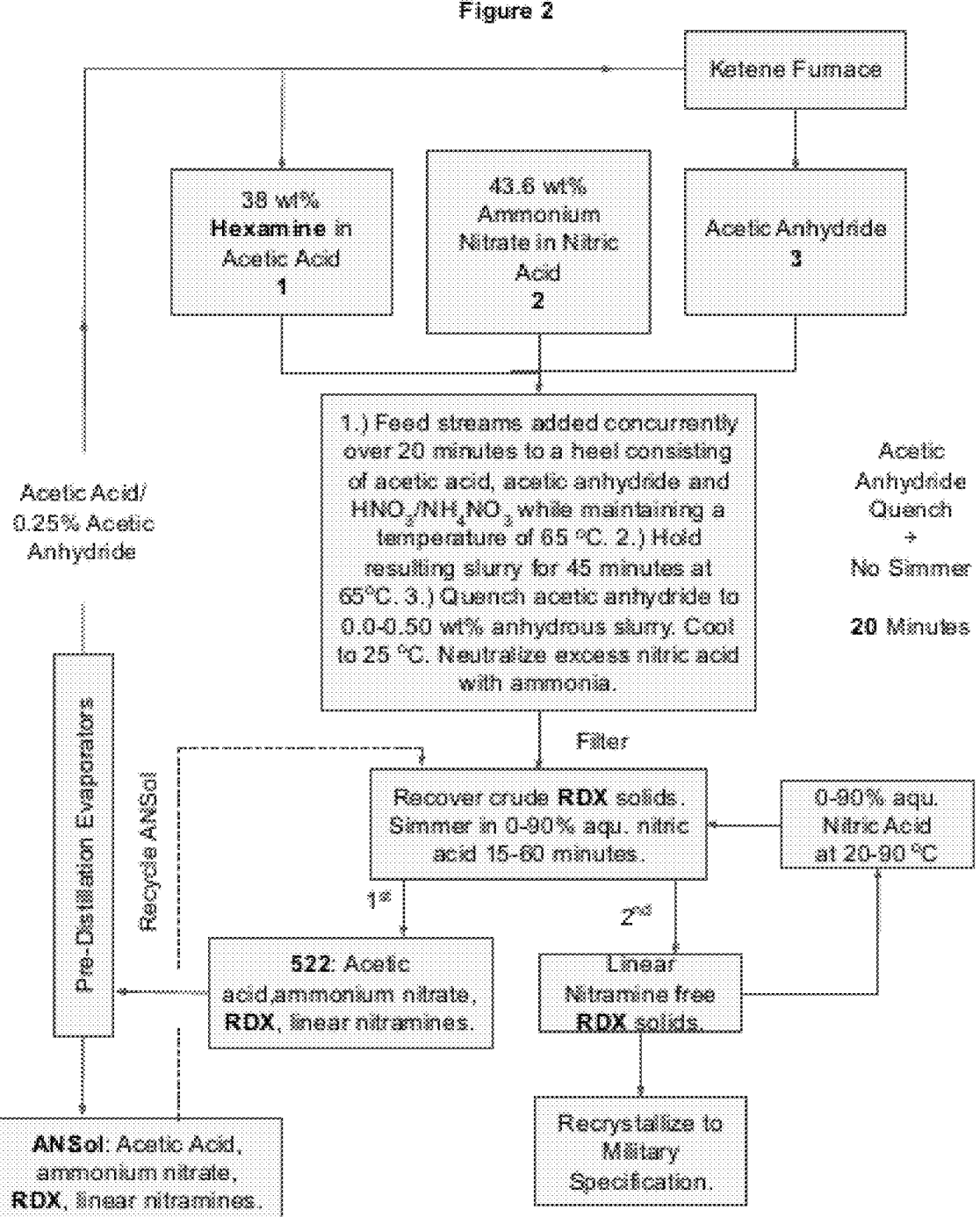
FIG. 2—Conventional hexahydro-1,3,5-trinitro-1,3,5-triazine process modified according to the present invention.

Example 1: Conventional Hexahydro-1,3,5-trinitro-1,3,5-triazine Process Modified According to the Present Invention-Spent Acid to the Pre-Distillation Evaporators Equivalent to the hexahydro-1,3,5-trinitro-1,3,5-triazine A. Conventional Process, above, through nitrolysis 45 minute age at 65° C.). Upon completion of the nitrolysis step at 65° C. for 45 minutes, the reaction slurry is cooled to 45° C. (25-55° C.) and treated with sufficient ammonia (ammonium acetate) to neutralize the excess nitric acid. Neutralization step can happen after filtration, and before evaporators. The reaction slurry is maintained below 60° C. (40-60° C.) during the ammonia addition. To the neutralized slurry is added sufficient water to adjust the acetic anhydride content to 0.0-0.50 wt %. The temperature is maintained below 60° C. (40-60° C.) during the water addition. The final slurry is cooled to 25° C. (20-50° C.) and filtered to the extent the majority of the acetic acid is recovered. No simmer step is required. The filtered solids are stirred in hot (>90° C.) 0.0-40% nitric acid and heated to reflux, and the new slurry stirred for 15-60 minutes at reflux, followed by cooling to 25° C. (20-60° C.) and filtering. The recovered solids are washed with water then recrystallized via the conventional process. The resulting solution recovered from the hot 0.0-40% nitric acid slurry of the filtered solids is recycled to subsequent crude filtered solids batch treatments. The anhydrous spent acid is directed to the pre-distillation evaporators to separate the volatile components from the nonvolatile components. An appropriate portion of the glacial acetic acid recovered from the pre-distillation evaporators (containing 0.0-0.50% acetic anhydride) is directed to the ketene furnaces to regenerate acetic anhydride to complete the recycle process. An appropriate portion of the glacial acetic acid recovered from the pre-distillation evaporators (containing 0.0-0.50% acetic anhydride) is directed toward the dissolution of 1,3,5,7-tetraazatricyclo[3.3.1.1$^{3,7}$]decane. The remaining glacial acetic acid recovered from the pre-distillation evaporators (containing 0.0-0.50% acetic anhydride) is directed to the heel of the subsequent nitrolysis batch. The ANSol recovered from the pre-distillation evaporators can be recycled to the initial crude hexahydro-1,3,5-trinitro-1,3,5-triazine filtration. See FIG. 2.

Example 2: Direct Recycle of Spent Acid Hexahydro-1,3,5-trinitro-1,3,5-triazine Modification with Quench. Recycle to Heel and 1,3,5,7-Tetraazatricyclo[3.3.1.1$^{3,7}$]decane Equivalent to the hexahydro-1,3,5-trinitro-1,3,5-triazine A. Conventional Process, above, through nitrolysis 45 minute age at 65° C. Upon completion of the nitrolysis step at 65° C. for 45 minutes, the reaction slurry is cooled to 45° C. (25-55° C.) and treated with sufficient ammonia (ammonium acetate) to neutralize the excess nitric acid. (Neutralization step can happen after filtration, and before evaporators.) The reaction slurry is maintained below 60° C. (40-60° C.) during the ammonia addition. To the neutralized slurry is added sufficient water to adjust the acetic anhydride content to 0.0-0.50 wt %. The temperature is maintained below 60° C. (40-60° C.) during the water addition. The final slurry is cooled to 25° C. (20-50° C.) and filtered to the extent the majority of the acetic acid is recovered. No simmer step is required. The filtered solids are stirred in hot (>90° C.) 0.0-40% nitric acid and heated to reflux, and the new slurry stirred for 15-60 minutes at reflux, followed by cooling to 25° C. (20-60° C.) and filtering. The recovered solids are washed with water then recrystallized via the conventional process. The resulting solution recovered from the hot 0.0-40% nitric acid slurry of the filtered solids is recycled to subsequent crude filtered solids batch treatments. An appropriate portion of the anhydrous spent acid (with 0.0-0.50% acetic anhydride and ~1.0-1.5 wt % ammonium nitrate present) is directed to the dissolution of 1,3,5,7-tetraazatricyclo[3.3.1.1$^{3,7}$]decane and the heel of the subsequent nitration batch. The amount of ammonium nitrate present (from the heel and 1,3,5,7-tetraazatricyclo[3.3.1.1$^{3,7}$ feed stream) is to be calculated and accounted for when setting the starting heel conditions. The remaining spent acid is sent to the pre-distillation evaporators to separate the volatile components from the nonvolatile components. An appropriate portion of the glacial acetic acid recovered from the evaporators (containing 0.0-0.50% acetic anhydride) is directed to the ketene furnaces to regenerate acetic anhydride to complete the recycle process. The ANSol recovered from the pre-distillation evaporators can be recycled to the initial crude hexahydro-1,3,5-trinitro-1,3,5-triazine filtration. See FIG. 3.

Example (assuming 1.0 wt % ammonium nitrate recycled acetic acid): 451.4 g acetic acid added to the heel. 451.4*0.01=4.51 g ammonium nitrate. 152.4 g of a 38 wt % 1,3,5,7-Tetraazatricyclo[3.3.1.1$^{3,7}$]decane solution in acetic acid added via the feed stream. 0.62*152.4*0.01=0.94 g ammonium nitrate. 5.45 g (0.067 mol) total ammonium nitrate added to the heel from recycled acetic acid and 1,3,5,7-Tetraazatricyclo[3.3.1.1$^{3,7}$]decane feed stream. Standard heel contains 11.8 g ammonium nitrate. 11.80-5.45=6.35 g ammonium nitrate to be added to the recycled heel.

Figure 3:
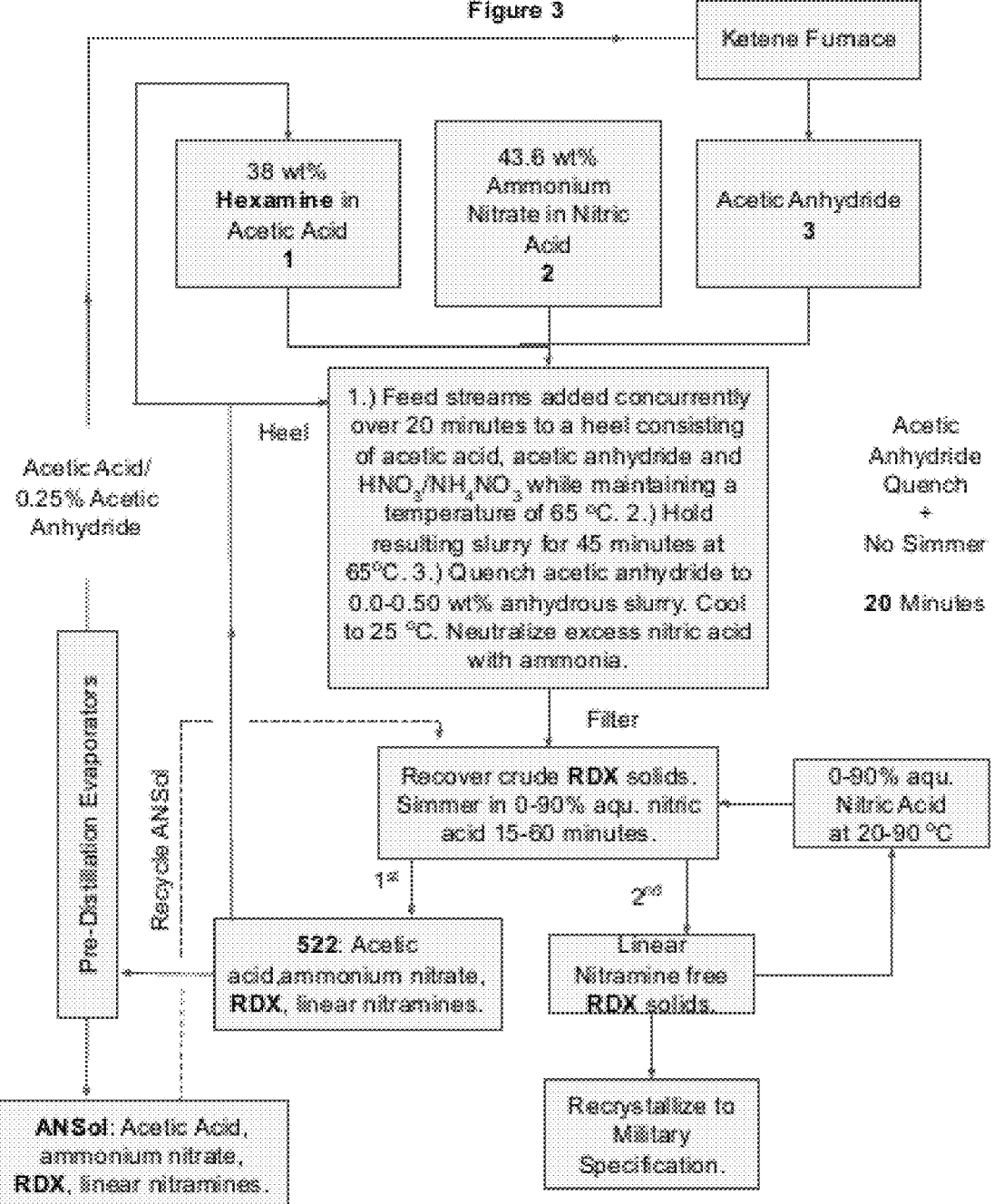
FIG. 3—Direct recycle of spent acid hexahydro-1,3,5-trinitro-1,3,5-triazine modification with quench and recycle to heel and 1,3,5,7-tetraazatricyclo[3.3.1.1$^{3,7}$]decane.

Example 3: Direct Recycle of Spent Acid Hexahydro-1,3,5-trinitro-1,3,5-triazine Modification with Quench. Recycle to Heel Equivalent to the hexahydro-1,3,5-trinitro-1,3,5-triazine A. Conventional Process, above, through nitrolysis 45 minute age at 65° C. Upon completion of the nitrolysis step at 65° C. for 45 minutes, the reaction slurry is cooled to 45° C. (25-55° C.) and treated with sufficient ammonia (ammonium acetate) to neutralize the excess nitric acid. Neutralization step can happen after filtration, and before evaporators. If recycling untreated spent acid to the 1,3,5,7-tetraazatricyclo[3.3.1.1$^{3,7}$]decane dissolution, then the nitric acid will need to have been quenched). The reaction slurry is maintained below 60° C. (40-60° C.) during the ammonia addition. To the neutralized slurry is added sufficient water to adjust the acetic anhydride content to 0.0-0.50 wt %. The temperature is maintained below 60° C. (40-60° C.) during the water addition. The final slurry is cooled to 25° C. (20-50° C.) and filtered to the extent the majority of the acetic acid is recovered. No simmer step is required. The filtered solids are stirred in hot (>90° C.) 0.0-40% nitric acid and heated to reflux, and the new slurry stirred for 15-60 minutes at reflux, followed by cooling to 25° C. (20-60° C.) and filtering. The recovered solids are washed with water then recrystallized via the conventional process. The resulting solution recovered from the hot 0.0-40% nitric acid slurry of the filtered solids is recycled to subsequent crude filtered solids batch treatments. An appropriate portion of the anhydrous spent acid (with 0.0-0.50% acetic anhydride and ~1.0-1.5 wt % ammonium nitrate present) is directed to the heel of the subsequent nitration batch. The amount of ammonium nitrate present is to be calculated and accounted for when setting the starting heel conditions. The remaining spent acid is sent to the pre-distillation evaporators to separate the volatile components from the nonvolatile components. An appropriate portion of the glacial acetic acid recovered from the evaporators (containing 0.0-0.50% acetic anhydride) is directed to the dissolution of 1,3,5,7-tetraazatricyclo [3.3.1.1$^{3,7}$]decane and ketene furnaces to regenerate acetic anhydride to complete the recycle process. The ANSol recovered from the pre-distillation evaporators can be recycled to the initial crude hexahydro-1,3,5-trinitro-1,3,5-triazine filtration. Analogous to what is shown in FIG. 3.

Figure 4:
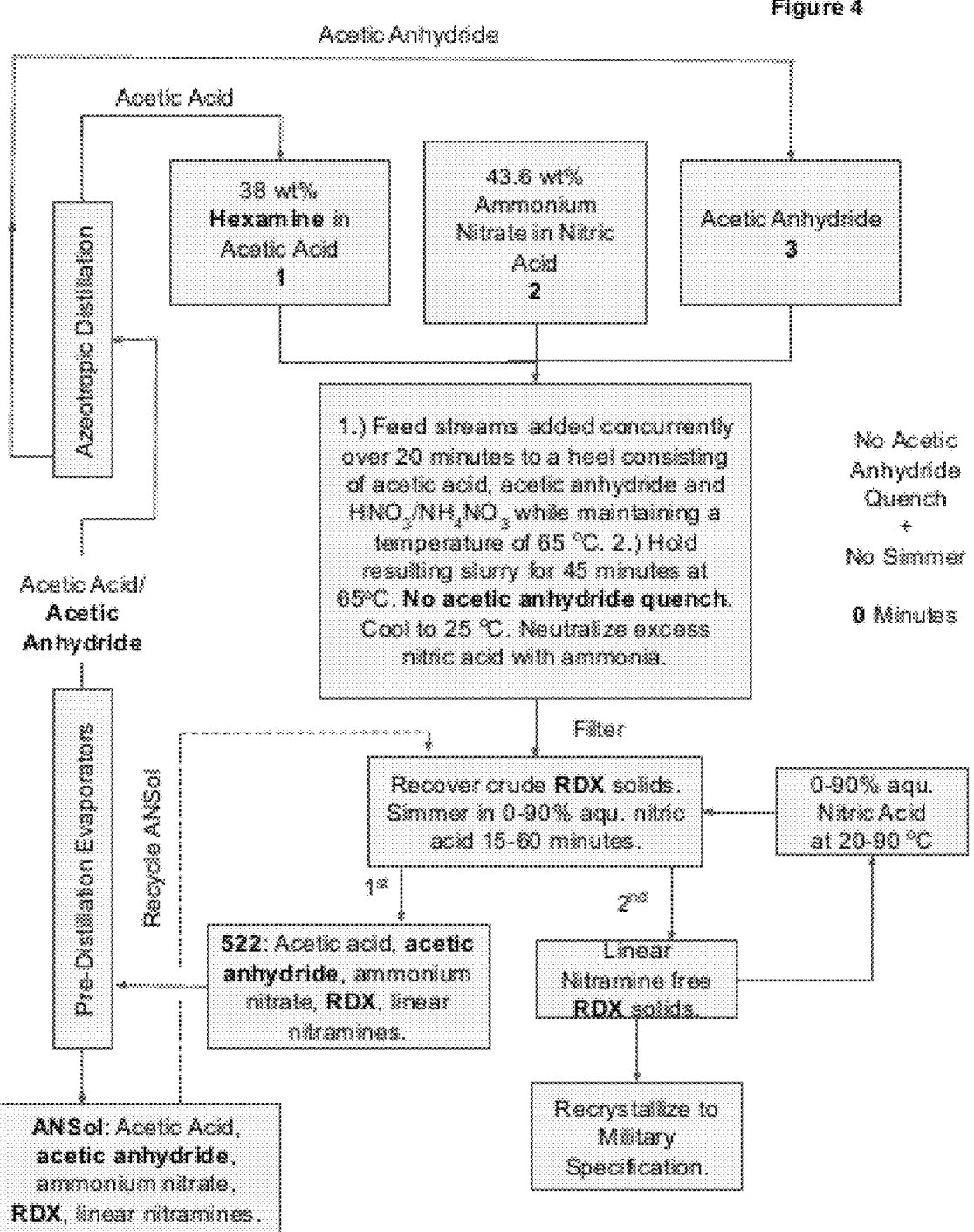
FIG. 4—Direct recycle of spent acid hexahydro-1,3,5-trinitro-1,3,5-triazine modification without quench.

Example 4: Direct Recycle of Spent Acid Hexahydro-1,3,5-trinitro-1,3,5-triazine Modification Without Quench or Neutralization Upon completion of the nitrolysis step at 65° C. for 45 minutes, the reaction slurry is cooled to 45° C. (25-55° C.) and filtered to the extent the majority of the acetic acid and acetic anhydride are recovered. The filtered solids are stirred in hot (>90° C.) 0.0-40% nitric acid and the new slurry stirred at reflux for 15-60 minutes, followed by cooling to 25° C. (20-60° C.) and filtering. The recovered solids are washed with water then recrystallized via the conventional process. The resulting solution recovered from the hot 0.0-40% nitric acid slurry of the filtered solids is recycled to subsequent crude filtered solids batch treatments. An appropriate portion of the anhydrous spent acid (without nitric acid neutralization, without acetic anhydride quench) is recycled to the subsequent nitration batch and the nitric acid, ammonium nitrate and acetic anhydride concentrations adjusted to the correct heel specification before commencing nitration. The remaining spent acid is neutralized with ammonia and sent to the pre-distillation evaporator/azeo columns to separate acetic acid from acetic anhydride. The ANSol recovered from the pre-distillation evaporators can be recycled to the initial crude Hexahydro-1,3,5-trinitro-1, 3,5-triazine filtration. Analogous to what is shown in FIG. 4.

Example (assuming 1.0 wt % ammonium nitrate, assuming 2.5 wt % nitric acid, assuming 4.0 wt % acetic anhydride): 451.4 g acetic acid added to the heel. 451.4*0.01=4.51 g ammonium nitrate. 451.4*0.025=11.29 g nitric acid. 451.4*0.040=18.06 g acetic anhydride. Standard heel contains 11.80 g ammonium nitrate, 15.2 g nitric acid and 21.9 g acetic anhydride. To the heel from untreated, recycled acetic acid (nitric acid not neutralized, acetic anhydride not quenched) is added 11.80-4.51=7.29 g ammonium nitrate, 15.20-11.29=3.91 g nitric acid and 21.90-18.06=3.84 g acetic anhydride to be added to the recycled heel.

Example 5: Direct Recycle of Spent Acid Hexahydro-1,3,5-trinitro-1,3,5-triazine Modification with 1,3,5,7-Tetraazatricyclo[3.3.1.1$^{3,7}$]decane Solvent Quenched Upon completion of the nitrolysis step at 65° C. for 45 minutes, the reaction slurry is cooled to 45° C. (25-55° C.)

and filtered to the extent the majority of the acetic acid is recovered. The filtered solids are stirred in hot (>90° C.) 0.0-40% nitric acid and heated to reflux, and the new slurry stirred at reflux for 15-60 minutes, followed by cooling to 25° C. (20-60° C.) and filtering. The recovered solids are washed with water then recrystallized via the conventional process. The resulting solution recovered from the hot 0.0-40% nitric acid slurry of the filtered solids is recycled to subsequent crude filtered solids batch treatments. A portion of the anhydrous spent acid (without nitric acid quench, without acetic anhydride quench) is recycled to the subsequent nitration batch and the nitric acid, ammonium nitrate and acetic anhydride concentrations adjusted to the correct heel specification before commencing nitration. An appropriate portion of the anhydrous spent acid neutralized with ammonia and quenched with water to 0.0-0.50 wt % acetic anhydride and used in the dissolution of 1,3,5,7-Tetraazatricyclo[3.3.1.1$^{3,7}$]decane. The remaining spent acid is neutralized with ammonia and sent to the pre-distillation evaporator/azeo columns to separate acetic acid from acetic anhydride. The ANSol recovered from the pre-distillation evaporators can be recycled to the initial crude hexahydro-1,3,5-trinitro-1,3,5-triazine filtration. Analogous to what is shown in FIG. 4.

Figure 5:
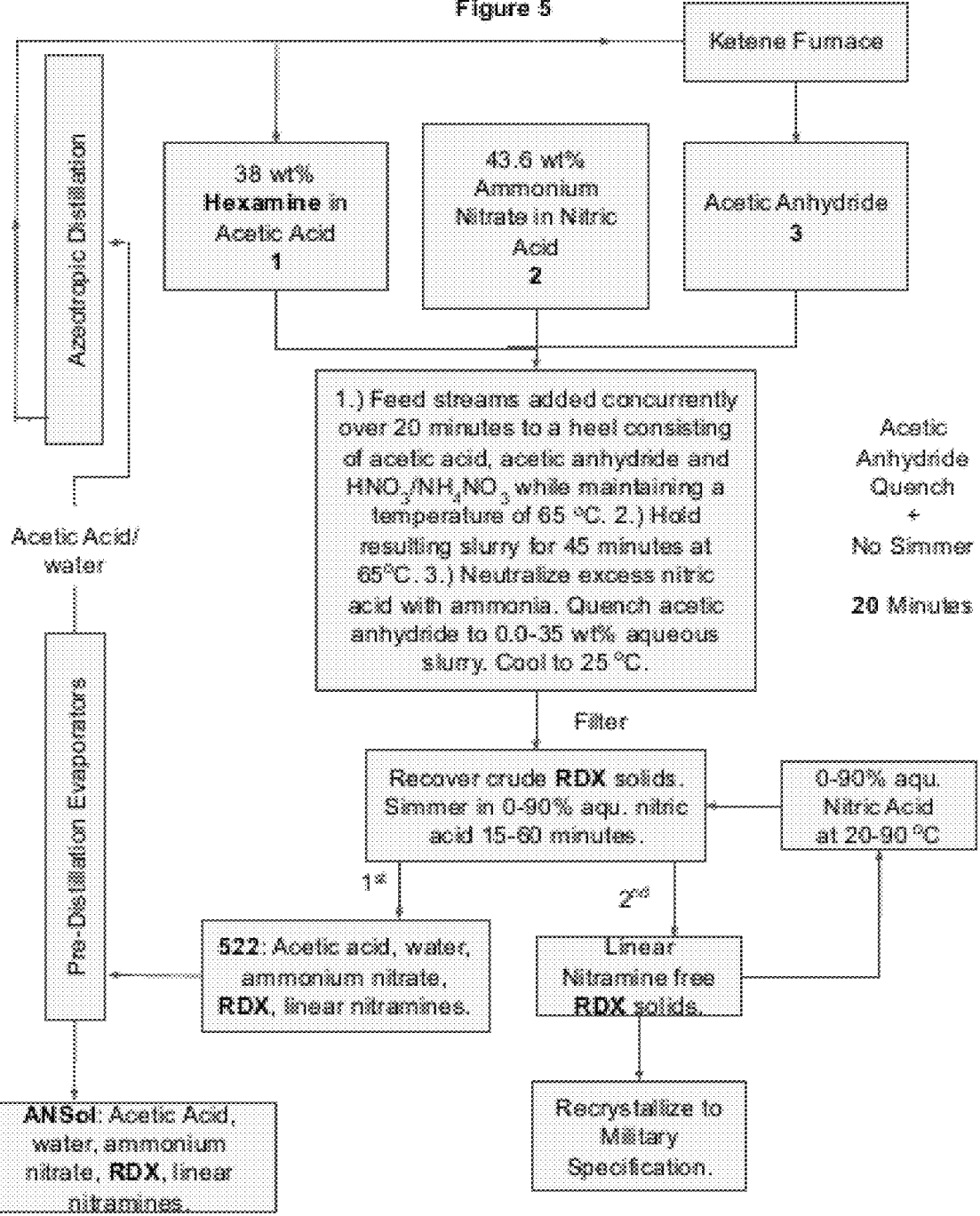
FIG. 5—Hexahydro-1,3,5-trinitro-1,3,5-triazine modified process with complete acetic anhydride quench to aqueous spent acid.

Example 6: Hexahydro-1,3,5-trinitro-1,3,5-triazine Modified Process with Complete Acetic Anhydride Quench Equivalent to the hexahydro-1,3,5-trinitro-1,3,5-triazine A. Conventional Process, above, through nitrolysis 45 minute age at 65° C. Upon completion of the nitrolysis step at 65° C. for 45 minutes, the reaction slurry is cooled to 45° C. (25-55° C.) and treated with sufficient ammonia (ammonium acetate) to neutralize the excess nitric acid. (Neutralization step can happen after filtration, and before evaporators). The reaction slurry is maintained below 60° C. (40-60° C.) during the ammonia addition. To the neutralized slurry is added sufficient water to fully quench the acetic anhydride and adjust the water content to 0.0-35 wt %. The temperature is maintained below 60° C. (40-60° C.) during the water addition. The final slurry is cooled to 25° C. (20-50° C.) and filtered. The filter cake is washed with water. No simmer step is required. The crude hexahydro-1,3,5-trinitro-1,3,5-triazine solids are stirred in hot (>90° C.) 0.0-40% nitric acid and heated to reflux, and the new slurry stirred for 15-60 minutes at reflux, followed by cooling to 25° C. (20-60° C.) and filtering. The recovered solids are washed with water then recrystallized via the conventional process. The resulting solution recovered from the hot 0.0-40% nitric acid slurry of the filtered solids is recycled to subsequent crude filtered solids batch treatments. The aqueous spent acid is directed to the pre-distillation evaporators to separate the volatile components from the nonvolatile components. The pre-distilled aqueous spent acid is then purified via azeotropic distillation to yield glacial acetic acid to complete the recycle process. See FIG. 5.

Figure 6:
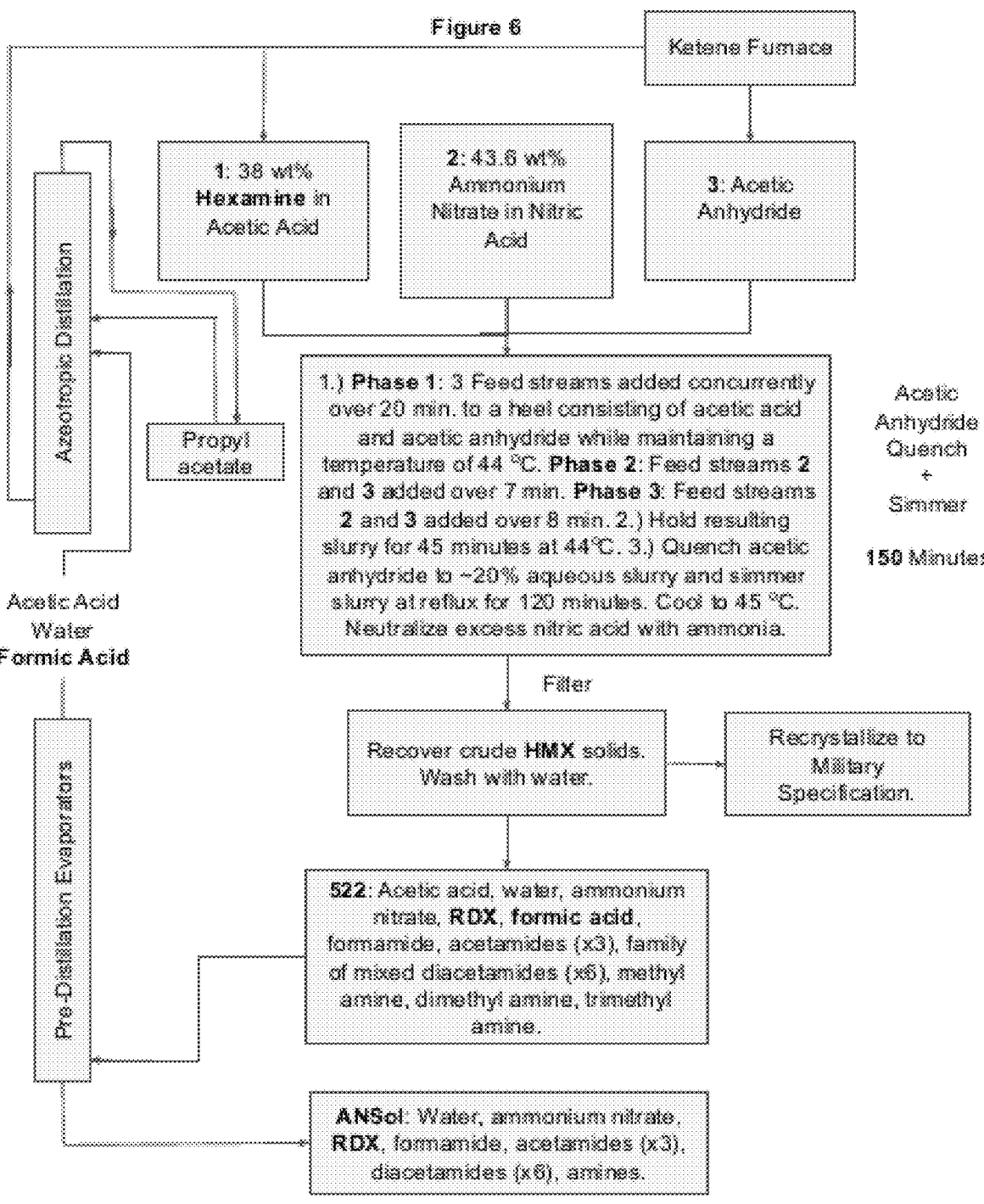
FIG. 6—Conventional process octahydro-1,3,5,7-tetranitro-1,3,5,7-tetrazocine.

B. Prior Conventional Process Octahydro-1,3,5,7-tetranitro-1,3,5,7-tetrazocine Referring to FIG. 6, the octahydro-1,3,5,7-tetranitro-1,3,5,7-tetrazocine nitrolysis shown, the multiphase additions are entered into the reactor as follows:

To a heel consisting of 437.6 g acetic acid and 10.9 g acetic anhydride are added three Feed Streams concurrently:

Feed Stream 1: 152.4 g of a 38 wt % 1,3,5,7-Tetraazatri-cyclo[3.3.1.1$^{3,7}$]decane solution in acetic acid.

Feed Stream 2: 94.9 g of a 43.6 wt % ammonium nitrate solution in nitric acid,

Feed Stream 3: 325.5 g of acetic anhydride.

The Feed Streams were added concurrently over 20 minutes to an agitated reactor containing a heel maintained at 44° C. Upon complete addition, the reaction slurry is aged at 44° C. for 6 minutes.

The reactor containing the first stage slurry is treated with two Feed Streams added concurrently over 7 minutes while maintaining a reactor temperature of 44° C.:

Feed Stream 2: 26.9 g of 43.6 wt % ammonium nitrate solution in nitric acid,

Feed Stream 3: 96.9 g acetic anhydride.

Immediately following the stage two addition, the reactor containing the second stage slurry is treated with two Feed Streams added concurrently over 8 minutes while maintaining a reactor temperature of 44° C.:

Feed Stream 2: 124.0 g 43.6 wt % ammonium nitrate in nitric acid,

Feed Stream 3: 352.3 g acetic anhydride.

Following the addition of the reagent Feed Streams the resulting slurry is aged at 44° C. for 45 minutes to ensure completion of the nitrolysis. Upon completion of the nitroly-sis step 718.8 g water is added at a rate to ensure the reaction slurry temperature does not exceed 50° C. The resulting aqueous acetic acid slurry is heated to 98-100° C. for 120 minutes to destroy undesired linear nitramines. The slurry is cooled to 40° C. and filtered. The solids are washed with water and dried. The filtrate is processed through pre-distillation evaporators to separate the volatile components from the nonvolatile components. The process stream con-sisting mainly of acetic acid, water and methanoic acid are directed to the distillation facility for final processing to glacial acetic acid (containing 0.20 to 0.30 wt % methanoic acid) to complete the process cycle. A portion of the glacial acetic acid is directed toward the ketene furnaces to regen-erate acetic anhydride and complete the process cycle. See FIG. 6.

Figure 7:
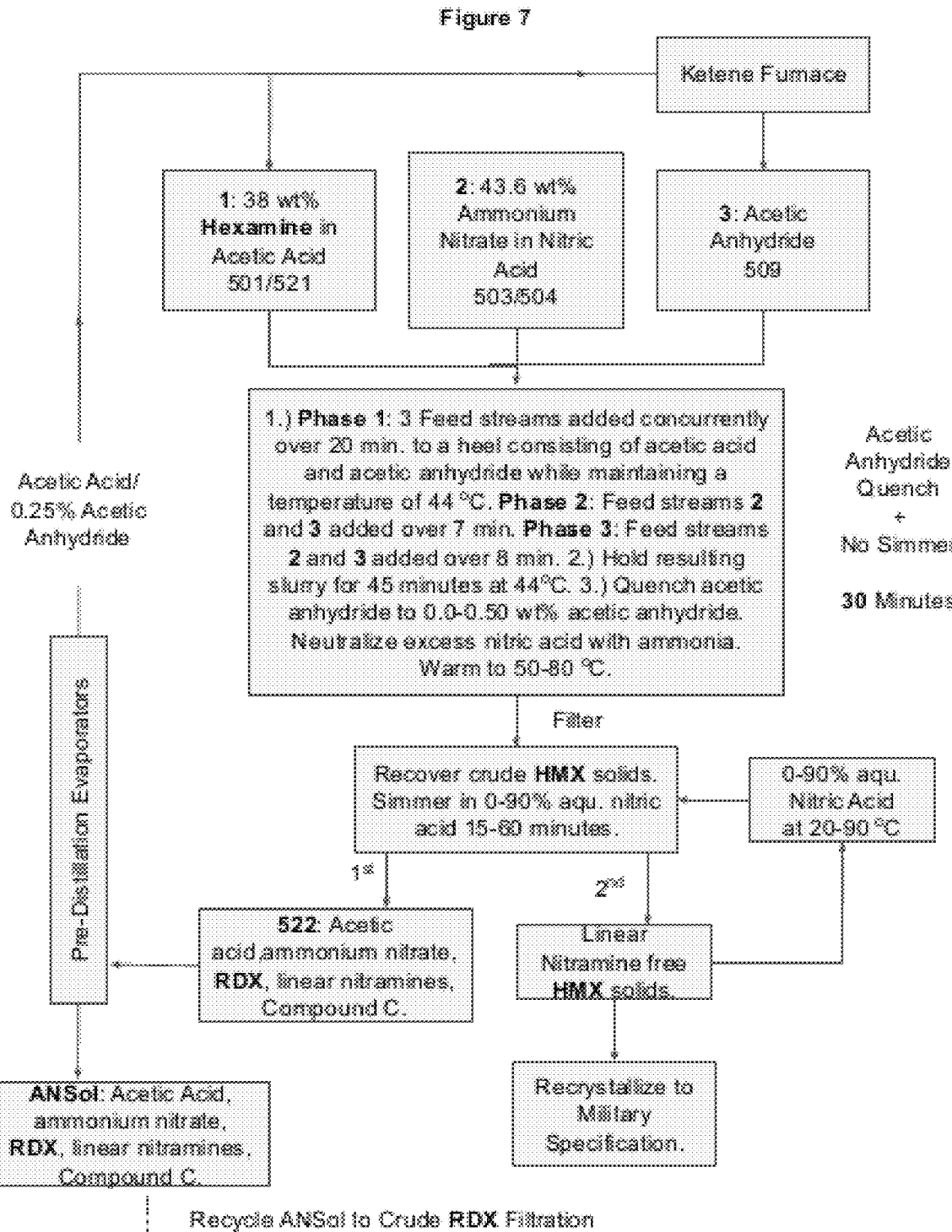
FIG. 7—Conventional octahydro-1,3,5,7-tetranitro-1,3,5, 7-tetrazocine process modified according to the present invention.

Example 7: Conventional Octahydro-1,3,5,7-tetranitro-1,3,5,7-tetrazocine Process Modified According to the Present Invention Equivalent to the B. Conventional Octahydro-1,3,5,7-tetranitro-1,3,5,7-tetrazocine Process, above, through nitrolysis 45 minute age at 44° C. Upon completion of the nitrolysis age step at 44° C. for 45 minutes, the reaction slurry is treated with sufficient ammonia (or ammonium acetate) to neutralize the excess nitric acid. The reaction slurry is maintained below 60° C. (40-60° C.) during the ammonia addition. To the neutralized slurry is added suffi-cient water to adjust the acetic anhydride content to 0.0-0.50 wt %. The temperature is maintained below 60° C. (40-60° C.) during the water addition. The final slurry is filtered at 50-80° C. to the extent the majority of the acetic acid is recovered. No simmer step is required. The filtered solids are stirred in hot (>90° C.) 0.0-40% nitric acid heated to reflux, and the new refluxing slurry stirred for 15-60 minutes, followed by cooling to 60° C. (60-80° C.) and filtering. The recovered solids are washed with water then recrystallized via the conventional process. The resulting solution recov-ered from the hot 0.0-40% nitric acid slurry of the filtered solids is recycled to subsequent crude filtered solids batch treatments. The anhydrous spent acid is directed to the pre-distillation evaporators to separate the volatile compo-nents from the nonvolatile components. An appropriate portion of the glacial acetic acid recovered from the pre-distillation evaporators (containing 0.0-0.50% acetic anhy-dride) is directed to the ketene furnaces to regenerate acetic anhydride to complete the recycle process. An appropriate portion of the glacial acetic acid recovered from the pre-distillation evaporators (containing 0.0-0.50% acetic anhy-dride) is directed toward the dissolution of 1,3,5,7-Tetraaza-tricyclo[3.3.1.1$^{3,7}$]decane. The remaining glacial acetic acid recovered from the pre-distillation evaporators (containing 0.0-0.50% acetic anhydride) is directed to the heel of the subsequent nitrolysis batch. The ANSol recovered from the pre-distillation evaporators can be recycled to the initial crude hexahydro-1,3,5-trinitro-1,3,5-triazine filtration. See FIG. 7.

Example 8: Direct Recycle of Spent Acid Octahydro-1,3,5,7-tetranitro-1,3,5,7-tetrazocine Modification Equivalent to the B. Conventional Octahydro-1,3,5,7-tetranitro-1,3,5,7-tetrazocine Process, above, through nitrolysis 45 minute age at 44° C. Upon completion of the nitrolysis age step at 44° C. for 45 minutes, the reaction slurry is treated with sufficient ammonia (or ammonium acetate) to neutralize the excess nitric acid. The reaction slurry is maintained below 60° C. (40-60° C.) during the ammonia addition. To the neutralized slurry is added suffi-cient water to adjust the acetic anhydride content to 0.0-0.50 wt %. The temperature is maintained below 60° C. (40-60° C.) during the water addition. The final slurry is warmed to 50-80° C. and filtered to the extent the majority of the acetic acid is recovered. No simmer step is required. The filtered solids are stirred in hot (>90° C.) 0.0-40% nitric acid and heated to reflux, and the new refluxing slurry stirred for 15-60 minutes, followed by cooling to 60° C. (60-80° C.) and filtering. The recovered solids are washed with water then recrystallized via the conventional process. The result-ing solution recovered from the hot 0.0-40% nitric acid slurry of the filtered solids is recycled to subsequent crude filtered solids batch treatments. The spent acid is cooled to 20° C. and filtered. The spent acid contains ammonium nitrate (~1.0-1.50 wt %). An appropriate portion of the anhydrous spent acid is directed toward dissolution of 1,3,5,7-tetraazatricyclo[3.3.1.1$^{3,7}$]decane. An appropriate portion of the anhydrous spent acid is directed toward the heel of the subsequent nitrolysis batch. The total ammonium nitrate from the 1,3,5,7-tetraazatricyclo[3.3.1.1$^{3,7}$]decane feed and heel formation carried into the subsequent nitration step is calculated. An equal molar amount (relative to the amount of ammonium nitrate present in the heel and 1,3,5,7-tetraazatricyclo[3.3.1.1$^{3,7}$]decane feed stream) of nitric acid is added to the heel. 0.50-1.0 molar equivalents (relative to the amount of ammonium nitrate present in the heel and 1,3,5,7-tetraazatricyclo[3.3.1.1$^{3,7}$]decane feed stream) of 1,3,5,7-tetraazatricyclo[3.3.1.1$^{3,7}$]decane are added to the heel. The remaining spent acid is directed to the pre-distillation evaporators to separate volatile components from nonvolatile components. The pre-distilled spent acid is directed to the ketene furnaces to regenerate acetic anhy-dride to complete the recycle process. The ANSol recovered from the pre-distillation evaporators can be recycled to the initial crude hexahydro-1,3,5-trinitro-1,3,5-triazine filtra-tion. See FIG. 8.

Example (assuming 1.0 wt % ammonium nitrate recycled acetic acid): 437.6 g acetic acid added to the heel.

437.6*0.01=4.38 g ammonium nitrate. 152.4 g of a 38 wt % 1,3,5,7-tetraazatricyclo[3.3.1.1³,⁷]decane solution in acetic acid added via the feed stream. 0.62*152.4*0.01=0.94 g ammonium nitrate. 5.32 g (0.067 mol) total ammonium nitrate added to the heel/reaction. 4.22 g (0.067 mol) nitric acid and 4.69-9.38 g (0.034-0.067 mol) 1,3,5,7-tetraazatricyclo[3.3.1.1³,⁷]decane added to the recycled heel. (not applicable to processes run with virgin acetic acid.)

Figure 8:
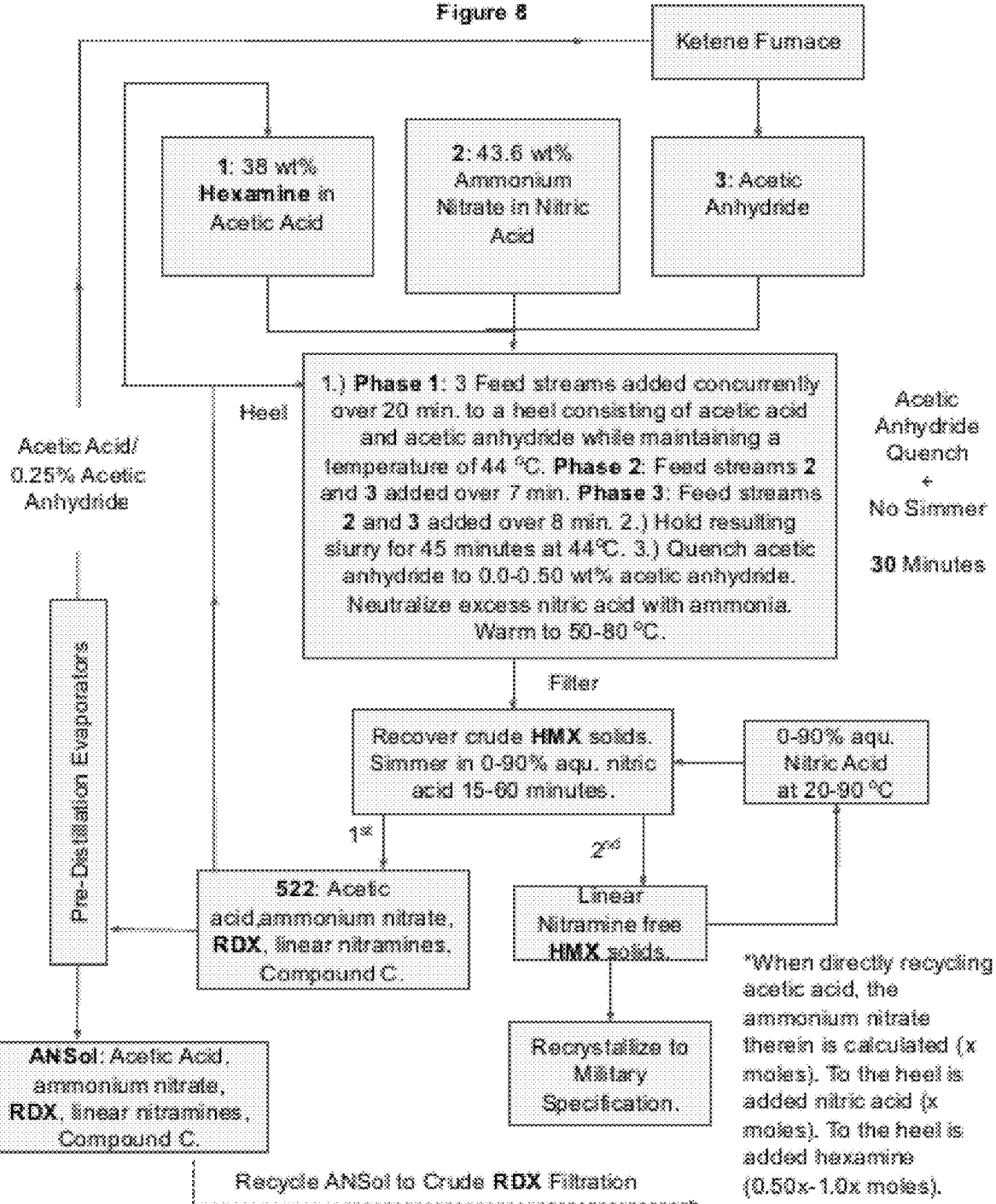
FIG. 8—Direct recycle of spent acid octahydro-1,3,5,7-tetranitro-1,3,5,7-tetrazocine modification.

Example 9: Improved Octahydro-1,3,5,7-tetranitro-1,3,5,7-tetrazocine with 1,3,5,7-Tetraazatricyclo [3.3.1.1³,⁷]decane/Nitric Acid/Ammonium Nitrate Heel with Anhydride Quench-No Recycle Referring to the flow diagram of the octahydro-1,3,5,7-tetranitro-1,3,5,7-tetrazocine nitrolysis shown in FIG. 2, the multiphase additions are entered into the reactor as follows: To a heel consisting of 437.6 g acetic acid and acetic anhydride (10.9-21.8 g), 1,3,5,7-tetraazatricyclo[3.3.1.1³,⁷] decane (0.0-28.96 g), and ammonium nitrate (0.0-49.65 g) at 20-25° C. is added nitric acid (0.0-39.1 g) at a rate to ensure the reaction mixture does not exceed 25° C. Following the nitric acid addition, the reaction mixture is warmed to 40-44° C. and following a hold period (0-10 min.) are added three Feed Streams concurrently:
Feed Stream 1: 152.4 g of a 38 wt % 1,3,5,7-tetraazatricyclo[3.3.1.1³,⁷]decane solution in acetic acid,
Feed Stream 2: 94.9 g of a 43.6 wt % ammonium nitrate solution in nitric acid,
Feed Stream 3: 325.5 g of acetic anhydride.
The Feed Streams were added concurrently over 20 minutes to an agitated reactor containing a heel maintained at 44° C. Upon complete addition, the reaction slurry is aged at 44° C. for 6 minutes.
The reactor containing the first stage slurry is treated with two Feed Streams added concurrently over 7 minutes while maintaining a reactor temperature of 44° C.:
Feeed stream 2: 26.9 g of 43.6 wt % ammonium nitrate solution in nitric acid,
Feed Stream 3: 96.9 g acetic anhydride.
Immediately following the stage two addition, the reactor containing the second stage slurry is treated with two Feed Streams added concurrently over 8 minutes while maintaining a reactor temperature of 44° C.:
Feed Stream 2: 124.0 g 43.6 wt % ammonium nitrate in nitric acid,
Feed Stream 3: 352.3 g acetic anhydride.
Following the addition of the reagent Feed Streams the resulting slurry is aged at 44° C. for 30 minutes, followed by 60° C. for 15 minutes. Upon reaction completion, the reaction slurry is treated with sufficient ammonia (or ammonium acetate) to neutralize the excess nitric acid. The reaction slurry is maintained below 60° C. (40-60° C.) during the ammonia addition. To the neutralized slurry is added sufficient water to adjust the acetic anhydride content to 0.0-0.50 wt %. The temperature is maintained below 60° C. (40-60° C.) during the water addition. Upon complete water addition the slurry is heated to 50-80° C. and filtered to the extent the majority of the acetic acid is recovered. The filtered solids are stirred in hot (>90° C.) 0.0-40% nitric acid and the new slurry heated to reflux for 15-60 minutes followed by cooling to 60° C. (60-80° C.) and filtering. The recovered aqueous nitric acid solution recycled directly to subsequent crude filtered solid octahydro-1,3,5,7-tetranitro-1,3,5,7-tetrazocine treatment steps. The recovered solids are recrystallized via the conventional process. The spent acid is directed to the pre-distillation evaporators to separate the volatile components from the nonvolatile components. An appropriate portion of the anhydrous glacial acetic acid recovered from the evaporators is directed to the ketene furnaces to regenerate acetic anhydride to complete the recycle process. An appropriate portion of the anhydrous glacial acetic acid recovered from the evaporators is directed toward the dissolution of 1,3,5,7-tetraazatricyclo[3.3.1.1³,⁷] decane. An appropriate portion of the anhydrous glacial acetic acid recovered from the evaporators is directed to the heel of subsequent nitrolysis batches. The ANSol recovered from the pre-distillation evaporators can be recycled to the initial crude Hexahydro-1,3,5-trinitro-1,3,5-triazine filtration. Analogous to what is shown in FIG. 8.
Standard Heel:
12.5% 1,3,5,7-Tetraazatricyclo[3.3.1.1³,⁷]decane Heel: 6.52 g nitric acid, 8.27 g ammonium nitrate, 7.24 g 1,3,5,7-Tetraazatricyclo[3.3.1.1³,⁷]decane, 10.9 g acetic anhydride.
25.0% 1,3,5,7-Tetraazatricyclo[3.3.1.1³,⁷]decane Heel: 13.04 g Nitric acid, 16.54 g ammonium nitrate, 14.48 g 1,3,5,7-Tetraazatricyclo[3.3.1.1³,⁷]decane, 16.35 g acetic anhydride.
50.0% 1,3,5,7-Tetraazatricyclo[3.3.1.1³,⁷]decane Heel: 26.08 g Nitric acid, 33.08 g ammonium nitrate, 28.96 g 1,3,5,7-Tetraazatricyclo[3.3.1.1³,⁷]decane, 21.80 g acetic anhydride.

Figure 10:
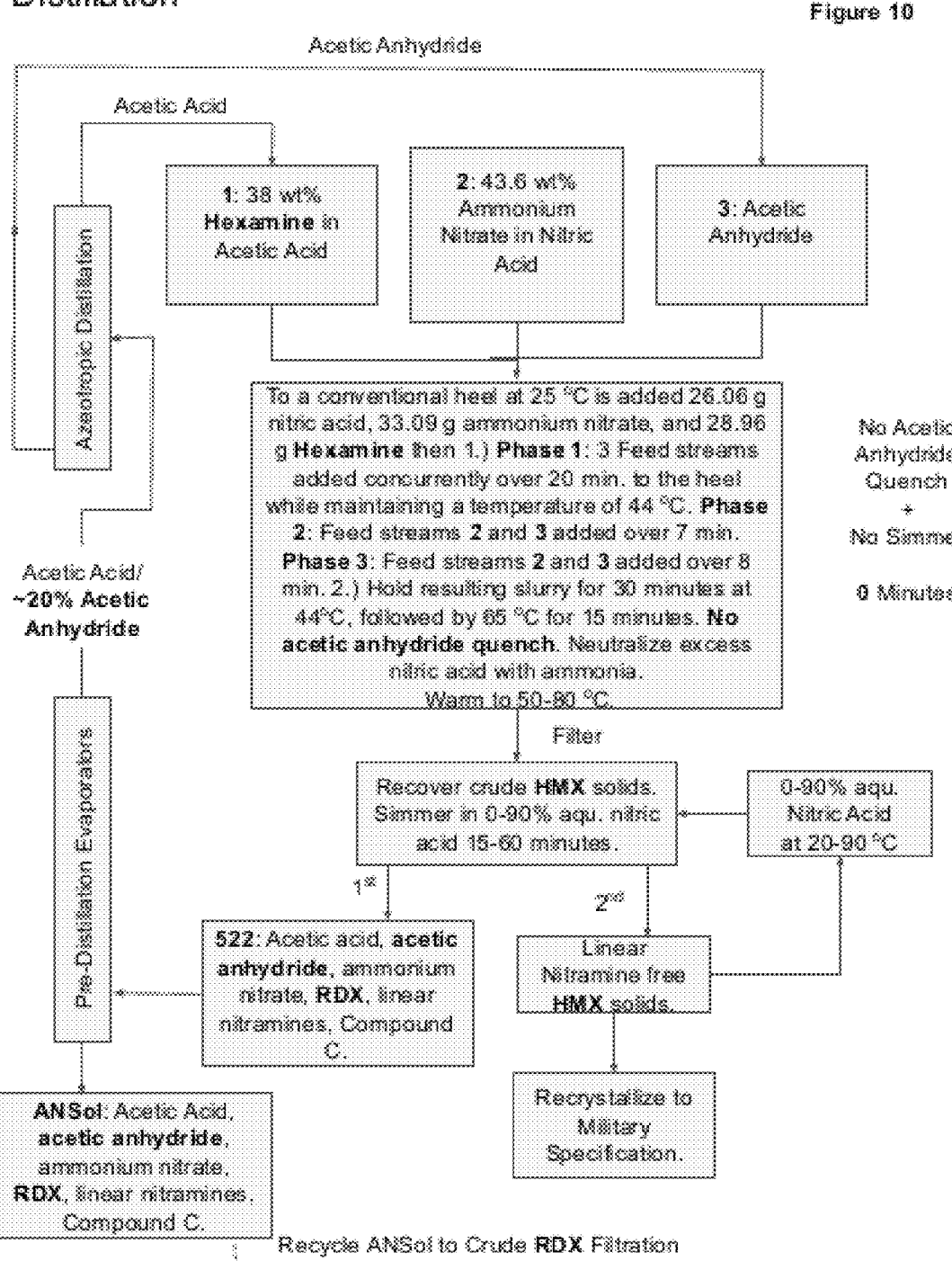
FIG. 10—New Heel octahydro-1,3,5,7-tetranitro-1,3,5,7-tetrazocine with 1,3,5,7-tetraazatricyclo[3.3.1.1$^{3,7}$]decane/nitric acid/ammonium nitrate heel without anhydride quench.

Example 10: Improved Octahydro-1,3,5,7-tetranitro-1,3,5,7-tetrazocine with 1,3,5,7-Tetraazatricyclo [3.3.1.13,7]decane/Nitric Acid/Ammonium Nitrate Heel with Anhydride Quench-Recycle of Acetic Acid to Heel and 1,3,5,7-Tetraazatricyclo[3.3.1.1³,⁷] decane Feed Analogous to what is shown in FIG. 10 and referring to the flow diagram of the octahydro-1,3,5,7-tetranitro-1,3,5,7-tetrazocine nitrolysis shown, the multiphase additions are entered into the reactor as follows:
To a heel consisting of 437.6 g acetic acid and acetic anhydride (10.9-21.8 g), 1,3,5,7-tetraazatricyclo[3.3.1.1³,⁷] decane (0.0-28.96 g), and ammonium nitrate (0.0-49.65 g) at 20-25° C. is added nitric acid (0.0-39.1 g) at a rate to ensure the reaction mixture does not exceed 25° C. Following the nitric acid addition, the reaction mixture is warmed to 40-44° C. and following a hold period (0-10 min.) are added three feed streams concurrently:
Feed Stream 1: 152.4 g of a 38 wt % 1,3,5,7-Tetraazatricyclo[3.3.1.1³,⁷]decane solution in acetic acid,
Feed stream 2: 94.9 g of a 43.6 wt % ammonium nitrate solution in nitric acid,
Feed Stream 3: 325.5 g of acetic anhydride.
The Feed Streams were added concurrently over 20 minutes to an agitated reactor containing a heel maintained at 44° C. Upon complete addition, the reaction slurry is aged at 44° C. for 6 minutes.
The reactor containing the first stage slurry is treated with two Feed Streams added concurrently over 7 minutes while maintaining a reactor temperature of 44° C.:
Feed Stream 2: 26.9 g of 43.6 wt % ammonium nitrate solution in nitric acid,
Feed Stream 3: 96.9 g acetic anhydride.
Immediately following the stage two addition, the reactor containing the second stage slurry is treated with two Feed Streams added concurrently over 8 minutes while maintaining a reactor temperature of 44° C.:
Feed Stream 2: 124.0 g 43.6 wt % ammonium nitrate in nitric acid, Feed Stream 3: 352.3 g acetic anhydride.

Following the addition of the reagent Feed Streams the resulting slurry is aged at 44° C. for 30 minutes, followed by 60° C. for 15 minutes. Upon reaction completion, the reaction slurry is treated with sufficient ammonia (or ammonium acetate) to neutralize the excess nitric acid. The reaction slurry is maintained below 60° C. (40-60° C.) during the ammonia addition. To the neutralized slurry is added sufficient water to adjust the acetic anhydride content to 0.0-0.50 wt %. The temperature is maintained below 60° C. (40-60° C.) during the water addition. Upon complete water addition the slurry is heated to 50-80° C. and filtered to the extent the majority of the acetic acid is recovered. The filtered solids are stirred in hot (>90° C.) 0.0-40% nitric acid and the new slurry heated to reflux for 15-60 minutes followed by cooling to 60° C. (60-80° C.) and filtering. The recovered aqueous nitric acid solution recycled directly to subsequent crude filtered solid Octahydro-1,3,5,7-tetranitro-1,3,5,7-tetrazocine treatment steps. The recovered solids are recrystallized via the conventional process. The spent acid is cooled to 20° C. and filtered. The spent acid contains ammonium nitrate (~1.0-1.50 wt %). An appropriate portion of the anhydrous spent acid is directed toward dissolution of 1,3,5,7-tetraazatricyclo[3.3.1.1$^{3,7}$]decane. An appropriate portion of the anhydrous spent acid is directed toward the heel of the subsequent nitrolysis batch [The total ammonium nitrate from the 1,3,5,7-tetraazatricyclo[3.3.1.1$^{3,7}$]decane feed and heel formation carried into the subsequent nitration step is calculated. The calculated amount of carryover ammonium nitrate (from 1,3,5,7-tetraazatricyclo[3.3.1.1$^{3,7}$] decane feed and heel formation acetic acid) is subtracted from the amount of ammonium nitrate added to the starting heel.] The remaining portion of the anhydrous glacial acetic acid sent to the evaporators is directed to the ketene furnaces to regenerate acetic anhydride to complete the recycle process. The ANSol recovered from the pre-distillation evaporators can be recycled to the initial crude hexahydro-1,3,5-trinitro-1,3,5-triazine filtration.

Standard Heel:

12.5% 1,3,5,7-Tetraazatricyclo[3.3.1.1$^{3,7}$]decane Heel: 6.52 g nitric acid, 8.27 g ammonium nitrate (account for ammonium nitrate added via the 1,3,5,7-Tetraazatricyclo [3.3.1.1$^{3,7}$]decane feed and heel acetic acid), 7.24 g 1,3,5,7-Tetraazatricyclo[3.3.1.1$^{3,7}$]decane, 10.9 g acetic anhydride.

25.0% 1,3,5,7-Tetraazatricyclo[3.3.1.1$^{3,7}$]decane Heel: 13.04 g Nitric acid, 16.54 g ammonium nitrate (account for ammonium nitrate added via the 1,3,5,7-Tetraazatricyclo [3.3.1.1$^{3,7}$]decane feed and heel acetic acid), 14.48 g 1,3,5,7-Tetraazatricyclo[3.3.1.1$^{3,7}$]decane, 16.35 g acetic anhydride.

50.0% 1,3,5,7-Tetraazatricyclo[3.3.1.1$^{3,7}$]decane Heel: 26.08 g Nitric acid, 33.08 g ammonium nitrate (account for ammonium nitrate added via the 1,3,5,7-Tetraazatricyclo [3.3.1.1$^{3,7}$]decane feed and heel acetic acid), 28.96 g 1,3,5,7-Tetraazatricyclo[3.3.1.1$^{3,7}$]decane, 21.80 g acetic anhydride.

Example: 25% 1,3,5,7-Tetraazatricyclo[3.3.1.1$^{3,7}$]decane heel (assuming 1.0 wt % ammonium nitrate recycled acetic acid): 437.6 g acetic acid added to the heel. 437.6*0.01=4.38 g ammonium nitrate. 152.4 g of a 38 wt % 1,3,5,7-tetraazatricyclo[3.3.1.1$^{3,7}$]decane solution in acetic acid added via the feed stream. 0.62*152.4*0.01=0.94 g ammonium nitrate. 5.32 g (0.067 mol) total ammonium nitrate added to the heel. A 25% 1,3,5,7-Tetraazatricyclo[3.3.1.1$^{3,7}$]decane heel requires 13.04 g nitric acid, 16.54 g ammonium nitrate, 14.48 g 1,3,5,7-tetraazatricyclo[3.3.1.1$^{3,7}$]decane. Accounting for ammonium nitrate brought forward in the recycled heel and recycled 1,3,5,7-tetraazatricyclo[3.3.1.1$^{3,7}$]decane solution feed stream, 13.04 g nitric acid, 11.22 g (16.54-5.32 g) ammonium nitrate, 14.48 g 1,3,5,7-tetraazatricyclo [3.3.1.1$^{3,7}$]decane added to the recycled heel at the start of the process.

Example 11: Improved Octahydro-1,3,5,7-tetranitro-1,3,5,7-tetrazocine with 1,3,5,7-Tetraazatricyclo [3.3.1.1$^{3,7}$]decane/Nitric Acid/Ammonium Nitrate Heel without Anhydride Quench Referring to FIG. 10 the Octahydro-1,3,5,7-tetranitro-1,3,5,7-tetrazocine nitrolysis shown in the drawing, the multiphase additions are entered into the reactor as follows:

To a heel consisting of 437.6 g acetic acid and acetic anhydride (10.9-21.8 g), 1,3,5,7-tetraazatricyclo[3.3.1.1$^{3,7}$] decane (0.0-28.96 g), and ammonium nitrate (0.0-49.65 g) at 20-25° C. is added nitric acid (0.0-39.1 g) at a rate to ensure the reaction mixture does not exceed 25° C. Following the nitric acid addition, the reaction mixture is warmed to 40-44° C. and following a hold period (0-10 min.) are added three feed streams concurrently:

Feed Stream 1: 152.4 g of a 38 wt % 1,3,5,7-Tetraazatricyclo[3.3.1.1$^{3,7}$]decane solution in acetic acid, Feed Stream 2: 94.9 g of a 43.6 wt % ammonium nitrate solution in nitric acid, Feed Stream 3: 325.5 g of acetic anhydride.

The Feed Streams were added concurrently over 20 minutes to an agitated reactor containing a heel maintained at 44° C. Upon complete addition, the reaction slurry is aged at 44° C. for 6 minutes.

The reactor containing the first stage slurry is treated with two Feed Streams added concurrently over 7 minutes while maintaining a reactor temperature of 44° C.:

Feed Stream 2: 26.9 g of 43.6 wt % ammonium nitrate solution in nitric acid,

Feed Stream 3: 96.9 g acetic anhydride.

Immediately following the stage two addition, the reactor containing the second stage slurry is treated with two Feed Streams added concurrently over 8 minutes while maintaining a reactor temperature of 44° C.:

Feed Stream 2: 124.0 g 43.6 wt % ammonium nitrate in nitric acid,

Feed Stream 3: 352.3 g acetic anhydride.

Following the addition of the reagent Feed Streams the resulting slurry is aged at 44° C. for 30 minutes, followed by 60° C. for 15 minutes. Upon reaction completion, the reaction slurry is treated with sufficient ammonia (or ammonium acetate) to neutralize the excess nitric acid. The reaction slurry is maintained below 60° C. (40-60° C.) during the ammonia addition. Upon complete nitric acid neutralization the slurry is heated to 50-80° C. and filtered to the extent the majority of the acetic acid/acetic anhydride is recovered. The filtered solids are stirred in hot (>90° C.) 0.0-40% nitric acid and the new slurry heated to reflux for 15-60 minutes followed by cooling to 60° C. (60-80° C.) and filtering. The recovered nitric acid solution recycled directly to subsequent octahydro-1,3,5,7-tetranitro-1,3,5,7-tetrazocine treatment steps. The spent acid is directed to the pre-distillation evaporators to separate the volatile components from the nonvolatile components. The pre-distilled acid is then azeotropically distilled to separate the acetic acid from the acetic anhydride. An appropriate portion of the anhydrous glacial acetic acid recovered from the azeotropic distillation is directed to the ketene furnaces to regenerate acetic anhydride to complete the recycle process. An appropriate portion of the anhydrous glacial acetic acid recovered from the azeotropic distillation is directed toward the dissolution of 1,3,5,7-tetraazatricyclo[3.3.1.1$^{3,7}$]decane. An appropriate portion of the anhydrous glacial acetic acid recovered from the azeotropic distillation is directed to the heel of subsequent nitrolysis batches. The ANSol recovered from the pre-distillation evaporators can be recycled into the initial crude Hexahydro-1,3,5-trinitro-1,3,5-triazine filtration.

Standard Heel:

12.5% 1,3,5,7-Tetraazatricyclo[3.3.1.1$^{3,7}$]decane Heel: 6.52 g nitric acid, 8.27 g ammonium nitrate, 7.24 g 1,3,5, 7-Tetraazatricyclo[3.3.1.1$^{3,7}$]decane, 10.9 g acetic anhydride.

25.0% 1,3,5,7-Tetraazatricyclo[3.3.1.1$^{3,7}$]decane Heel: 13.04 g Nitric acid, 16.54 g ammonium nitrate, 14.48 g 1,3,5,7-Tetraazatricyclo[3.3.1.1$^{3,7}$]decane, 16.35 g acetic anhydride.

50.0% 1,3,5,7-Tetraazatricyclo[3.3.1.1$^{3,7}$]decane Heel: 26.08 g Nitric acid, 33.08 g ammonium nitrate, 28.96 g 1,3,5,7-Tetraazatricyclo[3.3.1.1$^{3,7}$]decane, 21.80 g acetic anhydride.

Example 12: Improved Octahydro-1,3,5,7-tetranitro-1,3,5,7-tetrazocine with 1,3,5,7-Tetraazatricyclo [3.3.1.1$^{3,7}$]decane/Nitric Acid/Ammonium Nitrate Heel with Anhydride Quench-No Recycle-Addition of 1.0 Nitric acid in Phase 3 at 60° C.

Analogous to what is shown in FIG. 10 and referring to the flow diagram of the octahydro-1,3,5,7-tetranitro-1,3,5, 7-tetrazocine nitrolysis shown, the multiphase additions are entered into the reactor as follows:

To a heel consisting of 437.6 g acetic acid and acetic anhydride (10.9-21.8 g), 1,3,5,7-tetraazatricyclo[3.3.1.1$^{3,7}$] decane (0.0-28.96 g), and ammonium nitrate (0.0-49.65 g) at 20-25° C. is added nitric acid (0.0-39.1 g) at a rate to ensure the reaction mixture does not exceed 25° C. Following the nitric acid addition, the reaction mixture is warmed to 40-44° C. and following a hold period (0-10 min.) are added three feed streams concurrently:

Feed Stream 1: 152.4 g of a 38 wt % 1,3,5,7-Tetraazatricyclo[3.3.1.1$^{3,7}$]decane solution in acetic acid, Feedstram 2: 94.9 g of a 43.6 wt % ammonium nitrate solution in nitric acid, Feed Stream 3: 325.5 g of acetic anhydride.

The Feed Streams were added concurrently over 20 minutes to an agitated reactor containing a heel maintained at 44° C. Upon complete addition, the reaction slurry is aged at 44° C. for 6 minutes.

The reactor containing the first stage slurry is treated with two Feed Streams added concurrently over 7 minutes while maintaining a reactor temperature of 44° C.:

Feed Stream 2: 26.9 g of 43.6 wt % ammonium nitrate solution in nitric acid,

Feed Stream 3: 96.9 g acetic anhydride.

Immediately following the stage two addition, the reactor containing the second stage slurry is treated with two Feed Streams added concurrently over 8 minutes while maintaining a reactor temperature of 44° C.:

Feed Stream 2: 124.0 g 43.6 wt % ammonium nitrate in nitric acid,

Feed Stream 3:352.3 g acetic anhydride.

Following the addition of the reagent Feed Streams the resulting slurry is aged at 44° C. for 30 minutes, followed by direct addition of 0.25-1.0 equivalents (relative to total 1,3,5,7-tetraazatricyclo[3.3.1.1$^{3,7}$]decane, from heel and feed stream) of nitric acid and stirring at 60° C. for 15 minutes. Upon reaction completion, the reaction slurry is treated with sufficient ammonia (or ammonium acetate) to neutralize the excess nitric acid. The reaction slurry is maintained below 60° C. (40-60° C.) during the ammonia addition. To the neutralized slurry is added sufficient water to adjust the acetic anhydride content to 0.0-0.50 wt %. The temperature is maintained below 60° C. (40-60° C.) during the water addition. Upon complete water addition the slurry is heated to 50-80° C. and filtered to the extent the majority of the acetic acid is recovered. The filtered solids are stirred in hot (>90° C.) 0.0-40% nitric acid and the new slurry heated to reflux for 15-60 minutes followed by cooling to 60° C. (60-80° C.) and filtering. The recovered aqueous nitric acid solution recycled directly to subsequent crude filtered solid Octahydro-1,3,5,7-tetranitro-1,3,5,7-tetrazocine treatment steps. The spent acid is directed to the pre-distillation evaporators to separate the volatile components from the nonvolatile components. An appropriate portion of the anhydrous glacial acetic acid recovered from the evaporators is directed to the ketene furnaces to regenerate acetic anhydride to complete the recycle process. An appropriate portion of the anhydrous glacial acetic acid recovered from the evaporators is directed toward the dissolution of 1,3,5,7-Tetraazatricyclo[3.3.1.1$^{3,7}$]decane. An appropriate portion of the anhydrous glacial acetic acid recovered from the evaporators is directed to the heel of subsequent nitrolysis batches. The ANSol recovered from the pre-distillation evaporators can be recycled to the initial crude Hexahydro-1,3,5-trinitro-1,3,5-triazine filtration.

Standard Heel:

12.5% 1,3,5,7-Tetraazatricyclo[3.3.1.1$^{3,7}$]decane Heel: 6.52 g nitric acid, 8.27 g ammonium nitrate, 7.24 g 1,3,5, 7-Tetraazatricyclo[3.3.1.1$^{3,7}$]decane, 10.9 g acetic anhydride.

25.0% 1,3,5,7-Tetraazatricyclo[3.3.1.1$^{3,7}$]decane Heel: 13.04 g Nitric acid, 16.54 g ammonium nitrate, 14.48 g 1,3,5,7-Tetraazatricyclo[3.3.1.1$^{3,7}$]decane, 16.35 g acetic anhydride.

50.0% 1,3,5,7-Tetraazatricyclo[3.3.1.1$^{3,7}$]decane Heel: 26.08 g Nitric acid, 33.08 g ammonium nitrate, 28.96 g 1,3,5,7-Tetraazatricyclo[3.3.1.1$^{3,7}$]decane, 21.80 g acetic anhydride.

Example 13: Improved Octahydro-1,3,5,7-tetranitro-1,3,5,7-tetrazocine with 1,3,5,7-Tetraazatricyclo [3.3.1.1$^{3,7}$]decane/Nitric Acid/Ammonium Nitrate Heel without Anhydride Quench-Addition of 1.0 Nitric acid in Phase 3 at 60° C.

Analogous to what is shown in FIG. 10 and referring to the flow diagram of the Octahydro-1,3,5,7-tetranitro-1,3,5, 7-tetrazocine nitrolysis shown, the multiphase additions are entered into the reactor as follows:

To a heel consisting of 437.6 g acetic acid and acetic anhydride (10.9-21.8 g), 1,3,5,7-Tetraazatricyclo[3.3.1.1$^{3,7}$] decane (0.0-28.96 g), and ammonium nitrate (0.0-49.65 g) at 20-25° C. is added nitric acid (0.0-39.1 g) at a rate to ensure the reaction mixture does not exceed 25° C. Following the nitric acid addition, the reaction mixture is warmed to 40-44° C. and following a hold period (0-10 min.) are added three feed streams concurrently:

Feed Stream 1: 152.4 g of a 38 wt % 1,3,5,7-Tetraazatricyclo[3.3.1.1$^{3,7}$]decane solution in acetic acid, Feed Stream 2: 94.9 g of a 43.6 wt % ammonium nitrate solution in nitric acid, Feed Stream 3: 325.5 g of acetic anhydride.

The Feed Streams were added concurrently over 20 minutes to an agitated reactor containing a heel maintained at 44° C. Upon complete addition, the reaction slurry is aged at 44° C. for 6 minutes.

The reactor containing the first stage slurry is treated with two Feed Streams added concurrently over 7 minutes while maintaining a reactor temperature of 44° C.:

Feed Stream 2: 26.9 g of 43.6 wt % ammonium nitrate solution in nitric acid,

Feed Stream 3: 96.9 g acetic anhydride.

Immediately following the stage two addition, the reactor containing the second stage slurry is treated with two Feed Streams added concurrently over 8 minutes while maintaining a reactor temperature of 44° C.:

Feed Stream 2: 124.0 g 43.6 wt % ammonium nitrate in nitric acid,

Feed Stream 3: 352.3 g acetic anhydride.

Following the addition of the reagent Feed Streams the resulting slurry is aged at 44° C. for 30 minutes, followed by direct addition of 0.25-1.0 equivalents (relative to total 1,3,5,7-tetraazatricyclo[3.3.1.1$^{3,7}$]decane, heel and feed stream) of nitric acid and stirring at 60° C. for 15 minutes. Upon reaction completion, the reaction slurry is treated with sufficient ammonia (or ammonium acetate) to neutralize the excess nitric acid. The reaction slurry is maintained below 60° C. (40-60° C.) during the ammonia addition. Upon complete nitric acid neutralization the slurry is heated to 50-80° C. and filtered to the extent the majority of the acetic acid is recovered. The filtered solids are stirred in hot (>90° C.) 0.0-40% nitric acid and the new slurry heated to reflux for 15-60 minutes followed by cooling to 60° C. (60-80° C.) and filtering. The recovered nitric acid solution recycled directly to subsequent Octahydro-1,3,5,7-tetranitro-1,3,5,7-tetrazocine treatment steps. The spent acid is directed to the pre-distillation evaporators to separate the volatile components from the nonvolatile components. The pre-distilled acid is then azeotropically distilled to separate the acetic acid from the acetic anhydride. An appropriate portion of the anhydrous glacial acetic acid recovered from the azeotropic distillation is directed to the ketene furnaces to regenerate acetic anhydride to complete the recycle process. An appropriate portion of the anhydrous glacial acetic acid recovered from the azeotropic distillation is directed toward the dissolution of 1,3,5,7-tetraazatricyclo[3.3.1.1$^{3,7}$]decane. An appropriate portion of the anhydrous glacial acetic acid recovered from the azeotropic distillation is directed to the heel of subsequent nitrolysis batches. The ANSol recovered from the pre-distillation evaporators can be recycled to the initial crude hexahydro-1,3,5-trinitro-1,3,5-triazine filtration.

Standard Heel:

12.5% 1,3,5,7-Tetraazatricyclo[3.3.1.1$^{3,7}$]decane Heel: 6.52 g nitric acid, 8.27 g ammonium nitrate, 7.24 g 1,3,5,7-Tetraazatricyclo[3.3.1.1$^{3,7}$]decane, 10.9 g acetic anhydride.

25.0% 1,3,5,7-Tetraazatricyclo[3.3.1.1$^{3,7}$]decane Heel: 13.04 g Nitric acid, 16.54 g ammonium nitrate, 14.48 g 1,3,5,7-Tetraazatricyclo[3.3.1.1$^{3,7}$]decane, 16.35 g acetic anhydride.

50.0% 1,3,5,7-Tetraazatricyclo[3.3.1.1$^{3,7}$]decane Heel: 26.08 g Nitric acid, 33.08 g ammonium nitrate, 28.96 g 1,3,5,7-Tetraazatricyclo[3.3.1.1$^{3,7}$]decane, 21.80 g acetic anhydride.

Example 14: Improved Octahydro-1,3,5,7-tetranitro-1,3,5,7-tetrazocine with 1,3,5,7-Tetraazatricyclo[3.3.1.1$^{3,7}$]decane/Nitric Acid/Ammonium Nitrate Heel with Anhydride Quench-Addition of 1.0 Nitric acid in Phase 3 at 60° C.—Recycle Spent Acid Analogous to what is shown in FIG. 10 and referring to the flow diagram of the Octahydro-1,3,5,7-tetranitro-1,3,5,7-tetrazocine nitrolysis shown, the multiphase additions are entered into the reactor as follows:

To a heel consisting of 437.6 g acetic acid and acetic anhydride (10.9-21.8 g), 1,3,5,7-tetraazatricyclo[3.3.1.1$^{3,7}$]decane (0.0-28.96 g), and ammonium nitrate (0.0-49.65 g) at 20-25° C. is added nitric acid (0.0-39.1 g) at a rate to ensure the reaction mixture does not exceed 25° C. Following the nitric acid addition, the reaction mixture is warmed to 40-44° C. and following a hold period (0-10 min.) are added three feed streams concurrently:

Feed Stream 1: 152.4 g of a 38 wt % 1,3,5,7-Tetraazatricyclo[3.3.1.1$^{3,7}$]decane solution in acetic acid, Feed Stream 2: 94.9 g of a 43.6 wt % ammonium nitrate solution in nitric acid, Feed Stream 3: 325.5 g of acetic anhydride.

The Feed Streams were added concurrently over 20 minutes to an agitated reactor containing a heel maintained at 44° C. Upon complete addition, the reaction slurry is aged at 44° C. for 6 minutes.

The reactor containing the first stage slurry is treated with two Feed Streams added concurrently over 7 minutes while maintaining a reactor temperature of 44° C.:

Feed Stream 2: 26.9 g of 43.6 wt % ammonium nitrate solution in nitric acid,

Feed Stream 3: 96.9 g acetic anhydride.

Immediately following the stage two addition, the reactor containing the second stage slurry is treated with two Feed Streams added concurrently over 8 minutes while maintaining a reactor temperature of 44° C.:

Feed Stream 2: 124.0 g 43.6 wt % ammonium nitrate in nitric acid,

Feed Stream 3: 352.3 g acetic anhydride.

Following the addition of the reagent Feed Streams the resulting slurry is aged at 44° C. for 30 minutes, followed by direct addition of 0.25-1.0 equivalents (relative to total 1,3,5,7-tetraazatricyclo[3.3.1.1$^{3,7}$]decane, from heel and feed stream) of nitric acid and stirring at 60° C. for 15 minutes. Upon reaction completion, the reaction slurry is treated with sufficient ammonia (or ammonium acetate) to neutralize the excess nitric acid. The reaction slurry is maintained below 60° C. (40-60° C.) during the ammonia addition. To the neutralized slurry is added sufficient water to adjust the acetic anhydride content to 0.0-0.50 wt %. The temperature is maintained below 60° C. (40-60° C.) during the water addition. Upon complete water addition the slurry is heated to 50-80° C. and filtered to the extent the majority of the acetic acid is recovered. The filtered solids are stirred in hot (>90° C.) 0.0-40% nitric acid and the new slurry heated to reflux for 15-60 minutes followed by cooling to 60° C. (60-80° C.) and filtering. The recovered aqueous nitric acid solution recycled directly to subsequent crude filtered solid Octahydro-1,3,5,7-tetranitro-1,3,5,7-tetrazocine treatment steps. The spent acid is cooled to 20° C. and filtered. The spent acid contains ammonium nitrate (~1.0-1.50 wt %). An appropriate portion of the anhydrous spent acid is directed toward dissolution of 1,3,5,7-tetraazatricyclo[3.3.1.1$^{3,7}$]decane. An appropriate portion of the anhydrous spent acid is directed toward the heel of the subsequent nitrolysis batch [The total ammonium nitrate from the 1,3,5,7-tetraazatricyclo[3.3.1.1$^{3,7}$]decane feed and heel formation carried into the subsequent nitration step is calculated. The calculated amount of carryover ammonium nitrate (from 1,3,5,7-tetraazatricyclo[3.3.1.1$^{3,7}$]decane feed and heel formation acetic acid) is subtracted from the amount of ammonium nitrate added to the starting heel.] The remaining portion of the anhydrous glacial acetic acid sent to the evaporators is directed to the ketene furnaces to regenerate acetic anhydride to complete the recycle process. The ANSol recovered from the pre-distillation evaporators can be recycled to the initial crude Hexahydro-1,3,5-trinitro-1,3,5-triazine filtration.

Example: 25% 1,3,5,7-tetraazatricyclo[3.3.1.1$^{3,7}$]decane heel (assuming 1.0 wt % ammonium nitrate recycled acetic acid): 437.6 g acetic acid added to the heel. 437.6*0.01=4.38 g ammonium nitrate. 152.4 g of a 38 wt % 1,3,5,7-tetraazatricyclo[3.3.1.1$^{3,7}$]decane solution in acetic acid added via the feed stream. 0.62*152.4*0.01=0.94 g ammonium nitrate. 5.32 g (0.067 mol) total ammonium nitrate added to the heel. A 25% 1,3,5,7-Tetraazatricyclo[3.3.1.1$^{3,7}$]decane heel requires 13.04 g nitric acid, 16.54 g ammonium nitrate, 14.48 g 1,3,5,7-tetraazatricyclo[3.3.1.1$^{3,7}$]decane. Accounting for ammonium nitrate brought forward in the recycled heel and recycled 1,3,5,7-tetraazatricyclo[3.3.1.1$^{3,7}$]decane solution feed stream, 13.04 g nitric acid, 11.22 g (16.54-5.32 g) ammonium nitrate, 14.48 g 1,3,5,7-tetraazatricyclo [3.3.1.1$^{3,7}$]decane added to the heel at the start of the process.

Standard Heel:

12.5% 1,3,5,7-Tetraazatricyclo[3.3.1.1$^{3,7}$]decane Heel: 6.52 g nitric acid, 8.27 g ammonium nitrate, 7.24 g 1,3,5,7-Tetraazatricyclo[3.3.1.1$^{3,7}$]decane, 10.9 g acetic anhydride.

25.0% 1,3,5,7-Tetraazatricyclo[3.3.1.1$^{3,7}$]decane Heel: 13.04 g Nitric acid, 16.54 g ammonium nitrate, 14.48 g 1,3,5,7-Tetraazatricyclo[3.3.1.1$^{3,7}$]decane, 16.35 g acetic anhydride.

50.0% 1,3,5,7-Tetraazatricyclo[3.3.1.1$^{3,7}$]decane Heel: 26.08 g Nitric acid, 33.08 g ammonium nitrate, 28.96 g 1,3,5,7-Tetraazatricyclo[3.3.1.1$^{3,7}$]decane, 21.80 g acetic anhydride.

Figure 11:
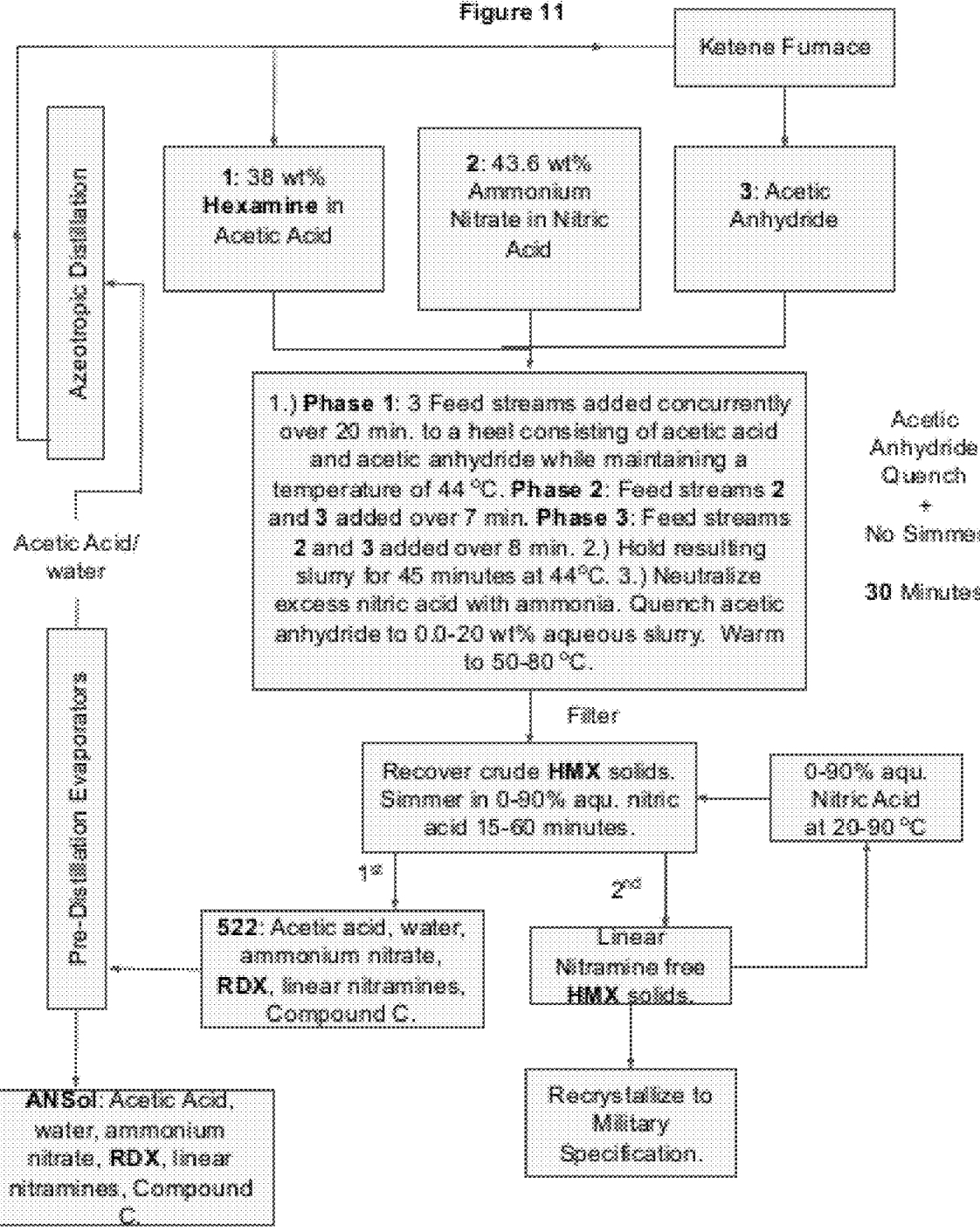
FIG. 11—Octahydro-1,3,5,7-tetranitro-1,3,5,7-tetrazo-cine modified process with complete acetic anhydride quench to aqueous spent acid.

Example 15:
Octahydro-1,3,5,7-tetranitro-1,3,5,7-tetrazocine Modified Process with Complete Acetic Anhydride Quench Equivalent to the Octahydro-1,3,5,7-tetranitro-1,3,5,7-tetrazocine B. Conventional Process, above, through nitrolysis 45 minute age at 44° C. Upon completion of the nitrolysis step at 44° C. for 45 minutes, the reaction slurry is cooled to 45° C. (25-55° C.) and treated with sufficient ammonia (ammonium acetate) to neutralize the excess nitric acid. The reaction slurry is maintained below 50° C. during the ammonia addition. To the neutralized slurry is added sufficient water to fully quench the acetic anhydride and adjust the water content to 0.0-25 wt %. The temperature is maintained below 60° C. (40-60° C.) during the water addition. The final slurry is warmed to 50-80° C. and filtered. The filter cake is washed with water. No simmer step is required. The crude octahydro-1,3,5,7-tetranitro-1,3, 5,7-tetrazocine solids are stirred in hot (>90° C.) 0.0-40% nitric acid and heated to reflux, and the new slurry stirred for 15-60 minutes, followed by cooling to 60° C. (60-80° C.) and filtering. The recovered solids are washed with water then recrystallized via the conventional process. The resulting solution recovered from the hot 0.0-40% nitric acid slurry of the filtered solids is recycled to subsequent crude filtered solids batch treatments. The aqueous spent acid is directed to the pre-distillation evaporators to separate the volatile components from the nonvolatile components. The pre-distilled aqueous spent acid is then purified via azeotropic distillation to yield glacial acetic acid to complete the recycle process. See FIG. 11.

Example 16:
Octahydro-1,3,5,7-tetranitro-1,3,5,7-tetrazocine Modification—No Acetic Anhydride Quench Equivalent to the octahydro-1,3,5,7-tetranitro-1,3,5,7-tetrazocine B. Conventional Process, above, through nitrolysis 45 minute age at 44° C. Upon completion of the nitrolysis age step at 44° C. for 45 minutes, the reaction slurry is cooled to 45° C. (25-55° C.) and treated with sufficient ammonia (ammonium acetate) to neutralize the excess nitric acid. The reaction slurry is maintained below 50° C. during the ammonia addition. Upon completion of the nitric acid neutralization the reaction slurry is heated to 50-80° C. ° C. and filtered to the extent the majority of the acetic acid/acetic anhydride is recovered. No simmer step is required. The filtered solids are stirred in hot (>90° C.) 0.0-40% nitric acid and heated to reflux, and the new refluxing slurry stirred for 15-60 minutes, followed by cooling to 60° C. (60-80° C.) and filtering. The recovered solids are washed with water then recrystallized via the conventional process. The resulting solution recovered from the hot 0.0-40% nitric acid slurry of the filtered solids is recycled to subsequent crude filtered solids batch treatments. The spent acid is cooled to 20° C. and filtered. The anhydrous spent acid consisting of acetic acid and acetic anhydride is directed to the pre-distillation evaporators to remove solids, followed by azeotropic distillation to separate acetic acid from acetic anhydride. An appropriate portion of the anhydrous glacial acetic acid recovered from the azeotropic distillation is directed to the ketene furnaces to regenerate acetic anhydride to complete the recycle process. An appropriate portion of the anhydrous glacial acetic acid recovered from the azeotropic distillation is directed toward the dissolution of 1,3,5,7-tetraazatricyclo[3.3.1.1$^{3,7}$]decane. An appropriate portion of the anhydrous glacial acetic acid recovered from the azeotropic distillation is directed to the heel of subsequent nitrolysis batches. The ANSol recovered from the pre-distillation evaporators can be recycled to the initial crude hexahydro-1,3,5-trinitro-1,3,5-triazine filtration. See FIG. 9.

Example 17: Octahydro-1,3,5,7-tetranitro-1,3,5,7-tetrazocine Modification—Complete 1,3,5,7-Tetraazatricyclo[3.3.1.1$^{3,7}$]decane Charge added to the Heel a). Stage 1: To a heel containing 437.6 g acetic acid and 0.0-10.9 g acetic anhydride at 25° C. is added 152.4 g of a 38 wt % Hexamine solution in acetic acid while maintaining the temperature near 25° C. To the reaction mixture at 20° C. is added 0.83 mols (66.4 g) of ammonium nitrate and 0.83 mols (52.3 g) of nitric acid at a rate to ensure the reaction mixture does not exceed 25° C. Upon complete addition of nitric acid, warm the reaction mixture to 44° C. and hold (0-10 min). Add 325.5 g acetic anhydride over 20 minutes to an agitated reactor containing a heel maintained at 44° C. Upon complete addition, the reaction slurry is aged at 44° C. for 6 minutes.

b). Stage 2: The reactor containing the first stage slurry is treated with two feed streams added concurrently over 7 minutes while maintaining a reactor temperature of 44° C.:

Feed Stream 2: 26.9 g of 43.6 wt % ammonium nitrate solution in nitric acid,

Feed Stream 3: 96.9 g acetic anhydride.

c). Immediately following the stage two addition, the reactor containing the second stage slurry is treated with two feed streams added concurrently over 8 minutes while maintaining a reactor temperature of 44° C.:

Feed Stream 2: 124.0 g 43.6 wt % ammonium nitrate in nitric acid,

Feed Stream 3: 352.3 g acetic anhydride.

d). Following the addition of the reagent feed streams the resulting slurry is aged at 44° C. for 45 minutes to ensure completion of the nitrolysis step. Upon completion of the nitrolysis age step at 44° C. for 45 minutes, the reaction slurry is treated with sufficient ammonia (or ammonium acetate) to neutralize the excess nitric acid. The reaction slurry is maintained below 60° C. (40-60° C.) during the ammonia addition. To the neutralized slurry is added sufficient water to adjust the acetic anhydride content to 0.0-0.50 wt %. The temperature is maintained below 60° C. (40-60° C.) during the water addition. The final slurry is filtered at 50-80° C. to the extent the majority of the acetic acid is recovered. No simmer step is required. The filtered solids are stirred in hot (>90° C.) 0.0-40% nitric acid and heated to reflux, and the new refluxing slurry stirred for 15-60 minutes, followed by cooling to 60° C. (60-80° C.) and filtering. The recovered solids are washed with water then recrystallized via the conventional process. The resulting solution recovered from the hot 0.0-40% nitric acid slurry of the filtered solids is recycled to subsequent crude filtered solids batch treatments. The anhydrous spent acid is directed to the pre-distillation evaporators to separate the volatile components from the nonvolatile components. An appropriate portion of the glacial acetic acid recovered from the evaporators (containing 0.0-0.50% acetic anhydride) is directed to the ketene furnaces to regenerate acetic anhydride to complete the recycle process. An appropriate portion of the glacial acetic acid recovered from the evaporators (containing 0.0-0.50% acetic anhydride) is directed toward the dissolution of 1,3,5,7-tetraazatricyclo[3.3.1.1$^{3,7}$]decane. The remaining glacial acetic acid recovered from the evaporators (containing 0.0-0.50% acetic anhydride) is directed to the heel of the subsequent nitrolysis batch. The ANSol recovered from the pre-distillation evaporators can be recycled to the initial crude hexahydro-1,3,5-trinitro-1,3,5-triazine filtration. Analogous to what is shown in FIG. 10.

Example 18.
Octahydro-1,3,5,7-tetranitro-1,3,5,7-tetrazocine Modification—Replace Ammonium Nitrate with Sodium Nitrate FIGS. 12A, 12B, 12C, and 12D provide a potential mechanistic rationale for this embodiment. However, it to be understood that this mechanistic rationale is in no way intended to limit this or other embodiments of the present invention.

To a heel containing of 437.6 g acetic acid and 10.9 g acetic anhydride are added three feed streams concurrently:

Feed Stream 1: 152.4 g of a 38 wt % 1,3,5,7-Tetraazatricyclo[3.3.1.1$^{3,7}$]decane solution in acetic acid, Feed Stream 2: 97.5 g of a 45.1 wt % sodium nitrate solution in nitric acid, Feed Stream 3: 325.5 g of acetic anhydride.

The Feed Streams were added concurrently over 20 minutes to an agitated reactor containing a heel maintained at 44° C. Upon complete addition, the reaction slurry is aged at 44° C. for 6 minutes.

The reactor containing the first stage slurry is treated with two feed streams added concurrently over 7 minutes while maintaining a reactor temperature of 44° C.:

Feed Stream 2: 26.9 g of 43.6 wt % ammonium nitrate solution in nitric acid,

Feed Stream 3: 96.9 g acetic anhydride.

Immediately following the stage two addition, the reactor containing the second stage slurry is treated with two Feed Streams added concurrently over 8 minutes while maintaining a reactor temperature of 44° C.:

Feed Stream 2: 124.0 g 43.6 wt % ammonium nitrate in nitric acid,

Feed Stream 3: 352.3 g acetic anhydride.

Following the addition of the reagent Feed Streams the resulting slurry is aged at 44° C. for 45 minutes to ensure completion of the nitrolysis. Upon completion of the nitrolysis age step at 44° C. for 45 minutes, the reaction slurry is treated with sufficient ammonia (or ammonium acetate) to neutralize the excess nitric acid. The reaction slurry is maintained below 60° C. (40-60° C.) during the ammonia addition. To the neutralized slurry is added sufficient water to adjust the acetic anhydride content to 0.0-0.50 wt %. The temperature is maintained below 60° C. (40-60° C.) during the water addition. The final slurry is filtered at 50-80° C. to the extent the majority of the acetic acid is recovered. No simmer step is required. The filtered solids are stirred in hot (>90° C.) 0.0-40% nitric acid and heated to reflux, and the new refluxing slurry stirred for 15-60 minutes, followed by cooling to 60° C. (60-80° C.) and filtering. The recovered solids are washed with water then recrystallized via the conventional process. The resulting solution recovered from the hot 0.0-40% nitric acid slurry of the filtered solids is recycled to subsequent crude filtered solids batch treatments. The anhydrous spent acid is directed to the pre-distillation evaporators to separate the volatile components from the nonvolatile components. An appropriate portion of the glacial acetic acid recovered from the evaporators (containing 0.0-0.50% acetic anhydride) is directed to the ketene furnaces to regenerate acetic anhydride to complete the recycle process. An appropriate portion of the glacial acetic acid recovered from the evaporators (containing 0.0-0.50% acetic anhydride) is directed toward the dissolution of 1,3,5,7-Tetraazatricyclo[3.3.1.1$^{3,7}$]decane. The remaining glacial acetic acid recovered from the evaporators (containing 0.0-0.50% acetic anhydride) is directed to the heel of the subsequent nitrolysis batch. The ANSol recovered from the pre-distillation evaporators can be recycled to the initial crude hexahydro-1,3,5-trinitro-1,3,5-triazine filtration. Analogous to what is shown in FIG. 8.

Example 19: Direct Recycle of Spent Acid to Octahydro-1,3,5,7-tetranitro-1,3,5,7-tetrazocine Modification-No Anhydride Quench-Recycle to Heel Only Following the addition of the reagent Feed Streams the resulting slurry is aged at 44° C. for 30 minutes, followed by 60° C. for 15 minutes. Upon reaction completion, the reaction slurry is treated with sufficient ammonia (or ammonium acetate) to neutralize the excess nitric acid.

Figure 9:
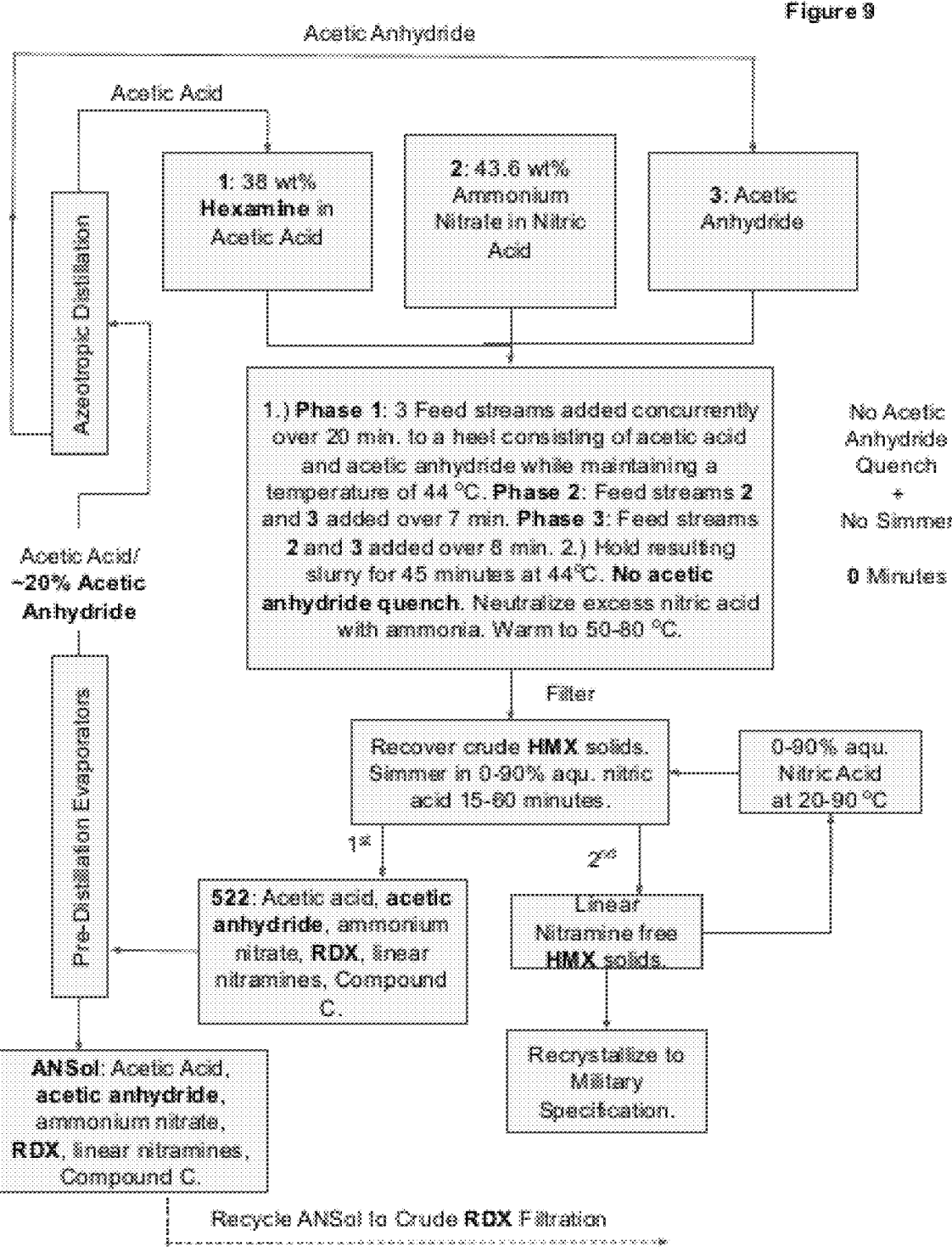
FIG. 9—Octahydro-1,3,5,7-tetranitro-1,3,5,7-tetrazocine modification—no acetic anhydride quench.

The reaction slurry is maintained below 60° C. (40-60° C.) during the ammonia addition. Upon complete nitric acid neutralization, the slurry is heated to 50-80° C. and filtered to the extent the majority of the acetic acid/acetic anhydride is recovered. The filtered solids are stirred in hot (>90° C.) 0.0-40% nitric acid and the new slurry heated to reflux for 15-60 minutes followed by cooling to 60° C. (60-80° C.) and filtering. The recovered nitric acid solution recycled directly to subsequent octahydro-1,3,5,7-tetranitro-1,3,5,7-tetrazocine treatment steps. The spent acid is cooled to 20° C. and filtered. The spent acid contains ammonium nitrate (~1.0-1.50 wt %) and acetic anhydride (~20 wt %). An appropriate portion of the anhydrous spent acid is directed toward the heel of the subsequent nitrolysis batch to create a heel with the appropriate amount of acetic anhydride. [The total ammonium nitrate from the heel formation carried into the subsequent nitration step is calculated. An equal molar amount (relative to the amount of ammonium nitrate present in the heel) of nitric acid is added to the heel. 0.50-1.0 molar equivalents (relative to the amount of ammonium nitrate present in the heel) of 1,3,5,7-tetraazatricyclo[3.3.1.1$^{3,7}$] decane are added to the heel.]. The remaining spent acid is directed to the pre-distillation evaporators to separate the volatile components from the nonvolatile components. The pre-distilled acid is then azeotropically distilled to separate the acetic acid from the acetic anhydride. Analogous to what is shown in FIG. 9.

Example 20: Direct Recycle of Spent Acid Octahydro-1,3,5,7-tetranitro-1,3,5,7-tetrazocine Modification-No Nitric Acid Neutralization or Acetic Anhydride Quench Equivalent to the B. Conventional Octahydro-1,3,5,7-tetranitro-1,3,5,7-tetrazocine Process, above, through nitrolysis 45 minute age at 44° C. Upon completion of the nitrolysis age step at 44° C. for 45 minutes, the reaction slurry is warmed to 50-80° C. and filtered to the extent the majority of the acetic acid/acetic anhydride is recovered. No simmer step is required.

The filtered solids are stirred in hot (>90° C.) 0.0-40% nitric acid and heated to reflux, and the new refluxing slurry stirred for 15-60 minutes, followed by cooling to 60° C. (60-80° C.) and filtering. The recovered solids are washed with water then recrystallized via the conventional process. The resulting solution recovered from the hot 0.0-40% nitric acid slurry of the filtered solids is recycled to subsequent crude filtered solids batch treatments. The spent acid is cooled to 20° C. and filtered. An appropriate portion of the anhydrous spent acid with nitric acid present (~2.0-3.0 wt %) and acetic anhydride present (~20 wt %) is recycled to the subsequent nitration batch and the nitric acid, ammonium nitrate and acetic anhydride concentrations adjusted to the correct heel specification before commencing nitration. The remaining spent acid is neutralized with ammonia and quenched with water to 0.0-0.50 wt % acetic anhydride and sent to the pre-distillation evaporator, followed by azeotropic column distillation to separate acetic acid from acetic anhydride. Alternatively, the remaining spent acid can be neutralized with ammonia, followed by quench of acetic anhydride, and the resulting spent acid directly recycled to the hexamine dissolution, or processed through the pre-distillation evaporators. [The total ammonium nitrate from the 1,3,5,7-tetraazatricyclo[3.3.1.1$^{3,7}$]decane feed and heel formation carried into the subsequent nitration step is calculated. An equal molar amount (relative to the amount of ammonium nitrate present in the heel and 1,3,5,7-tetraazatricyclo[3.3.1.1$^{3,7}$]decane feed stream) of nitric acid is added to the heel (minus what is brought in from the untreated spent acid recycle). 0.50-1.0 molar equivalents (relative to the amount of ammonium nitrate present in the heel and 1,3,5,7-tetraazatricyclo[3.3.1.1$^{3,7}$]decane feed stream) of 1,3,5,7-tetraazatricyclo[3.3.1.1$^{3,7}$]decane are added to the heel.] The ANSol recovered from the pre-distillation evaporators can be recycled to the initial crude hexahydro-1,3,5-trinitro-1,3,5-triazine filtration. Analogous to what is shown in FIG. 9.

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the processes and compositions of the present invention, where the term comprises is used with respect to the recited steps of the processes or components of the compositions, it is also contemplated that the processes and compositions consist essentially of, or consist of, the recited steps or components. Furthermore, the order of steps or order for performing certain actions is immaterial so long as the invention remains operable. Moreover, two or more steps or actions can be conducted simultaneously. Furthermore, in some embodiments, not every step is required to be performed so long as the invention remains operable.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as composed of the components prior to mixing, because upon mixing certain components can further react or be transformed into additional materials.

All percentages and ratios used herein, unless otherwise indicated, are in weight percent. It is recognized the mass of an object is often referred to as its weight in everyday usage and for most common scientific purposes, but that mass technically refers to the amount of matter of an object, whereas weight refers to the force experienced by an object due to gravity. Also, in common usage the "weight" (mass) of an object is what one determines when one "weighs" (masses) an object on a scale or balance.

What is claimed is:

1. A methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane), a stream of ammonium nitrate in nitric acid, or sodium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) following the addition in step (a) and a pause of 0-20 minutes at 30-80° C., while maintaining a temperature of about 30-80° C., concurrently introducing a stream of ammonium nitrate in nitric acid, or sodium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) following the addition in step (b) and a pause of 0-20 minutes at 30-80° C., while maintaining a temperature of about 30-80° C., concurrently introducing a stream of ammonium nitrate in nitric acid, or sodium nitrate in nitric acid, and a stream of acetic anhydride into the slurry from step (b), to produce a slurry, wherein the streams are in proportions greater than necessary for producing the octahydro-1,3,5,7-tetranitro-1,3,5,7-tetrazocine;

(d) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid;

(f) quenching the neutralized slurry of step (e) with water to produce an anhydrous spent acid mixture containing about 0.0-20 wt % acetic anhydride;

(g) separating the octahydro-1,3,5,7-tetranitro-1,3,5,7-tetrazocine and the ammonium nitrate from the anhydrous spent acid mixture of step (f);

(h) stirring the octahydro-1,3,5,7-tetranitro-1,3,5,7-tetrazocine from step (g) in a 0.0-90 wt % nitric acid solution at reflux to destroy undesired linear nitramines to provide crude octahydro-1,3,5,7-tetranitro-1,3,5,7-tetrazocine; and (i) collecting the crude octahydro-1,3,5,7-tetranitro-1,3,5,7-tetrazocine from step (h) by filtration.

2. The process of claim 1 comprising the further step of washing the octahydro-1,3,5,7-tetranitro-1,3,5,7-tetrazocine separated from step (g) with hot water to produce washed octahydro-1,3,5,7-tetranitro-1,3,5,7-tetrazocine prior to proceeding to step (h).

3. The process of claim 1 comprising the further step (j) of washing the crude octahydro-1,3,5,7-tetranitro-1,3,5,7-tetrazocine from step (i) is washed with water.

4. The process of claim 3 comprising the further step (k), or the further step (1) of recrystallizing the washed, or unwashed octahydro-1,3,5,7-tetranitro-1,3,5,7-tetrazocine from step (j) or from step (i) respectively, wherein the recrystallization is from a solvent selected from the group consisting of acetone, cyclohexanone, water, dimethyl sulfoxide (DMSO), dimethylformamide (DMF), dimethyacetamide (DMAc), N-methylpyrrolidone (NMP), 2-Methyl-cyclohexanone, cyclohexyne, formamide, γ-butyrolactone, γ-valerolactone, δ-valerolactone, ε-caprolactone, and mixtures thereof.

5. The process of claim 4 comprising the further step (1) of recrystallizing the washed or unwashed octahydro-1,3,5, 7-tetranitro-1,3,5,7-tetrazocine from step (i) from a mixture of water and acetone.

6. The process of claim 1 wherein the ammonia source of step (e) is ammonium acetate.

7. The process of claim 1 wherein step (e) is performed by first cooling the slurry to about 20-60° C., or to about 25-55° C., or to about 45° C. prior to adding the ammonia or ammonia source.

8. The process of claim 1 wherein in step (f) the mixture is subsequently cooled or warmed to about 20-90° C., or about 20-50° C., or to about 25° C. prior to filtration.

9. The process of claim 1 wherein in step (a) the temperatures of one or more of step (a) and step (b) are independently maintained at about 40-75° C., or at about 44° C.

10. The process of claim 1 wherein in step (f) the quenching of the neutralized slurry of step (e) with water is conducted to produce an anhydrous spent acid mixture containing about 0.0-10 wt %, or about 0.0-0.5 wt % acetic anhydride.

11. The process of claim 1 wherein in step (h) the washed or unwashed octahydro-1,3,5,7-tetranitro-1,3,5,7-tetrazocine from step (g) is stirred in about 0-60 wt %, or about 0-40 wt %, or about 0-10 wt % nitric acid solution.

12. The process of claim 1, wherein at least a portion of the anhydrous spent acid mixture from step (e) is directly recycled.

13. The process of claim 12 wherein a portion of the anhydrous spent acid mixture from step (e) is directly recycled via at least one of the following three means:

(i) recycled to the heel, (ii) recycled to dissolve the 1,3,5,7-tetraazatricyclo [3.3.1.1$^{3,7}$]decane, and/or (iii) recycled through pre-distillation evaporators to provide acetic acid and a slurry of acetic acid, RDX, HMX, ammonium nitrate or sodium nitrate, and trace impurities.

14. The process of claim 13 wherein the portion of the anhydrous spent acid mixture from step (g) that is directly recycled through pre-distillation evaporators is followed by conversion of the acetic acid obtained therefrom to acetic anhydride in a ketene furnace.

15. The process of claim 13 wherein the slurry from pre-distillation evaporator is collected and recycled to the crude hexahydro-1,3,5-trinitro-1,3,5-triazine from step (g) from subsequent RDX batches.

16. The process of claim 13 wherein the slurry from pre-distillation evaporator is collected and recycled to the crude octahydro-1,3,5,7-tetranitro-1,3,5,7-tetrazocine from step (g) from subsequent HMX batches.

17. The process of claim 1 wherein the ammonium nitrate content in the 1,3,5,7-tetraazatricyclo[3.3.1.1$^{3,7}$]decane feed stream and/or the acetic acid in the heel are determined and the amount, in moles (y), is calculated, 0.0-0.50 equivalents, relative to (y), of 1,3,5,7-tetraazatricyclo[3.3.1.1$^{3,7}$]decane added to the heel prior the start of stage 1 while maintaining a temperature of 20-50° C., 0.0-1.0 equivalents, relative to (y), of nitric acid added to the heel prior the start of stage 1.

18. The process of claim 1, wherein the resultant aqueous filtrates from one or more of step (j) and step (k) are collected and recycled through pre-distillation evaporators followed by azeotropic distillation.

19. The process of claim 1, wherein while maintaining a temperature of about 20-45° C., to a standard starting heel, containing a mixture comprising a majority of acetic acid with acetic anhydride, are added 0.0-0.10× moles 1,3,5,7-tetraazatricyclo[3.3.1.1$^{3,7}$]decane, 0.0×-0.20× moles ammonium nitrate or sodium nitrate, and 0.0-0.20× moles nitric acid prior to commencing step (a).

20. The process of claim 1, wherein while maintaining a temperature of about 20-45° C., to a standard starting heel, containing a mixture comprising a majority of acetic acid with acetic anhydride, are added 0.10×-0.20× moles 1,3,5, 7-tetraazatricyclo[3.3.1.1$^{3,7}$]decane, 0.20×-0.40× moles ammonium nitrate or sodium nitrate, and 0.20×-0.40× moles nitric acid prior to commencing step (a).

21. The process of claim 1, wherein while maintaining a temperature of about 20-45° C., to a standard starting heel, containing a mixture comprising a majority of acetic acid with acetic anhydride, are added 0.20×-0.30× moles 1,3,5, 7-tetraazatricyclo[3.3.1.1$^{3,7}$]decane, 0.40×-0.60× moles ammonium nitrate or sodium nitrate, and 0.40×-0.60× moles nitric acid prior to commencing step (a).

22. The process of claim 1, wherein while maintaining a temperature of about 20-45° C., to a standard starting heel, containing a mixture comprising a majority of acetic acid with acetic anhydride, are added 0.30×-0.40× moles 1,3,5, 7-tetraazatricyclo[3.3.1.1$^{3,7}$]decane, 0.60×-0.80× moles ammonium nitrate or sodium nitrate, and 0.60×-0.80× moles nitric acid prior to commencing step (a).

23. The process of claim 1, wherein while maintaining a temperature of about 20-45° C., to a standard starting heel, containing a mixture comprising a majority of acetic acid with acetic anhydride, are added 0.40×-0.50× moles 1,3,5, 7-tetraazatricyclo[3.3.1.1$^{3,7}$]decane, 0.80×-1.0× moles ammonium nitrate and 0.80×-1.0× moles nitric acid prior to commencing step (a).

24. The process of claim 1 wherein in step (d), at 0-15 minutes, or at 15-30 minutes, or at 30-45 minutes, of the 45 minute hold time, 0.0-2.0× moles of nitric acid are added while maintaining the temperature at 30-80° C.

25. The process of claim 23 comprising: while maintaining a temperature of about 20-45° C., adding the full quantity of 1,3,5,7-tetraazatricyclo[3.3.1.1$^{3,7}$]decane in acetic acid (x moles of 1,3,5,7-tetraazatricyclo[3.3.1.1$^{3,7}$]decane) to a starting standard heel containing a mixture comprising a majority of acetic acid with acetic anhydride, while maintaining a temperature of about 20-45° C., to the mixture is added ammonium nitrate (1.0×-2.0×) and nitric acid (1.0×-2.0×) prior to commencing step (a), The 1,3,5,7-tetraazatricyclo[3.3.1.1$^{3,7}$]decane in acetic acid feed stream and ammonium nitrate in nitric acid feed stream reduced to zero mass added during step (a).

26. A methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) while maintaining a temperature of about 30-80° C., concurrently introducing a stream of 1,3,5,7-tetraazatricyclo[3.3.1.1$^{3,7}$]decane in acetic acid (x moles 1,3, 5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1, 3,5,7-tetranitro-1,3,5,7-tetrazocine;

(d) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid;

(f) separating the octahydro-1,3,5,7-tetranitro-1,3,5,7-tetrazocine and the ammonium nitrate from the anhydrous spent acid mixture of step (e);

(g) stirring the octahydro-1,3,5,7-tetranitro-1,3,5,7-tetrazocine from step (f) in a 0.0-90 wt % nitric acid solution at reflux to destroy undesired linear nitramines to provide crude octahydro-1,3,5,7-tetranitro-1,3,5,7-tetrazocine; and (h) collecting the crude octahydro-1,3,5,7-tetranitro-1,3, 5,7-tetrazocine from step (g) by filtration.

27. A methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) while maintaining a temperature of about 30-80° C., concurrently introducing a stream of 1,3,5,7-tetraazatricyclo[3.3.1.1$^{3,7}$]decane in acetic acid (x moles 1,3, 5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1, 3,5,7-tetranitro-1,3,5,7-tetrazocine intermediates;

(c) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1, 3,5,7-tetranitro-1,3,5,7-tetrazocine;

(d) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) quenching the slurry of step (d) with water to produce an anhydrous spent acid mixture containing about 0.0-20 wt % acetic anhydride;

(f) separating the octahydro-1,3,5,7-tetranitro-1,3,5,7-tetrazocine and the ammonium nitrate from the anhydrous spent acid mixture of step (e);

(g) stirring the octahydro-1,3,5,7-tetranitro-1,3,5,7-tetrazocine from step (f) in a 0.0-90 wt % nitric acid solution at reflux to destroy undesired linear nitramines to provide crude octahydro-1,3,5,7-tetranitro-1,3,5,7-tetrazocine; and (h) collecting the crude octahydro-1,3,5,7-tetranitro-1,3,5,7-tetrazocine from step (g) by filtration.

28. A methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1,3,5,7-tetranitro-1,3,5,7-tetrazocine;

(d) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) separating the octahydro-1,3,5,7-tetranitro-1,3,5,7-tetrazocine and the ammonium nitrate from the anhydrous spent acid mixture of step (d);

(f) stirring the octahydro-1,3,5,7-tetranitro-1,3,5,7-tetrazocine from step (e) in a 0.0-90 wt % nitric acid solution at reflux to destroy undesired linear nitramines to provide crude octahydro-1,3,5,7-tetranitro-1,3,5,7-tetrazocine; and (g) collecting the crude octahydro-1,3,5,7-tetranitro-1,3,5,7-tetrazocine from step (f) by filtration.

29. A methanoic acid free process for producing octahydro-1,3,5,7-tetranitro-1,3,5,7-tetrazocine, by nitrolysis of 1,3,5,7-tetraazatricyclo[3.3.1.1$^{3,7}$]decane, comprising:

(a) while maintaining a temperature of about 30-80° C., concurrently introducing a stream of 1,3,5,7-tetraazatricyclo[3.3.1.1$^{3,7}$]decane in acetic acid (x moles 1,3,5,7-tetraazatricyclo[3.3.1.1$^{3,7}$]decane), a stream of ammonium nitrate in nitric acid, and a stream of acetic anhydride into a starting heel, the starting heel containing a mixture comprising a majority of acetic acid with acetic anhydride, to produce a slurry, wherein the streams are in proportions greater than necessary for producing the octahydro-1,3,5,7-tetranitro-1,3,5,7-tetrazocine intermediates;

(b) following the addition in step (a) and a pause of 0-20 minutes at 30-80° C., while maintaining a temperature of about 30-80° C., concurrently introducing a stream of ammonium nitrate in nitric acid, and a stream of acetic anhydride into the slurry from step (a), to produce a slurry, wherein the streams are in proportions greater than necessary for producing the octahydro-1,3,5,7-tetranitro-1,3,5,7-tetrazocine intermediates;

(c) following the addition in step (b) and a pause of 0-20 minutes at 30-80° C., while maintaining a temperature of about 30-80° C., concurrently introducing a stream of ammonium nitrate in nitric acid, and a stream of acetic anhydride into the slurry from step (b), to produce a slurry, wherein the streams are in proportions greater than necessary for producing the octahydro-1,3,5,7-tetranitro-1,3,5,7-tetrazocine;

(d) maintaining the resulting slurry from step (c) at about 30-80° C. for about 45 minutes to affect nitrolysis of the 1,3,5,7-tetraazatricyclo[3.3.1.1$^{3,7}$]decane to produce a slurry containing octahydro-1,3,5,7-tetranitro-1,3,5,7-tetrazocine and a spent acid mixture containing acetic acid, acetic anhydride, nitric acid, and ammonium nitrate;

(e) adding ammonia or an ammonia source to the slurry of step (d) sufficient to neutralize the nitric acid;

(f) quenching the neutralized slurry of step (e) with water to produce an aqueous spent acid mixture containing about 0.0-20 wt % aqueous acetic acid;

(g) separating the octahydro-1,3,5,7-tetranitro-1,3,5,7-tetrazocine and the ammonium nitrate from the anhydrous spent acid mixture of step (f);

(h) stirring the octahydro-1,3,5,7-tetranitro-1,3,5,7-tetrazocine from step (g) in a 0.0-90 wt % nitric acid solution at reflux to destroy undesired linear nitramines to provide crude octahydro-1,3,5,7-tetranitro-1,3,5,7-tetrazocine; and (i) collecting the crude octahydro-1,3,5,7-tetranitro-1,3,5,7-tetrazocine from step (h) by filtration.

* * * * *